United States Patent
Foster et al.

(10) Patent No.: US 7,968,100 B2
(45) Date of Patent: Jun. 28, 2011

(54) **SURFACE PROTEINS FROM COAGULASE-NEGATIVE STAPHYLOCOCCI AND *STAPHYLOCOCCUS AUREUS* THAT GENERATE CROSS-REACTIVE MONOCLONAL AND POLYCLONAL ANTIBODIES**

(75) Inventors: Timothy Foster, Dublin (IE); Fiona Roche, Dublin (IE); Mark Pallen, Malvern (GB); Joseph M. Patti, Cumming, GA (US); Jeff T. Hutchins, Cumming, GA (US); Pietro Speziale, Pavia (IT)

(73) Assignees: Universita'Degli Studi Di Pavia, Pavia (IT); Inhibitex, Inc., Alpharetta, GA (US); Provost Fellows and Scholars of the College of the Holy and Undivided Trinity of Queen Elizabeth Near Dublin, Dublin (IE)

( * ) Notice: Subject to any disclaimer, the term of this patent is extended or adjusted under 35 U.S.C. 154(b) by 0 days.

(21) Appl. No.: 12/365,481

(22) Filed: Feb. 4, 2009

(65) Prior Publication Data

US 2009/0202578 A1    Aug. 13, 2009

Related U.S. Application Data

(62) Division of application No. 11/020,509, filed on Dec. 27, 2004, now abandoned, which is a division of application No. 10/172,502, filed on Jun. 17, 2002, now Pat. No. 6,841,154.

(60) Provisional application No. 60/298,098, filed on Jun. 15, 2001.

(51) Int. Cl.
*A61K 39/085* (2006.01)
*A61K 38/16* (2006.01)
*G01N 33/569* (2006.01)

(52) U.S. Cl. ...................................... 424/190.1; 514/12

(58) Field of Classification Search .................. None
See application file for complete search history.

*Primary Examiner* — Robert A Zeman
(74) *Attorney, Agent, or Firm* — B. Aaron Schulman, Esq.; Terry L. Wright, Esq.; Stites & Harbison PLLC

(57) ABSTRACT

Surface proteins are provided which generate polyclonal and monoclonal antibodies which are cross-reactive to both coagulase-positive *staphylococcus* bacteria, such as *S. aureus* and to coagulase-negative bacteria, such as *S. epidermidis* and *S. hemolyticus*. The antibodies may be generated from surface proteins that have been isolated on the basis of characteristics that may be common between *S. aureus* and coagulase-negative staphylococci, or the A domains of those surface proteins, and these recombinant surface proteins are used to generate the cross-reactive antibodies. Vaccines comprising an immunologically effective amount of the proteins are also provided, and these vaccines are used in methods for the treatment or protection against a wide variety of staphylococcal infections.

1 Claim, 12 Drawing Sheets

|        | RESIDUES | PREDICTED MW | APPARENT MW |
|--------|----------|--------------|-------------|
| • RrkN 1 | 60-215 | 19 | 29 |
| • RrkN 2 | 60-437 | 45 | 48 |
| • DsqA 1 | 54-279 | 27 | 38 |
| • DsqA 2 | 54-533 | 58 | 62 |
| • KesK 1 | 55-335 | 34 | 47 |
| • KnkA   | 39-210 | 20 | 27 |
| • KesK 2 | 329-591 | 31 | 40 |

US 7,968,100 B2

SURFACE PROTEINS FROM COAGULASE-NEGATIVE STAPHYLOCOCCI AND *STAPHYLOCOCCUS AUREUS* THAT GENERATE CROSS-REACTIVE MONOCLONAL AND POLYCLONAL ANTIBODIES

CROSS REFERENCE TO RELATED APPLICATIONS

The present application is a divisional application of U.S. patent application Ser. No. 11/020,509, filed Dec. 27, 2004 now abandoned, which is a divisional of U.S. patent application Ser. No. 10/172,502, filed Jun. 17, 2002, now U.S. Pat. No. 6,841,154, issued Jan. 11, 2005, which claims the benefit of U.S. provisional application U.S. Ser. No. 60/298,098 filed Jun. 15, 2001, all of said applications incorporated herein by reference.

FIELD OF THE INVENTION

The present invention relates in general to surface proteins from *Staphylococcus aureus* and their active regions such as their A domains which have homologue proteins on coagulase-negative Staphylococci such as *S. epidermidis* and *S. hemolyticus* as well as antibodies which recognize said proteins, and in particular to isolated monoclonal and polyclonal antibodies which recognize specific proteins from *Staphylococcus aureus* and coagulase-negative Staphylococci and which are cross-reactive against *S. aureus* and coagulase-negative Staphylococci and can thus be utilized in vaccines and methods useful for preventing or treating a wide variety of infections caused by staphylococcal bacteria.

BACKGROUND OF THE INVENTION

The successful colonization of the host is a process required for most microorganisms to cause infections in animals and humans. Microbial adhesion is the first crucial step in a series of events that can eventually lead to disease. Pathogenic microorganisms colonize the host by attaching to host tissues or serum conditioned implanted biomaterials, such as catheters, artificial joints, and vascular grafts, through specific adhesins present on the surface of the bacteria. MSCRAMM®s (Microbial Surface Components Recognizing Adhesive Matrix Molecules) are a family of cell surface adhesins that recognize and specifically bind to distinct components in the host's extracellular matrix. Once the bacteria have successfully adhered and colonized host tissues, their physiology is dramatically altered and damaging components such as toxins and proteolytic enzymes are secreted. Moreover, adherent bacteria often produce a biofilm and quickly become more resistant to the killing effect of most antibiotics.

*S. aureus* causes a spectrum of infections that range from cutaneous lesions such as wound infections, impetigo, and furuncles to life-threatening conditions that include pneumonia, septic arthritis, sepsis, endocarditis, and biomaterial related infections. *S. aureus* is known to express a repertoire of different MSCRAMMs that can act individually or in concert to facilitate microbial adhesion to specific host tissue components. In addition, another type of *staphylococcus* bacteria is identified as the coagulase-negative bacteria, including such species as *S. epidermidis* and *S. hemolyticus* which are also have been known to express MSCRAMMs, and which also are responsible for a wide range of bacterial infections and related diseases. In this regard, MSCRAMMs generally provide an excellent target for immunological attack by antibodies, both polyclonal and monoclonal antibodies.

However, because antibodies by nature are very specific and in the case of different types of Staphylococci, such as *S. aureus* on one hand (coagulase-positive) and *S. epidermidis* and *S. hemolyticus* on the other (coagulase-negative), it has still remained a significant problem to develop antibodies that exhibit cross-reactivity across the different types of bacteria. Such cross-reactive antibodies are particularly desirable because of their potential in immunizing human and animal patients and providing protection against infections caused by both types of Staphylococcal bacteria, namely coagulase-positive bacteria such as *S. aureus* and the coagulase-negative bacteria, such as *S. epidermidis* and *S. hemolyticus*. Such antibodies would thus be extremely useful in preventing or treating a wide variety of the infections caused by staphylococcal bacteria.

SUMMARY OF THE INVENTION

Accordingly, it is an object of the present invention to provide monoclonal antibodies that recognize MSCRAMM®'s from both coagulase-positive bacteria such as *S. aureus* as well as MSCRAMM®'s from coagulase-negative bacteria, such as *S. epidermidis* and *S. hemolyticus*.

It is also an object of the present invention to identify and isolate MSCRAMM®'s from staphylococcal bacteria, as well as their active regions such as the A domain, which can be used to generate monoclonal and polyclonal antibodies that will be cross-reactive against both coagulase-positive and coagulase-negative staphylococci.

It is still further an object of the present invention to provide isolated antibodies that can recognize the A domain of surface proteins such as the DgsK protein from coagulase-negative staphylococci and at the same time recognize surface proteins such as the SasA protein from *Staphylococcus aureus*.

It is yet another object of the present invention to utilize the isolated proteins, A domains and antibodies of the invention to produce vaccines useful in the treatment or prevention of staphylococcal infections, and to provide methods wherein the vaccines and antibodies of the invention are used to prevent or treat a staphylococcal infection.

These and other objects are provided by virtue of the present invention which comprises the identification and isolation of surface proteins from one type of staphylococcal bacteria, such as coagulase-negative or coagulase-positive *staph*, which can give rise to cross-reactive antibodies which can recognize surface proteins of both types of *staph* and which can thus be utilized in vaccines and methods of treating or preventing a wide range of staphylococcal infections. The present invention also relates to the generation of both polyclonal and monoclonal antibodies from these surface proteins and their use in preventing or treating staphylococcal infections.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

Figure 5A:
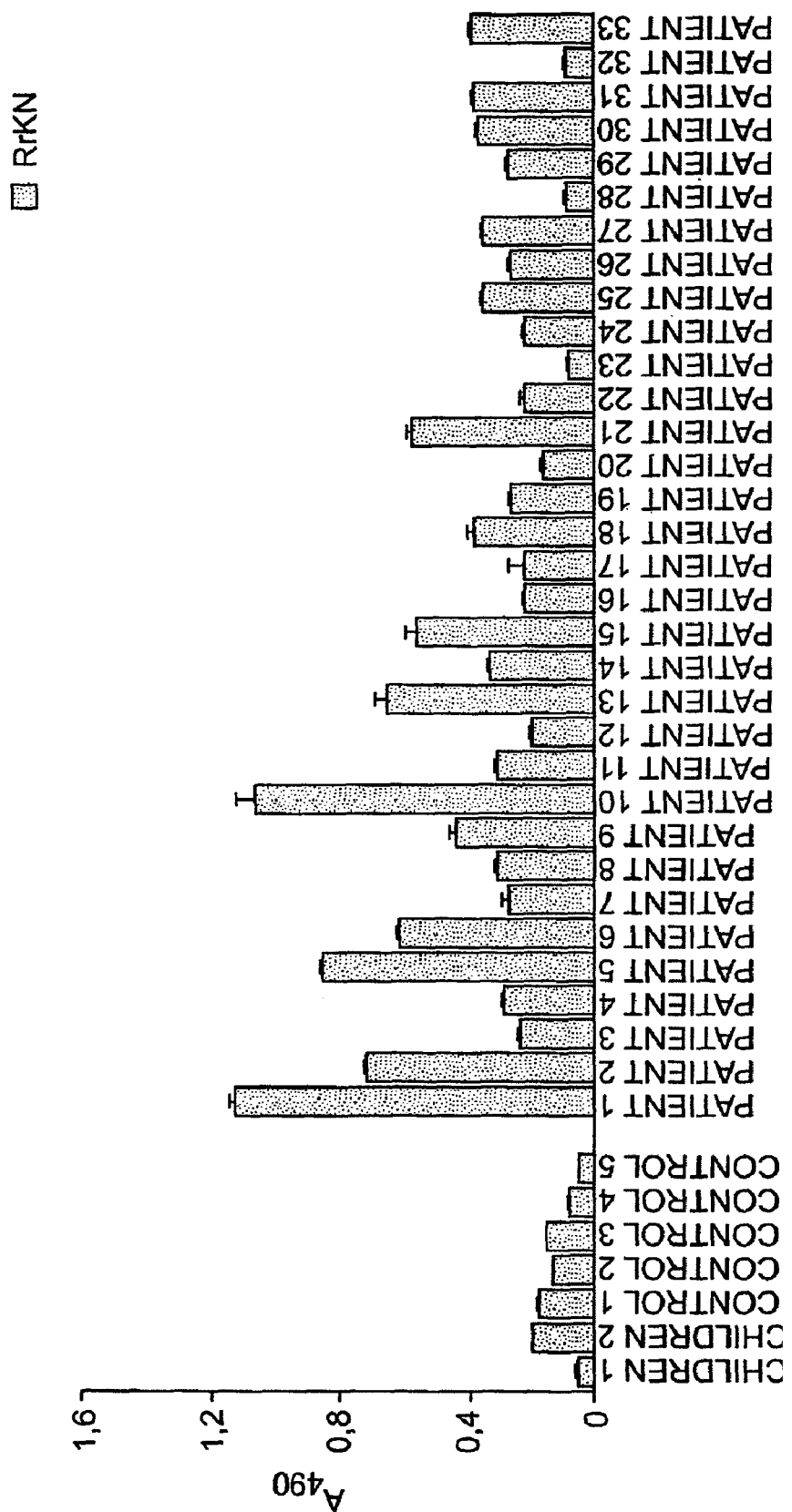
Figure 5A:
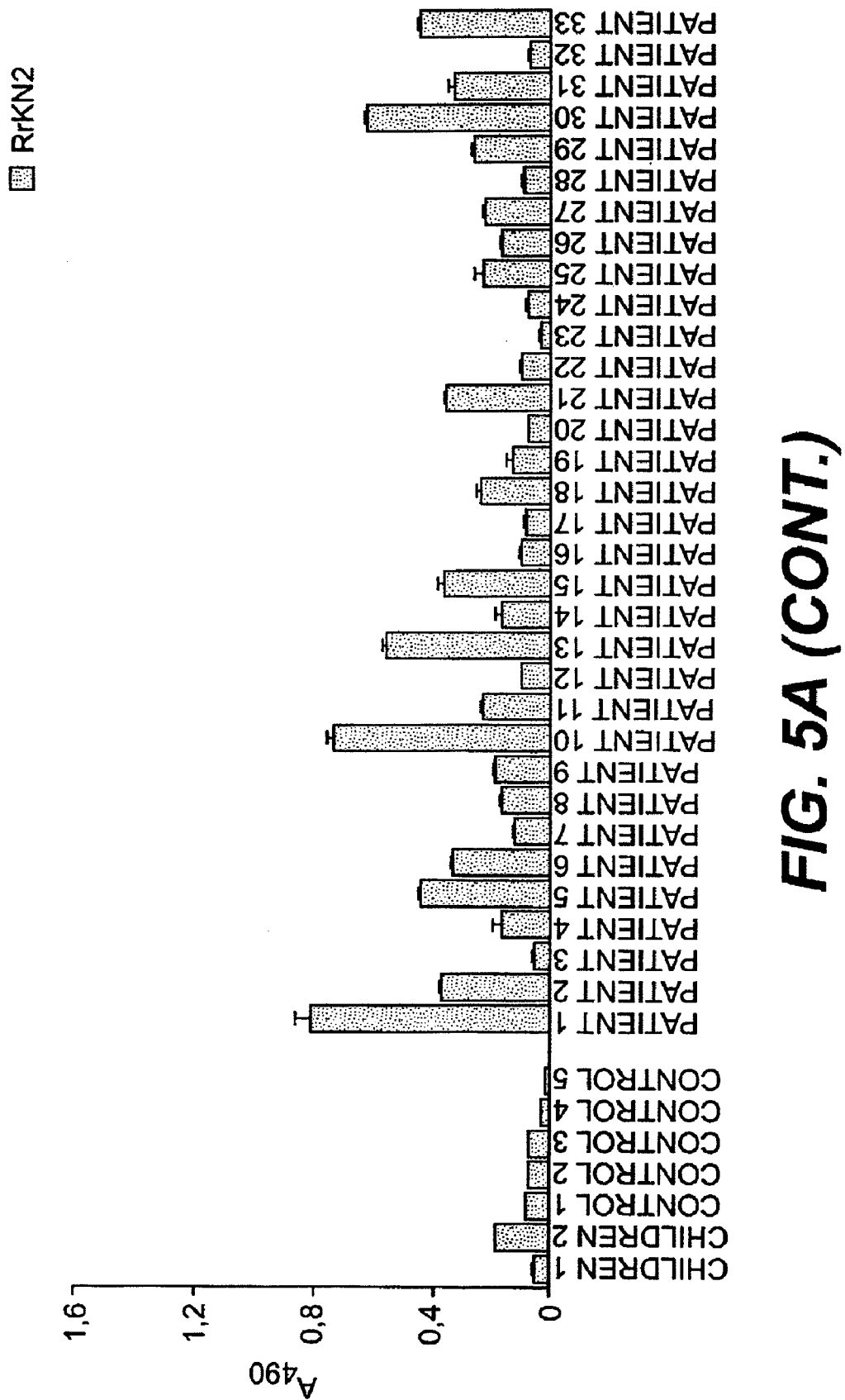
Figure 5B:
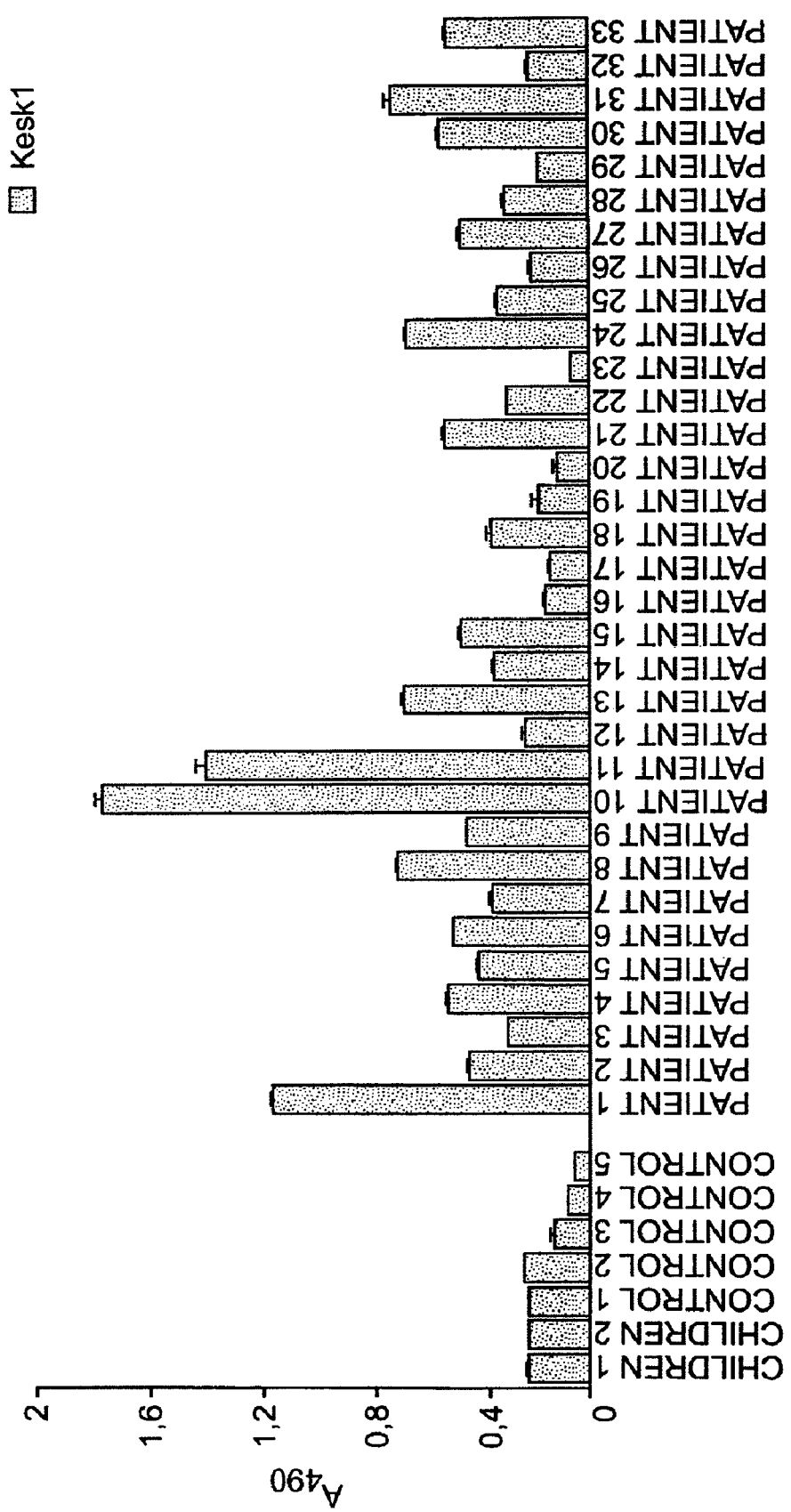
Figure 5B:
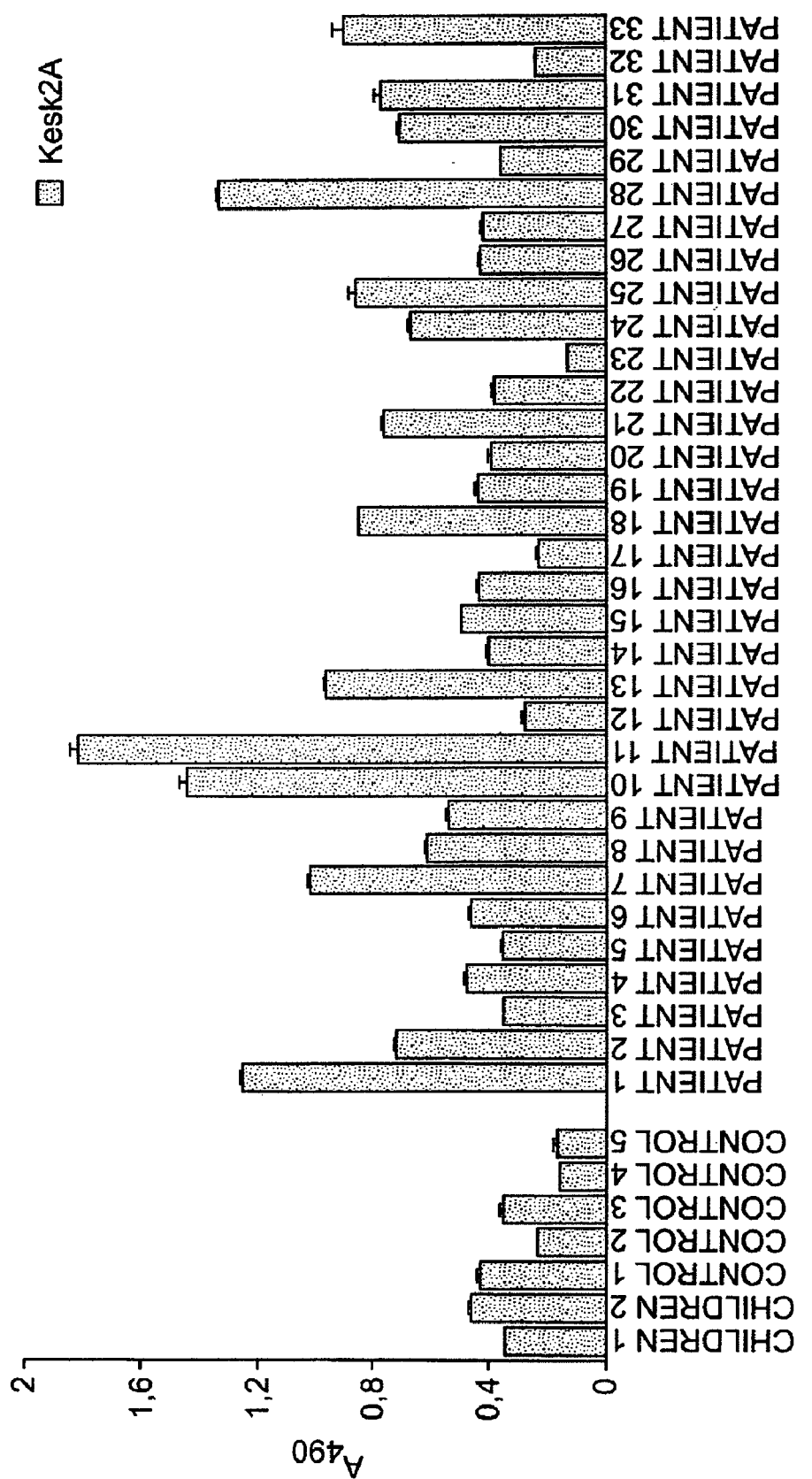
Figure 5C:
Figure 5D:
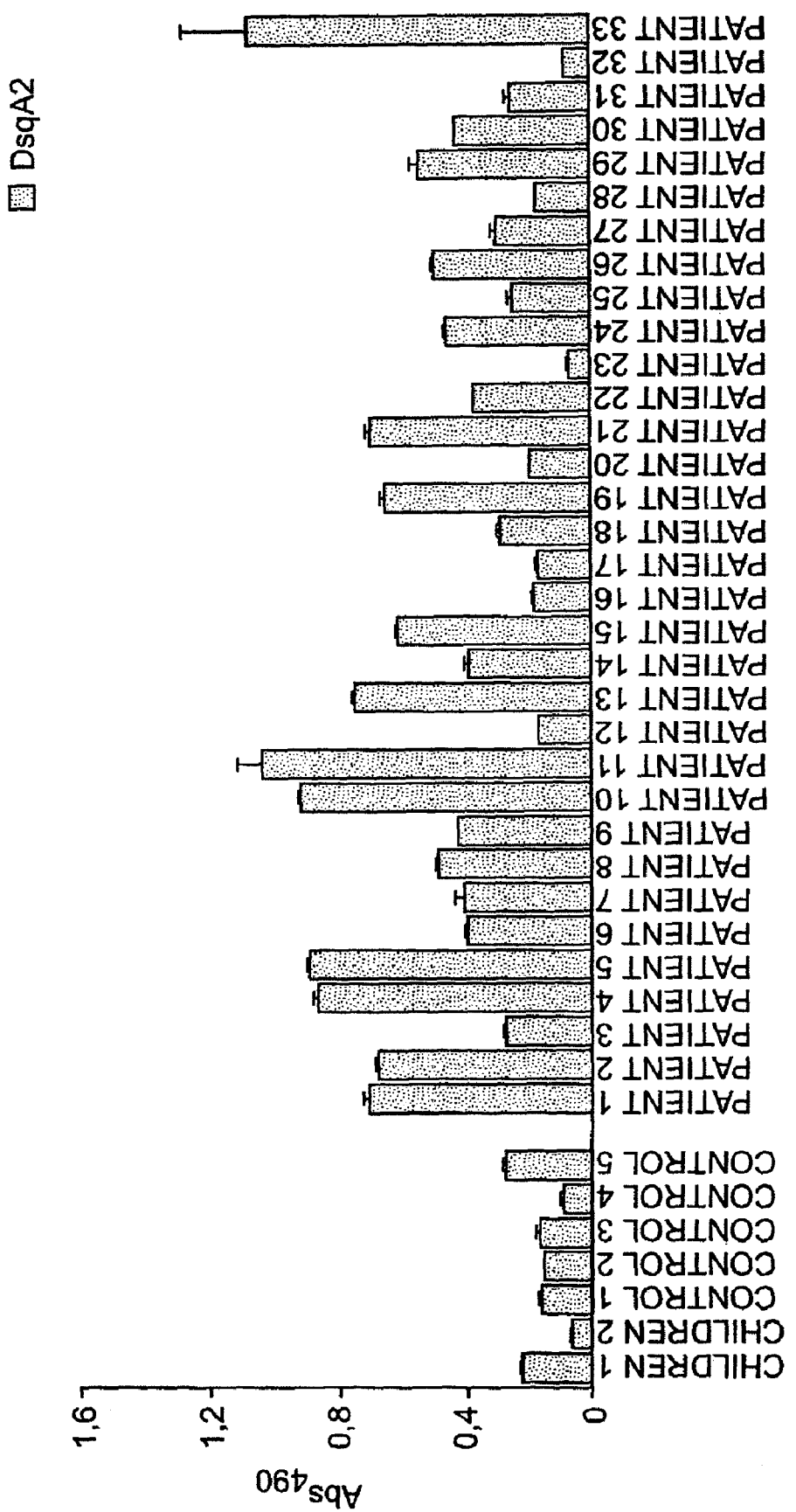

FIGS. 5A-5D representing the probing of recombinant LPXTG proteins in accordance with the present invention with convalescent sera examining in vivo expression, including RrKn and RrKN2 (FIG. 5A), Kesk1 and Kesk2A (FIG. 5B), KnkA (FIG. 5C) and DsqA2 (FIG. 5D).

Figure 6:
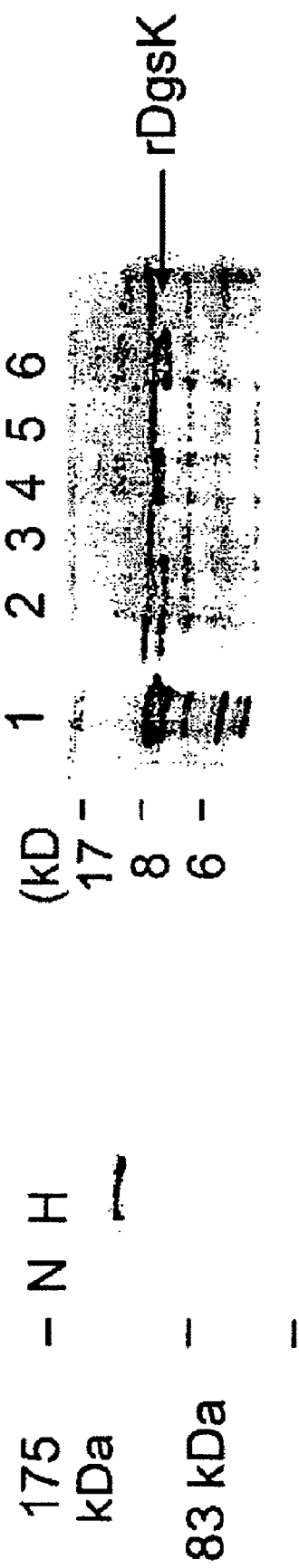

FIG. 6 shows a Western blot analysis demonstrating that rabbit polyclonal antibodies against *S. aureus* SasA cross-react with a protein released from the cell surface of *S. epidermidis* HB as well as the recombinant A-region from DsgK cloned from *S. epidermidis*.

DETAILED DESCRIPTION OF THE PREFERRED EMBODIMENTS

In accordance with the present invention, there are provided specific surface proteins from coagulase-positive staphylococcal bacteria, such as *S. aureus* as well as from coagulase-negative staph such as *S. epidermidis* and *S. hemolyticus*, including active fragments thereof such as the A domains of these proteins or other epitotic regions which can generate antibodies that recognize the whole protein. In accordance with the invention, the identification and isolation of candidate peptide sequences and proteins was carried out based on some of the common features of the MSCRAMM®s ((Microbial Surface Components Recognizing Adhesive Matrix Molecules) which are in most cases are covalently anchored to the cell wall peptidoglycan. These surface proteins had the following common features which were utilized in identifying and isolated the sequences of the present invention, namely: (i) an N-terminal signal peptide (approximately 40 residues in length) required for Sec-dependent secretion, (ii) a wall spanning domain either rich in proline and glycine residues or composed of serine and aspartate dipeptide repeats, (iii) an LPXTG motif required for covalent anchoring of the protein to the pentaglycine crossbridge in peptidoglycan, (iv) a hydrophobic membrane-spanning domain followed by (v) several positively charged residues.

In accordance with the invention, by exploiting the whole genome of *S. aureus* in light of the properties as set forth above, at least eight novel open reading frames encoding proteins with secretion and anchorage motifs indicative of MSCRAMMs were identified (i.e. bearing an N-terminal signal peptide and a C-terminal LPXTG motif followed by a hydrophobic domain and a positively charged tail). Table 1 illustrates the list of proteins identified including their distribution among *S. aureus* genomes, their protein size and C-terminal cell wall sorting sequence.

TABLE 1

| Name | Distribution | Size | C-terminus |
|---|---|---|---|
| EkeS | ENCSJM | 2189 aa | LPNTGSEEMDLPLKELALITGA ALLARRRSKKEKES (SEQ ID NO: 22) |
| DsqA | ENCSJM | ~1363-2283 aa | LPDTGDSIKQNGLLGGVMTLLV GLGLMKRKKKKDENDQDDSQA (SEQ ID NO: 23) |
| KesK | ENCSJM | ~909 aa | LPKTGETTSSQSWWGLYALLGM LALFIPKFRKESK (SEQ ID NO: 24) |
| KrkN2 | ENCSJM (Cowan) | ~278 aa | LPKTGLTSVDNFISTVAFATLA LLGSLSLLLFKRKESK (SEQ ID NO: 25) |
| KrkN | ENCSJM | ~661 aa | LPQTGEESNKDMTLPLMALIAL SSIVAFVLPRKRKN (SEQ ID NO: 26) |
| RkaS | ENCSJM | ~801 aa | LPKTGTNQSSSPEAMFVLLAGI GLIATVRRRKAS (SEQ ID NO: 27) |
| RrkN | NCSJM | 1629 aa | LPKTGLESTQKGLIFSSIIGIA GLMLLARRRKN (SEQ ID NO: 28) |
| KnkA | NCSJM | 629 aa | LPKAGETIKEHWLPISVIVGAM GVLMIWLSRRNKLKNKA (SEQ ID NO: 29) |

Abbreviations: eMRSA-16; N, 8325; C, COL; S, MSSA; J, N315, M, Mu50.
Six out of eight are conserved in all of the six staphylococcal genomes currently sequenced and the remaining two are present in 5/6 of these genomes.

In accordance with the invention, amino acid and nucleic acid sequences coding for the above proteins were obtained, and these were as follows: Ekes MRSA—SEQ ID NO:1 (DNA sequence); EkeS_MRSA—SEQ ID NO:2 (Protein sequence); DsqA (8325)—SEQ ID NO:3 (DNA sequence); DsqA (8325)—SEQ ID NO:4 (Protein sequence); KesK1 (8325)—SEQ ID NO:5 (DNA sequence); KesK1 (8325)—SEQ ID NO:6 (Protein sequence); KrkN2 (8325)—SEQ ID NO:7 (DNA sequence); KrkN2 (8325)—SEQ ID NO:8 (Protein sequence); KrkN (8325)—SEQ ID NO:9 (DNA sequence); KrkN (8325)—SEQ ID NO:10 (Protein sequence); RkaS (COL)—SEQ ID NO:11 (DNA sequence); RkaS (COL)—SEQ ID NO:12 (Protein sequence); RrkN (8325)—SEQ ID NO:13 (DNA sequence); RrkN (8325)—SEQ ID NO:14 (Protein sequence); KnkA (8325)—SEQ ID NO:15 (DNA sequence); KnkA (8325)—SEQ ID NO:16 (Protein sequence).

In accordance with the present invention, isolated antibodies may be generated from the above proteins or their active regions such as the A domain so as to be able to recognize said proteins and/or said domains. These antibodies may be either monoclonal or polyclonal. If polyclonal antibodies are desired, these may be generated in any of a number of conventional ways well known in the art. In a typical process, the desired surface protein or active region thereof may be injected into a suitable host animal, e.g., a mouse or rabbit, and after a suitable time period, antibodies may be isolated and recovered from the host animal. With regard to monoclonal antibodies, in accordance with the present invention, these may be produced in any number of suitable ways including, e.g., the well known method of Kohler and Milstein, Nature 256:495-497 (1975), or other suitable ways known in the field, such as those methods disclosed in U.S. Pat. Nos. 6,331,415; 5,981,216; 5,807,715; and 4,816,567; Eur. Pat. App. 519,596; and PCT publication WO 00/71585, all of these patent publications incorporated herein by reference. These methods include their preparation as chimeric, humanized, or human monoclonal antibodies in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which binds to the particular surface protein or its homologue from the different type of *staph* bacteria (i.e., coagulase negative or coagulase-positive), and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

As indicated above, antibodies to the isolated surface proteins and/or their active regions in accordance with the invention may be prepared in a number of suitable ways that would be well known in the art, such as the well-established Kohler and Milstein method described above which can be utilized to generate monoclonal antibodies. For example, in preliminary steps utilized in such a process, mice may be injected intraperitoneally once a week for a prolonged period with a purified recombinant MSCRAMM® in accordance with the invention or an active portion thereof, followed by a test of blood obtained from the immunized mice to determine reactivity to the purified protein. Following identification of mice reactive to the proteins, lymphocytes isolated from mouse spleens are fused to mouse myeloma cells to produce hybridomas positive for the antibodies against the surface proteins of the invention which are then isolated and cultured, following by purification and isotyping.

In order to generate monoclonal antibodies in accordance with the invention, it is preferred that these be generated using recombinantly prepared MSCRAMM®'s in accordance with the invention, and these recombinants may be generated and isolated using a number of standard methods well known in the art. For example, one such method employs the use of *E. Coli* expression vector pQE-30 as an expression vector for cloning and expressing recombinant proteins and peptides. In one preferred method, using PCR, the A domain of the surface protein identified as DgsK or SasA was amplified from the sequences described above and subcloned into the *E. Coli* expression vector PQE-30 (Qiagen), which allows for the expression of a recombinant fusion protein containing six histidine residues. This vector was subsequently transformed into *E. coli* strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size 0.45 μm) and the cell paste frozen at −80° C. Cells were lysed in 1×PBS (10 mL buffer/1 g of cell paste) using 2 passes through the French Press@ 1100 psi. Lysed cells were spun down at 17,000 rpm for 30 minutes to remove cell debris. Supernatant was passed over a 5-mL HiTrap Chelating (Pharmacia) column charged with 0.1 M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 200 mM imidazole (Buffer B) over 30 column volumes. SdrGN1N2N3 or SdrGN2N3 eluted at ~13% Buffer B (~26 mM imidazole). Absorbance at 280 nm was monitored. Fractions containing SdrGN1N2N3 or SdrGN2N3 were dialyzed in 1×PBS.

Next, each protein was then put through an endotoxin removal protocol. Buffers used during this protocol were made endotoxin free by passing over a 5-mL Mono-Q sepharose (Pharmacia) column. Protein was divided evenly between 4×15 mL tubes. The volume of each tube was brought to 9 mL with Buffer A. 1 mL of 10% Triton X-114 was added to each tube and incubated with rotation for 1 hour at 4° C. Tubes were placed in a 37° C. water bath to serrate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with 0.1M $NiCl_2$ to remove remaining detergent. The column was washed with 9 column volumes of Buffer A before the protein was eluted with 3 column volumes of Buffer B. The eluant was passed over a 5-mL Detoxigel (Sigma) column and the flow-through collected and reapplied to the column. The flow-through from the second pass was collected and dialyzed in 1×PBS. The purified product was analyzed for concentration, purity and endotoxin level before administration into the mice.

In the preferred process, monoclonal antibodies in accordance with the present invention may be prepared from the recombinant proteins identified above in the following manner. In this process, *E. coli* expressed and purified recombinant SasA and DsgK proteins were used to generate a panel of murine monoclonal antibodies while the mouse sera was used as a source of polyclonal antibodies. Briefly, a group of Balb/C or SJL mice received a series of subcutaneous immunizations of 1-10 mg of protein in solution or mixed with adjuvant as described below in Table 2.

TABLE 2

| Immunization Schemes | | | | |
|---|---|---|---|---|
| | Day | Amount (μg) | Route | Adjuvant |
| RIMMS Injection | | | | |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection | | | | |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against MSCRAMM® proteins or on whole cells (*S. epidermidis* and *S. aureus*). Three days after the final boost, the spleens or lymph nodes were removed, teased into a single cell suspension and the lymphocytes harvested. Lymphocytes were then fused to a P3X63Ag8.653 myeloma cell line (ATCC #CRL-1580). Cell fusion, subsequent plating and feeding were performed according to the Production of Monoclonal Antibodies protocol from *Current Protocols in Immunology* (Chapter 2, Unit 2.), incorporated herein by reference.

Any clones that were generated from the fusion were then screened for specific anti-SasA antibody production using a standard ELISA assay. Positive clones were expanded and tested further for activity in a whole bacterial cell binding assay by flow cytometry and SasA binding by Biacore analysis. Throughout the Biacore analysis, the flow rate remained constant at 10 ml/min. Prior to the SasA or DgsK injection, test antibody was adsorbed to the chip via RAM-Fc binding. At time O, SasA or DgsK at a concentration of 30 mg/ml was injected over the chip for 3 min followed by 2 minutes of dissociation. This phase of the analysis measured the relative association and disassociation kinetics of the Mab/SasA or DgsK interaction.

Next, the antibodies prepared as set forth above were tested for binding to whole bacteria. In these tests, bacterial samples S. aureus Newman, S. aureus 67-0, S. aureus 397 (Sal6), S. aureus Wood, S. aureus 8325-4, methicillin resistant S. aureus MRSA 16, S. epidermidis ATCC 35984, S. epidermidis HB, S. epidermidis CN-899 and S. haemolyticus ATCC 43253 were collected, washed and incubated with Mab or PBS alone (control) at a concentration of 2 μg/ml after blocking with rabbit IgG (50 mg/ml). Following incubation with antibody, bacterial cells were incubated with Goat-$F_{(ab)2}$-Anti-Mouse-$F_{(ab)2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured. These data indicate that antibodies against S. aureus SasA were able to recognize a homologous protein on the surface of coagulase-negative staphylococci. The data support Western blot analysis demonstrating that rabbit polyclonal antibodies against S. aureus SasA cross-react with a protein released from the cell surface of S. epidermidis HB as well as the recombinant A-region from DsgK cloned from S. epidermidis (see FIG. 6 and Table 3 below).

would be recognized by one of ordinary skill in this art. Suitable methods of administering any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol. Additional forms of antibody compositions, and other information concerning compositions, vaccines, methods and applications with regard to other MSCRAMM®s will generally also be applicable to the present invention involving the aforementioned MSCRAMM®s and their active regions and antibodies thereto, and these other MSCRAMM®s are disclosed, for example, in U.S. Pat. Nos. 5,175,096; 5,320,951; 5,416,021; 5,440,014; 5,571,514; 5,652,217; 5,707,702; 5,789,549; 5,840,846; 5,980,908; 6,086,895; 6,008,341; 6,177,084; 5,851,794 and 6,288,214; all of these patents incorporated herein by reference.

TABLE 3

| | | | | | | | | | |
|---|---|---|---|---|---|---|---|---|---|
| | | | | Polyclonal Sera Reactivity | | | | | |
| | Newman | 67-0 | 397 (SAL 6) | Wood 46 | 8325-4 | MRSA 16 | ATCC 35984 | HB | CN-899 | ATCC 43253 |
| Normal Mouse Sera | − | − | − | − | − | − | − | − | − | − |
| Mouse anti-SasA | + | + | +/− | − | + | + | + | + | + | + |

Although production of antibodies using recombinant forms of the surface proteins of the present invention is preferred, antibodies may be generated from natural isolated and purified versions of these proteins or their active regions such as the A domain, and monoclonal or polyclonal antibodies can be generated using these proteins or active regions in the same manner as described above to obtain such antibodies. Still other conventional ways are available to generate the antibodies of the present invention using recombinant or natural purified proteins or their active regions, as would be recognized by one skilled in the art.

As would be recognized by one skilled in the art, the antibodies of the present invention may also be formed into suitable pharmaceutical compositions for administration to a human or animal patient in order to treat or prevent an infection caused by staphylococcal bacteria. Pharmaceutical compositions containing the antibodies of the present invention, or effective fragments thereof, may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as The antibody compositions of the present invention may also be administered with a suitable adjuvant in an amount effective to enhance the immunogenic response. For example, suitable adjuvants may include alum (aluminum phosphate or aluminum hydroxide), which is used widely in humans, and other adjuvants such as saponin and its purified component Quil A, Freund's complete adjuvant, RIBBI adjuvant, and other adjuvants used in research and veterinary applications. Still other chemically defined preparations such as muramyl dipeptide, monophosphoryl lipid A, phospholipid conjugates such as those described by Goodman-Snitkoff et al. J. Immunol. 147:410-415 (1991) and incorporated by reference herein, encapsulation of the conjugate within a proteoliposome as described by Miller et al., J. Exp. Med. 176:1739-1744 (1992) and incorporated by reference herein, and encapsulation of the protein in lipid vesicles such as Novasome lipid vesicles (Micro Vescular Systems, Inc., Nashua, N.H.) may also be useful.

In any event, the antibody compositions of the present invention which recognize the proteins or their active regions as set forth above will be useful in methods of preventing or treating staphylococcal infection, and in inhibiting binding of staphylococcal bacteria to host tissue and/or cells. In accordance with the present invention, methods are provided for preventing or treating a staphylococcal infection which comprise administering an effective amount of an antibody to the surface proteins as set forth herein or their active subregions so as to treat or prevent a staphylococcal infection. In addition, these monoclonal antibodies will be useful in impairing the binding of staphylococcal bacteria to host cells Accordingly, in accordance with the invention, administration of the antibodies of the present invention in any of the conventional ways described above (e.g., topical, parenteral, intramuscular, etc.), and will thus provide an extremely useful method of treating or preventing staphylococcal infections in human or animal patients when an effective amount of the antibody compositions are administered to a human or animal patient. By effective amount is meant that level of use, such as of an antibody titer, that will be sufficient to either prevent adherence of the bacteria, to inhibit binding of *staph* bacteria to host cells and thus be useful in the treatment or prevention of a *staph* infection. As would be recognized by one of ordinary skill in this art, the level of antibody titer needed to be effective in treating or preventing staphylococcal infection will vary depending on the nature and condition of the patient, and/or the severity of the pre-existing staphylococcal infection.

In addition to use in methods or treating or preventing a staphylococcal infection, the antibodies of the invention may also be used for the specific detection of staphylococcal proteins, or as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies to the surface proteins specified above, including the products of an Fab immunoglobulin expression library. Accordingly, the invention contemplates the use of single chains such as the variable heavy and light chains of the antibodies. Generation of any of these types of antibodies or antibody fragments is well known to those skilled in the art. In the present case, antibodies to the surface proteins or their active regions as referred to above can be generated, isolated and/or purified, and then used to treat or protect against staphylococcal infection.

Any of the above described antibodies may be labeled directly with a detectable label for identification and quantification of *staph* bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

In accordance with the present invention, there are also provided vaccines for either active or passive immunization designed to treat or protect against staphylococcal infections, and these vaccines may be prepared from the surface proteins or their active regions as set forth above using a number of the conventional vaccine preparation methods well known in this field. In the typical vaccine, an immunogenic amount of a suitable surface protein or active fragment thereof is combined with a suitable pharmaceutically acceptable vehicle, carrier or excipient, and an amount of this vaccine effective to immunize a human or animal patient may be administered as appropriate. By immunogenic amount it would be understood by one of ordinary skill in this art that this refers to any amount of the protein or active fragment or subregion thereof which is able to raise an immunogenic response in the human or animal patient.

In addition to active vaccines wherein antibodies are generated in the patient by virtue of the introduction or administration of an immunogenic amount of a protein or active fragment in accordance with the present invention, the isolated antibodies of the present invention, or active fragments thereof, may also be utilized in the development of vaccines for passive immunization against *staph* infections. In such a case, the antibody compositions as described above, namely an effective amount of the antibody and a pharmaceutically acceptable vehicle, carrier or excipient, may be administered as appropriate to a human or animal patient.

Accordingly, in accordance with the invention, the proteins or active fragments thereof may be utilized as active vaccines, and the antibodies of the invention may be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable vehicle, carrier or excipient to facilitate administration, and the carrier is usually water or a buffered saline, with or without a preservative. The vaccine may be lyophilized for resuspension at the time of administration or in solution.

In addition, in certain cases, the antibodies of the present invention may be modified as necessary so that, when necessary, they become less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522-525 (1986) or Tempest et al. *Biotechnology* 9:266-273 (1991) or "veneered" by changing the surface exposed murine framework residues in the immunoglobulin variable regions to mimic a homologous human framework counterpart as described, e.g., by Padlan, Molecular Imm. 28:489-498 (1991), these references incorporated herein by reference. Even further, when so desired, the monoclonal antibodies of the present invention may be administered in conjunction with a suitable antibiotic to further enhance the ability of the present compositions to fight bacterial infections when necessary.

In addition to treating human or animal patients, the present compositions may also be used to halt or prevent infection of a medical device or other biomaterials such as an implant. Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or active fragment, or pharmaceutical composition derived therefrom, to a surface of the device, preferably an outer surface that would be exposed to streptococcal bacterial infection. The surface of the device need not be entirely covered by the protein, antibody or active fragment.

The preferred dose for administration of an antibody composition in accordance with the present invention is that amount will be effective in preventing of treating a staphylococcal infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may also contain stabilizers or pharmaceutically acceptable preservatives, such as thimerosal (ethyl(2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of staphylococcal infections or detection of staphylococcal bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}$P, $^{3}$H, $^{14}$C, $^{35}$S, $^{125}$I, or $^{131}$I. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to one skilled in the art, such as immunofluorescence microscopy using procedures such as those described by Warren et al. (*Mol. Cell. Biol.*, 7: 1326-1337, 1987).

As indicated above, the monoclonal antibodies of the present invention, or active portions or fragments thereof, are particularly useful for interfering with the initial physical interaction between a staphylococcal pathogen responsible for infection and a mammalian host, and this interference with the physical interaction may be useful both in treating patients and in preventing or reducing bacteria infection on in-dwelling medical devices to make them safer for use.

In another embodiment of the present invention, a kit which may be useful in isolating and identifying staphylococcal bacteria and infection is provided which comprises the antibodies of the present invention in a suitable form, such as lyophilized in a single vessel which then becomes active by addition of an aqueous sample suspected of containing the staphylococcal bacteria. Such a kit will typically include a suitable container for housing the antibodies in a suitable form along with a suitable immunodetection reagent which will allow identification of complexes binding to the surface proteins or the antibodies of the invention. In general, these kits may contain an antibody in accordance with the invention and means to identify binding of that antibody when a sample from a patient is introduced to the antibody. For example, a suitable immunodetection reagent may comprise an appropriate detectable signal or label, such as a biotin or enzyme that produces a detectable color, etc., which may be linked to the antibody or utilized in other suitable ways so as to provide a detectable result when the antibody binds to the antigen.

In short, the antibodies of the present invention which recognize and bind to the surface proteins of the invention, or active fragments thereof, will thus be useful in treating a wide variety of staphylococcal infections in human and animal patients and in medical or other in-dwelling devices. In accordance with the invention, because of the nature of these proteins and the fact that they contain epitopes in common with proteins of the other type of staphylococcal bacteria, i.e., a protein from a coagulase-negative *staph* will raise antibodies that recognize a homologous protein from *S. aureus* and vice versa, the antibodies of the invention will exhibit cross-reactivity and should be effective against a broad range of staphylococcal infections. Accordingly, the present invention provides methods and compositions for improved methods of treating or protecting against a wide range of staphylococcal infections.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Sequencing of MSCRAMM's from S. Aureus

*Staphylococcus aureus* is known to express a class of surface-associated proteins which play important roles in pathogenicity by allowing bacteria to avoid host defenses and by acting as adhesins. These proteins are known as MSCRAMMs (Microbial Surface Components Recognizing Adhesive Matrix Molecules) and in most cases are covalently anchored to the cell wall peptidoglycan. They have several common features: (i) an N-terminal signal peptide (approximately 40 residues in length) required for Sec-dependent secretion, (ii) a wall spanning domain either rich in proline and glycine residues or composed of serine and aspartate dipeptide repeats, (iii) an LPXTG motif required for covalent anchoring of the protein to the pentaglycine crossbridge in peptidoglycan, (iv) a hydrophobic membrane-spanning domain followed by (v) several positively charged residues.

By exploiting the whole genome sequences of *S. aureus*, eight novel open reading frames encoding proteins with secretion and anchorage motifs indicative of MSCRAMMs were identified (i.e. bearing an N-terminal signal peptide and a C-terminal LPXTG motif followed by a hydrophobic domain and a positively charged tail). The following Table illustrates the list of proteins identified including their distribution among *S. aureus* genomes, their protein size and C-terminal cell wall sorting sequence.

| Name | Distribution | Size | C-terminus |
|---|---|---|---|
| EkeS | ENCSJM | 2189 aa | LPNTGSEEMDLPLKELALITGA ALLARRRSKKEKES (SEQ ID NO: 22) |
| DsqA | ENCSJM | ~1363- 2283 aa | LPDTGDSIKQNGLLGGVMTLLV GLGLMKRKKKKDENDQDDSQA (SEQ ID NO: 23) |
| KesK | ENCSJM | ~909 aa | LPKTGETTSSQSWWGLYALLGM LALFIPKFRKESK (SEQ ID NO: 24) |
| KrkN2 | ENCSJM (Cowan) | ~278 aa | LPKTGLTSVDNFISTVAFATLA LLGSLSLLLFKRKESK (SEQ ID NO: 25) |
| KrkN | ENCSJM | ~661 aa | LPQTGEESNKDMTLPLMALIAL SSIVAFVLPRKRKN (SEQ ID NO: 26) |
| RkaS | ENCSJM | ~801 aa | LPKTGTNQSSSPEAMFVLLAGI GLIATVRRRKAS (SEQ ID NO: 27) |
| RrkN | NCSJM | 1629 aa | LPKTGLESTQKGLIFSSIIGIA GLMLLARRRKN (SEQ ID NO: 28) |
| KnkA | NCSJM | 629 aa | LPKAGETIKEHWLPISVIVGAM GVLMIWLSRRNKLKNKA (SEQ ID NO: 29) |

Abbreviations: eMRSA-16; N, 8325; C, COL; S, MSSA; J, N315, M, Mu50.
Six out of eight are conserved in all of the six staphylococcal genomes currently sequenced and the remaining two are present in 5/6 of these genomes.

The following is a list of the DNA and protein sequences:

Ekes MRSA
(SEQ ID NO: 1)
acaacacagcagagaatagacaaccaggaggaaaacgaaatgaatttgtt aaagaaaaataaatatagtattagaaaatataaagtagggatattctcta cttaatcgggacagttttattactttcaaacccaaatggtgcacaagct ttaactacggatcataatgtgcaaggtggttcaaatcaagcattacctgg caactcacaaaatacaaatgccgatactaatcgagacatagtaaatgatt cgcaaaatactcctaatgcacatgcaacagacaatacatcaacaaatcaa gcattgactaatcatcaaaacgttgatgtggcaaatcaagtcgggcctgc tccaatacagcctagcgcgtcgcctgcgcaaaataataataattctaatg ctaattcaacagcaacagagccagcggcgaatacaaataataatttagca tcaaataacaatacattaaacgtgcctaataatacagataacaatgattc agcgcgtcatctgactttaaaagaaattcaagaagatgttcgtcattcgt ctgataagccagagttagttgcgattgctgaagaagcatctaatagaccg aaaagagaagcagacgtgctgcgccaacagatcctaatgcaacaccagc agatccaacggctacaccagcagatccaacggcaggaaatggtagtgcac cagttgcaattacagcgccatacacgccaacaactgatcccaatgccaat aatataggacaaaatgcacctaacgaagtgctttcatttgatgataacaa cattagaccaagtacgaaccgttctgtgcctacagtaactgttgttgata atttaccaggctacacactgattaatggtggtaaagtaggggtgtttagt catgcaatggtaagaacgagcatgtttgattcaggagatgccaagaacta tcaagcgcaaggcaatgtaattgcattgggtcgtattagaggaaatgata caaatgatcatggcgatttaatggtatcgagaaaacattaacagtaaat ccgaattctgaattaatctttgaatttaatactatgactactaaaaacta tcaaggtatgacaaatttaatcattaaaaatgctgataacgatactgtta ttggtgaaaaagtagttgcttatggtccgatttggcgcttattaaaagta cctgaaaatgttagtcatctaaaaattcaatttgtacctaaaaatgacgc aataacagatgcacgtggtatttatcaattacgagatggatataaatact atgactttgtagactcaatcggtcttcattctgggtcacatgtctatgtt gaaagacgtacaatggagccaacagcaacaaataataaagaatttacagt tacaacgtcattaaagaataatggtaactttggcgcttcattcaatacag atgattttgtatataaaattcaattacctgaaggtgttgaatatgtaaat aattcattgactaaagattttcctagcggtaattcaggtgttgatattaa tgatatgaatgtgacgtatgacgcagcaaatcgaattattacaattaaaa -continued

```
gtactggtggaggtacagggaattcgccggcacgactaatgcctgataaa
atattggatttgaagtataagctacgtgtgaacaatgtgccaacaccaag
aacagtaacatttaacgatacattaacgtataaaacatattcacaagatt
ttattaattcacctgctgaaagtcatactgtaagtacaaatccatataca
attgatatcatcatgaataaagacgcattgcaagccgaagtcgatagacg
aattcaacaagcggattatacatttgcatcattagatatttttaatgatc
ttaaaagacgcgcacaaacaattttagatgaaaaccgtaacaatgtacct
ttaaacaaaagagtttctcaagcagatatcgattcattagcaaatcagat
gcaacatacgttaattcgcagtgttgacgctgaaaatgccgttaatagaa
aagttgatgacatggaagatttagttaaccaaaatgatgaactgacagat
gaagaaaaacaagcagcgattcaagtcatcgaggaacataaaaatgaaat
tattgggaatattggtgaccaaacgactgatgatggcgttactagaatta
aagatcaaggtatacagactttaagtggagacactgcaacaccagttgtt
aaaccaaatgctaaacaagctatacgtgataaagcagcgaaacaaagaga
aattatcaatcacacgccagatgctactcaagatgaaattcaagatgcat
taaatcaattaacaacggatgaaacagatgctattgataatgttacgaat
gctactaccaatgctgatgttgaaacagctaaaaataatggtattaatac
aattggtgcagttgcgccacaagtgacacacaaacaagctgcaagagatg
caattaatcaagcgacagcaacgaaacgacaacaaataaatagcaataga
gaagcaacacaagaagagaaaaatgcagcattgaatgaattaacgcaagc
cacgaaccacgcattagaacaaatcaatcaagcgacaaccaatgatgatg
tagatactgccaaaggtgatggtctgaatgccattaatcctattgcgcct
gtaactgttgtcaagcaagcagcaagagatgccgtatcacatgatgcaca
acagcatatcgcagagatcaatgcaaatcctgatgcgactcaagaagaaa
gacaagcagcaatagagaaagtaaatgctgctgtagctgttgcgaatact
aatatattaaatgctaataccaatgctgatgttgagcaagtaaagacaaa
tgcaattcaaggtatacaagccattgaaccagctacaaaggttaaaacag
atgctaaaaacgctattgatcaaagtgcggaaacgcaacataatgcgata
tttaataataatgatgcgaccttagaagagcaacaagcagcacaacaatt
gcttgatcaagctgtagccacagcgaagcaaaatattaatgcagcagata
cgaatcaagaagttgcacaagcaaaagatcagggcacacaaaatatagtt
gtgattcaaccggcaacacaagttaaaacggatgcacgcaatgctgtaaa
tgaaaaagcgcgagaggcgataacaaatatcaatgctacacctggcgcga
ctcgagaagagaaacaagaagcgataaatcgtgtcaatacacttaaaaat
agagcattaaatgatattggtgtgacgtctactactgcgatggtcaatag
tattagagacgatgcagtcaatcaaatcggtgcagttcaaccgcatgtaa
cgaagaaacaaactgctacaggtgtattaacggacttagcaactgcaaaa
aaacaagaaattaatcaaaatacaaatgcaaccactgaagaaaagcaagt
agcattaaatcaagtagaccaagatttagcaacggcaattaataatataa
atcaagctgatactaatgcagaagtagatcaagcacaacaattaggtaca
```

-continued

```
aaagcaattaatgcgattcagccaaatattgtaaaaaaacctgcagcatt
agcacaaaccaatcagcattatagtgctaaattagttgaaatcaatgcta
caccagatgcaacagatgatgagaaaaatgctgcgatcaatactttaaat
caagacagacaacaagctattgaaagtattaaacaagcaaatacaaatgc
ggaagtagaccaagctgcgacagtggcagagaataatatcgatgctgttc
aagttgacgttgtaaaaaaacaagcagcgcgagataaaatcactgctgaa
gtagcgaagcgtattgaagcggttaaacaaacacctaatgcaactgacga
agaaaagcaggctgcagttaatcaaatcaatcaacttaaagatcaagcgt
ttaatcaaattaatcaaaaccaaacaaatgatcaggtagacgcaactaca
aatcaagcgattaatgctatagataatgttgaagctgaagtagtaattaa
accaaaggcaattgcagatattgaaaaagctgttaaagaaaagcaacagc
aaattgataatagtcttgattcaacagataatgagaaagaagttgcttta
caagcattagctaaagaaaaagaaaaagcacttgcagctattgaccaagc
tcaaacgaatagtcaggtgaatcaagcggcaacaaatggtgtatcagcga
ttaaaattattcaacctgaaacaaaaattaaaccagcagcacgtgaaaaa
atcaatcaaaaagcgaatgaattacgtgcgcaaattaatcaagataaaga
agcgacagcagaagaaagacaagcggcgttagataaaatcaatgatttag
ttgctaaagctatgacaaatatcacgaatgatagaacaaatcagcaagtt
aatgactcaacaaatcaagcgcttgacgacattgcattagtgacgcctga
ccatattgttagagcagctgctagagatgcagttaagcaacaatatgaag
ctaaaaagcacgaaattgagcaagcggaacatgcgactgatgaagaaaaa
caagttgctttaaatcaattagcgaataatgaaaaacgtgcattacaaaa
cattaatcaagcaatagcgaataatgatgtgaaacgtgttgaatcaaatg
gtattgctacgttaaaaggcgtagaaccgcacattgtggttaaacctgaa
gctcaagaagccataaaagcgagcgcagataaccaagtagaatctataaa
agatacaccacatgctacgacagatgaattagatgaagcaaaccaacaaa
taaacgacacacttaaacaaggtcaacaagatatagacaatacgacacaa
gatgcagctgtcaatgatgttagaaaccaaacgattaaggcaatcgaaca
aattaaaccgaaagttagacgcaaacgtgcagcgttggataacattgatg
aaagtaataataatcaactcgatgcaatacgaaatacgctagatacaacg
caagatgaacgaaatgttgctattgctgcgttaaataaaattgttaatgc
aattaaaaatgatattgcacaaaacaaaacgaatgcagaagtggatcaaa
ctgaggctgatggtaacaacaacatcaaagtgattttacctaaagttcaa
gttaaaccagcagcgcgtcaatctgtcagcgcaaaagctgaagctcaaaa
tgcacttattgatcaaagtgatttatctaccgaagaagaaagattagctg
ctaaacatttagtagaacaagcacttaatcaagctattgatcagatcaat
cacgcagataagactgcgcaagttaatcaaaatagtatcgatgctcaaaa
tattatttcaaaaattaaaccagcgacaacagttaaagcaacagcattac
aacaaattcaaaatatcgctacaaataaaattaattttaattaaagcaaat
aacgaagcgacagatgaagaacaaaatgctgcaatagtacaagttgaaaa
agagttaattaaagctaaacaacaaattgctggtgcagtgactaatgctg
```

-continued

```
atgtggcatatttattgcatgatgggaaaaacgaaattcgtgaaatcgaa
cctgttattaataaaaaagcaactgcgcgagaacaattaacaacattatt
caacgataagaaacaagcaattgaagcgaatgttcaagcaacagtagaag
aaagaaatagtattttagcacagttacaaaacatttatgacactgctatt
ggacaaattgatcaagatcgtagcaatgcacaagttgataaaacagcaac
attaaatctacaaacaatacatgatttagacgtacatcctattaaaaagc
cagatgctgaaaaaacgattaatgatgatcttgcacgtgttacacattta
gtgcaaaattatcgaaaagtaagtgatcgtaataaggctgatgcattaaa
agctataactgcattaaaattacaaatggatgaagaattaaaaacagcac
gcactaatgctgatgttgatgcagttttaaaacgatttaatgttgcatta
ggcgatatagaagcagtaattactgaaaaagaaaatagcttactgcgcat
tgataacattgctcaacaaacatgcgaaattcaaagcgatcgcaaacac
cagaacaattagctaaagtaaaagcattaattgatcaatatgttgcagat
ggcaatagaatggttgatgaagatgcgacattaaatgacatcaaaaaaga
tacgcaactcattattgatgaaattttagcaattaaattacctgctgaag
tgataaaagcgtcaccaaaagtggggcaacctgctccaaaagtttgtacg
cctattaaaaagaagataaacaagaagtgcgaaaagttgtaaaagaact
tccaaatactggttctgaagaaatggatttaccattaaaagaattagcac
taattacaggcgcagcattattagctagaagacgttctaaaaaagaaaaa
gaatcataa
```

EkeS_MRSA
(SEQ ID NO: 2)

```
MNLLKKNKYSIRKYKVGIFSTLIGTVLLLSNPNGAQALTTDHNVQGGSNQ
ALPGNSQNTNADTNRDIVNDSQNTPNAHATDNTSTNQALTNHQNVDVANQ
VGPAPIQPSASPAQNNNNSNANSTATEPAANTNNNLASNNNTLNVPNNTD
NNDSARHLTLKEIQEDVRHSSDKPELVAIAEEASNRPKKRSRRAAPTDPN
ATPADPTATPADPTAGNGSAPVAITAPYTPTTDPNANNIGQNAPNEVLSF
DDNNIRPSTNRSVPTVTVVDNLPGYTLINGGKVGVFSHAMVRTSMFDSGD
AKNYQAQGNVIALGRIRGNDTNDHGDFNGIEKTLTVNPNSELIFEFNTMT
TKNYQGMTNLIIKNADNDTVIGEKVVAYGPIWRLLKVPENVSHLKIQFVP
KNDAITDARGIYQLRDGYKYYDFVDSIGLHSGSHVYVERRTMEPTATNNK
EFTVTTSLKNNGNFGASFNTDDFVYKIQLPEGVEYVNNSLTKDFPSGNSG
VDINDMNVTYDAANRIITIKSTGGGTGNSPARLMPDKILDLKYKLRVNNV
PTPRTVTFNDTLTYKTYSQDFINSPAESHTVSTNPYTIDIIMNKDALQAE
VDRRIQQADYTFASLDIFNDLKRRAQTILDENRNNVPLNKRVSQADIDSL
ANQMQHTLIRSVDAENAVNRKVDDMEDLVNQNDELTDEEKQAAIQVIEEH
KNEIIGNIGDQTTDDGVTRIKDQGIQTLSGDTATPVVKPNAKQAIRDKAA
KQREINHTPDATQDEIQDALNQLTTDETDAIDNVTNATTNADVETAKNNG
INTIGAVAPQVTHKQAARDAINQATATKRQQINSNREATQEEKNAALNEL
TQATNHALEQINQATTNDDVDTAKGDGLNAINPIAPVTVVKQAARDAVSH
DAQQHIAEINANPDATQEERQAAIEKVYAAVAVANTNILNANTNADVEQV
KTNAIQGIQAIEPATKVKTDAKNAIDQSAETQHNAIFNNNDATLEEQQAA
QQLLDQAVATAKQNINAADTNQEVAQAKDQGTQNIVVIQPATQVKTDARN
AVNEKAREAITNINATPGATREEKQEAINRVNTLKNRALNDIGVTSTTAM
VNSIRDDAVNQIGAVQPHVTKKQTATGVLTDLATAKKQEINQNTNATTEE
KQVALNQVDQDLATAINNINQADTNAEVDQAQQLGTKAINAIQPNIVKKP
AALAQTNQHYSAKLVEINATPDATDDEKNAAINTLNQDRQQAIESIKQAN
TNAEVDQAATVAENNIDAVQVDVVKKQAARDKITAEVAKRIEAVKQTPNA
TDEEKQAAVNQINQLKDQAFNQINQNQTNDQVDATTNQAINAIDNVEAEV
VIKPKAIADIEKAVKEKQQQIDNSLDSTDNEKEVALQALAKEKEKALAAI
DQAQTNSQVNQAATNGVSAIKIIQPETKIKPAAREKINQKANELRAQINQ
DKEATAEERQAALDKINDLVAKAMTNITNDRTNQQVNDSTNQALDDIALV
TPDHIVRAAARDAVKQQYEAKKHEIEQAEHATDEEKQVALNQLANNEKRA
LQNINQAIANNDVKRVESNGIATLKGVEPHIVVKPEAQEAIKASADNQVE
SIKDTPHATTDELDEANQQINDTLKQGQQDIDNTTQDAAVNDVRNQTIKA
IEQIKPKVRRKRAALDNIDESNNNQLDAIRNTLDTTQDERNVAIAALNKI
VNAIKNDIAQNKTNAEVDQTEADGNNNIKVILPKVQVKPAARQSVSAKAE
AQNALIDQSDLSTEEERLAAKHLVEQALNQAIDQINHADKTAQVNQNSID
AQNIISKIKPATTVKATALQQIQNIATNKINLIKANNEATDEEQNAAIVQ
VEKELIKAKQQIAGAVTNADVAYLLHDGKNEIREIEPVINKKATAREQLT
TLFNDKKQAIEANVQATVEERNSILAQLQNIYDTAIGQIDQDRSNAQVDK
TATLNLQTIHDLDVHPIKKPDAEKTINDDLARVTHLVQNYRKVSDRNKAD
ALKAITALKLQMDEELKTARTNADVDAVLKRFNVALGDIEAVITEKENSL
LRIDNIAQQTYAKFKAIATPEQLAKVKALIDQYVADGNRMVDEDATLNDI
KKDTQLIIDEILAIKLPAEVIKASPKVGQPAPKVCTPIKKEDKQEVRKVV
KELPNTGSEEMDLPLKELALITGAALLARRRSKKEKES
```

DsqA (8325)
(SEQ ID NO: 3)

```
tctaatgaatgtaaagataatacaaggagttattacatgagtaaaagaca
gaaagcatttcatgacagcttagcaaacgaaaaaacaagagtaagacttt
ataaatctggaaaaaattgggtaaaatccggaattaaagaaatagaaatg
ttcaaaattatgggctaccatttattagtcatagtttagtgagtcaaga
taatcaaagcattagtaaaaaatgacgggatacggactgaaaactacgg
cggttattggtggtgcattcacggtaaatatgttgcatgaccagcaagct
tttgcggcttctgatgcaccattaacttctgaattaaacacacaaagtga
aacagtaggtaatcaaaactcaacgacaatcgaagcatcaacatcaacag
ccgattccacaagtgtaacgaaaaatagtagttcggtacaaacatcaaat
agtgacacagtctcaagtgaaaagtctgaaaaggtcacttcgacaactaa
tagtacaagcaatcaacaagagaaattgacatctacatcagaatcaacat
cctcaaagaatactacatcaagttctgatactaaatctgtagcttcaact
tcaagtacagaacaaccaattaatacatcaacaaatcaaagtactgcatc
aaataaacttcacaaagcacaacgccatcttcggtcaacttaaacaaaa
ctagcacaacgtcaactagcaccgcaccagtaaaaacttcgaactttcagt
```

-continued cgcttagctatgtcaacatttgcgtcagcagcgacgacaaccgcagtaac
tgctaatacaattacagttaataaagataacttaaaacaatatatgacaa
cgtcaggtaatgctacctatgatcaaagtaccggtattgtgacgttaaca
caggatgcatacagccaaaaggtgctattacattaggaacacgtattga
ctctaataagagttttcattttctggaaaagtaaatttaggtaacaaat
atgaagggcatggaaatggtggagatggtatcggttttgccttttcacca
ggtgtattaggtgaaacagggttaaacggtgccgcagtaggtattggtgg
cttaagtaacgcatttggcttcaaattggatacgtatcacaatacatcta
aaccaaattcagctgcaaaggcgaatgctgacccatctaatgtagctggt
ggaggtgcgtttggtgcatttgtaacaacagatagttatggtgttgcgac
aacgtatacatcaagttcaacagctgataatgctgcgaagttaaatgttc
aacctacaaataacacgttccaagattttgatattaactataatggtgat
acaaaggttatgactgtcaaatatgcaggtcaaacatggacacgtaatat
ttcagattggattgcgaaaagtggtacgaccaacttttcattatcaatga
cagcctcaacaggtggcgcgacaaatttacaacaagtacaatttggaaca
ttcgaatatacagagtctgctgttacacaagtgagatacgttgatgtaac
aacaggtaaagatattattccaccaaaaacatattcaggaaatgttgatc
aagtcgtgacaatcgataatcagcaatctgcattgactgctaaaggatat
aactacacgtccgtcgatagttcatatgcgtcaacttataatgatacaaa
taaaactgtaaaaatgacgaatgctggacaatcagtgacatattatttta
ctgatgtaaaagcaccaactgtaactgtaggcaatcaaaccatagaagtg
ggtaaaacaatgaatcctattgtattgactacaacgataatggtactgg
gactgtgacaaatacagttacaggattaccaagcggattaagttacgata
gtgcaacgaattcaatcattgggacaccaacaaaaattggtcaatcaaca
gtgacagttgtgtctactgaccaagcaaataacaaatcgacgacaacttt
tacaataaatgttgtggatacgacagcaccaacagtgacaccaataggag
atcaatcatcagaagtgtattcaccaatatccccgattaaaattgctacg
caagataacagtggaaatgcggtgacgaatacagtgactggattgccatc
cggactaacatttgatagtacaaataatactattagtggtacaccaacaa
acattggtacaagtactatatcaatcgtttctacagatgcgagcggtaac
aaaacgacgacaacttttaaatatgaagtaacaagaaatagcatgagtga
ttccgtatcaacatcaggaagtacacaacaatctcaaagtgtgtcaacaa
gtaaagctgactcacaaagtgcatcaacgagtacatcaggatcgattgtg
gtatctacatcagctagtacctcgaaatcgacaagtgtaagcctatctga
ttctgtgagtgcatctaagtcattaagcacatctgaaagtaatagtgtat
caagctcaacaagcacaagtttagtgaattcacaaagtgtatcatcaagc
atgtcggattcagctagtaaatcaacatcattaagcgattctatttcaaa
ctctagcagtactgaaaaatccgaaagtctatcaacaagtacatctgatt
cattgcgtacatcaacatcactcagtgactcattaagtatgagtacatca
ggaagcttgtctaagtcacaaagcttatcaacgagtatatcagggtcgtc -continued tagtacatcagcatcattaagtgacagtacatcgaatgcaattagtacat
caacatcattgagcgagtcagctagcacctcggactctatcagtatttca
aatagcatagccaactctcaaagtgcgtcaacaagcaaatcagattcaca
aagtacatcaatatcattaagtacaagtgattcaaaatcgatgagtacat
cagaatcattgagcgattcgacgagcacaagtggttctgtttctggatca
ctaagcatagcagcatcacaaagtgtctcaacaagtacatcagactcgat
gagtacttcagagatagtaagtgactctatcagtacaagtgggtcattat
ctgcatcagacagtaaatcaatgtccgtaagtagttcaatgagcacgtct
cagtcaggtagtacatcagaatcattaagtgattcacaaagtacatctga
ttctgatagtaagtcattatcacaaagtactagtcaatcaggttcaacaa
gtacatcaacgtcgacaagtgcttcagtacgtacttcggaatcacaaagt
acgtctggttcaatgagtgcaagtcaatccgattcaatgagcatatcaac
gtcgtttagtgattcaacgagtgatagcaaatcagcatcaactgcatcaa
gtgaatcaatatcacaaagtgcttctacgagcacatctggttcggtaagt
acttcgacatcgttaagtacaagtaattcagaacgtacatcaacatctat
gagtgattccacaagcttaagtacatcagagtctgattcaataagtgaat
caacgtcaacgagcgactctataagtgaagcaatatctgcttcagagagc
acgtttatatcattaagtgaatcaaatagtactagcgattcagaatcaca
aagtgcatctgccttttaagtgaatcattaagtgaaagtacgtctgaat
caacatcagagtcagtgagtagttcgacaagtgagagtacgtcattatca
gacagtacatcagaatctggtagcacatcaacatcattaagtaattcaac
aagtggtagtacgtccatttcaacatcgacaagtatcagtgaatcaacgt
caacgtttaagagcgagagtgtttcaacatcactgagtatgtcaacgagt
acaagtttgtctgactctacaagtttgtcaacatcattaagtgattccac
aagtgatagtaagtctgattcattaagtacatcaatgtcgacaagtgatt
caatcagtacaagtaaatctgattccattagtacatccacatcattaagt
ggttctacaagtgaaagtgaatccgactcaacatcatcaagtgaaagtaa
atccgattcaacatcaatgagcataagtatgtctcaatcaacatcaggaa
gtacaagtacgtcaacgagtacaagtttgtctgactcaacgagtacatca
ttgtcactaagtgcctcaatgaatcaaagcggagtagactcaaactcagc
aagccaaagtgcctcaaactcaacaagtacaagcacgagcgaatccgatt
cacaaagcacatcatcatatacaagtcagtcaacaagccaaagtgaatcc
acatcgacatcaacgtcactaagcgattcaacaagtatatctaaaagtac
gagtcaatcaggttcggtaagcacatcagcgtcattaagtggttcagaga
gtgaatctgattcacaaagtatctcaacaagtgcaagtgagtcaacatca
gaaagtgcgtcaacatcactcagtgactcaacaagtacaagtaactcagg
atcagcaagtacgtcaacatcgctcagtaactcagcaagcgcaagtgaat
ccgatttgtcgtcaacatctttaagtgattcaacatctgcgtcaatgcaa
agcagtgaatccgattcacaaagcacatcagcatcattaagtgattcgct
aagtacatcaacttcaaaccgcatgtcgaccattgcaagtttatctacat
cggtaagtacatcagagtctggctcaacatcagaaagtacaagtgaatcc -continued

```
gattcaacatcaacatcattaagcgattcacaaagcacatcaagaagtac
aagtgcatcaggatcagcaagtacatcaacatcaacaagtgactctcgta
gtacatcagcttcaactagtacttcgatgcgtacaagtactagtgattca
caaagtatgtcgctttcgacaagtacatcaacaagtatgagtgattcaac
gtcattatctgatagtgttagtgattcaacatcagactcaacaagtgcga
gtacatctggttcgatgagtgtgtctatatcgttaagtgattcgacaagt
acatcaacatcggctagtgaagtaatgagcgcaagcatatctgattcaca
aagtatgtcagaatctgtaaatgattcagaaagtgtaagtgaatctaatt
ctgaaagtgactctaaatcgatgagtggctcaacaagtgtcagtgattct
ggctcattgagcgtctcaacgtcattaagaaaatcagaaagtgtaagcga
gtcaagttcattgagttgctcacaatcgatgagcgattcagtaagcacaa
gcgattcgtcatcattaagtgtatcgacgtcactaagaagttcagaaagc
gtgagtgaatctgattcattaagtgattcaaaatcaacaagtggttcgac
ttcaacaagtacatctggttcattgagtacctcaacatcattaagtggtt
cagaaagcgtaagcgagtctacctcgctaagtgattcaatatcaatgagt
gattctactagtacaagtgactccgactcattaagtggatcaatatctt
aagtggttccacaagtcttagcacttcggattcattaagtgattcaaaat
cattgagtagctcgcaaagtatgagtggatcagaatcaacgtcaacaagt
gtgagcgattcgcagtcaagctcaacaagtaatagtcaatttgactctat
gagcatcagtgcatcagaaagcgactcaatgtctacaagtgattcgtcta
gcatcagtggatcaaattcaacgagtacatcactttcaacatctgactca
atgagcggaagcgtatcagtttcaacatcgacaagtttaagtgactcaat
atcaggttcaacaagtgtaagtgactcgagctcaacaagcacatctacat
cattaagtgattcaatgtcacaaagccagtcaacaagtacaagtgcatct
ggttccttaagtacatcgatatcaacatcaatgtcaatgagtgctagtac
atcgtcatcacaaagcacatcggtgtcgacatcattatcaacatcagaca
gtatcagtgattctacttcaataagtatcagtggttcacaaagtacagta
gaatcagaatctacaagtgattcaacttctatcagtgactcagaatcatt
gagtacatcagattcagactcgactcgacaagtacatcggactcaacaa
gtggttcaacttcaacaagcatatctgaatcattaagtacgtctggttca
ggttcaacgagcgtatctgactcaacatcaatgagtgaatctaattcatc
gagtgtttcaatgtcacaagacaaatccgactcaacatcaattagtgact
cagaatcagtgtcaacaagcacatcaacgtcattgagcacatccgattcg
acaagcacatccgaatcactgagtacatctatgtctggttcacaaagcat
ttctgactcaacatcaacaagtatgtccggctcaacaagtacatctgaat
ctaactcaatgcatccgtcagactcaatgagtatgcatcatactcacagc
acgagcacatctcgcttatcaagtgaagcaacaacgagcacgagtgaatc
tcagtctacattaagtgcaacatctgaagtgactaaacataatggcacac
cagcacaaagtgaaaaaagattgccagatacaggtgactcaataaaacaa
aatggattactaggtggcgttatgacattattagttggtttaggtttaat
gaagagaaagaaaaagaaagatgaaaatgatcaagatgattctcaagcat
aa
```

DsqA (8325) (SEQ ID NO: 4)

SNECKDNTRSYYMSKRQKAFHDSLANEKTRVRLYKSGKNWVKSGIKEIEM
FKIMGLPFISHSLVSQDNQSISKKMTGYGLKTTAVIGGAFTVNMLHDQQA
FAASDAPLTSELNTQSETVGNQNSTTIEASTSTADSTSVTKNSSSVQTSN
SDTVSSEKSEKVTSTTNSTSNQQEKLTSTSESTSSKNTTSSSDTKSVAST
SSTEQPINTSTNQSTASNNTSQSTTPSSVNLNKTSTTSTSTAPVKLRTFS
RLAMSTFASAATTTAVTANTITVNKDNLKQYMTTSGNATYDQSTGIVTLT
QDAYSQKGAITLGTRIDSNKSFHFSGKVNLGNKYEGHGNGGDGIGFAFSP
GVLGETGLNGAAVGIGGLSNAFGFKLDTYHNTSKPNSAAKANADPSNVAG
GGAFGAFVTTDSYGVATTYTSSSTADNAAKLNVQPTNNTFQDFDINYNGD
TKVMTVKYAGQTWTRNISDWIAKSGTTNFSLSMTASTGGATNLQQVQFGT
FEYTESAVTQVRYVDVTTGKDIIPPKTYSGNVDQVVTIDNQQSALTAKGY
NYTSVDSSYASTYNDTNKTVKMTNAGQSVTYYFTDVKAPTVTVGNQTIEV
GKTMNPIVLTTTDNGTGTVTNTVTGLPSGLSYDSATNSIIGTPTKIGQST
VTVVSTDQANNKSTTTFTINVVDTTAPTVTPIGDQSSEVYSPISPIKIAT
QDNSGNAVTNTVTGLPSGLTFDSTNNTISGTPTNIGTSTISIVSTDASGN
KTTTTFKYEVTRNSMSDSVSTSGSTQQSQSVSTSKADSQSASTSTSGSIV
VSTSASTSKSTSVSLSDSVSASKSLSTSESNSVSSSTSTSLVNSQSVSSS
MSDSASKSTSLSDSISNSSSTEKSESLSTSTSDSLRTSTSLSDSLSMSTS
GSLSKSQSLSTSISGSSSTSASLSDSTSNAISTSTSLSESASTSDSISIS
NSIANSQSASTSKSDSQSTSISLSTSDSKSMSTSESLSDSTSTSGSVSGS
LSIAASQSVSTSTSDSMSTSEIVSDSISTSGSLSASDSKSMSVSSSMSTS
QSGSTSESLSDSQSTSDSDKSLSQSTSQSGSTSTSTSASVRTSESQS
TSGSMSASQSDSMSISTSFSDSTSDSKSASTASSESISQSASTSTSGSVS
TSTSLSTSNSERTSTSMSDSTSLSTSESDSISESTSTSDSISEAISASES
TFISLSESNSTSDSESQSASAFLSESLSESTSESTSESVSSSTSESTSLS
DSTSESGSTSTSLSNSTSGSTSISTSTSISESTSTFKSESVSTSLSMSTS
TSLSDSTSLSTSLSDSTSDSKSDSLSTSMSTSDSISTSKSDSISTSTSLS
GSTSESESDSTSSSESKSDSTSMSISMSQSTSGSTSTSTSLSDSTSTS
LSLSASMNQSGVDSNSASQSASNSTSTSTSESDSQSTSSYTSQSTSQSES
TSTSTSLSDSTSISIKSTSQSGSVSTSASLSGSESESDSQSISTSASESTS
ESASTSLSDSTSTSNSGSASTSTSLSNSASASESDLSSTSLSDSTSASMQ
SSESDSQSTSASLSDSLSTSTSNRMSTIASLSTSVSTSESGSTSESTSES
DSTSTSLSDSQSTSRSTSASGSASTSTSTSDSRSTSASTSTSMRTSTSDS
QSMSLSTSTSTSMSDSTSLSDSVSDSTSDSTSASTSGSMSVSISLSDSTS
TSTSASEVMSASISDSQSMSESVNDSESVSESNSESDSKSMSGSTSVSDS
GSLSVSTSLRKSESVSESSSLSGSQSMSDSVSTSDSSSLSVSTSLRSSES
VSESDSLSDSKSTSGSTSTSTSGSLSTSTSLSGSESVSESTSLSDSISMS

DSTSTSDSDSLSGSISLSGSTSLSTSDSLSDSKSLSSSQSMSGSESTSTS
VSDSQSSSTSNSQFDSMSISASESDSMSTSDSSSISGSNSTSTSLSTSDS
MSGSVSVSTSTSLSDSISGSTSVSDSSSTSTSTSLSDSMSQSQSTSTSAS
GSLSTSISTSMSMSASTSSSQSTSVSTSLSTSDSISDSTSISISGSQSTV
ESESTSDSTSISDSESLSTSDSDTSTSTSDSTSGSTSTSISESLSTSGS
GSTSVSDSTSMSESNSSSVSMSQDKSDSTSISDSESVSTSTSTSLSTSDS
TSTSESLSTSMSGSQSISDSTSTSMSGSTSTSESNSMHPSDSMSMHHTHS
TSTSRLSSEATTSTSESQSTLSATSEVTKHNGTPAQSEKRLPDTGDSIKQ
NGLLGGVMTLLVGLGLMKRKKKKDENDQDDSQA

KesK1 (8325)
(SEQ ID NO: 5)
ttattatcaattaaatataatcttataggagttgttaacaacatgaacaa
acatcacccaaaattaaggtctttctattctattagaaaatcaactctag
gcgttgcatcggtcattgtcagtacactattttaattacttctcaacat
caagcacaagcagcagaaaatacaaatacttcagataaaatctcggaaaa
tcaaaataataatgcaactacaactcagccacctaaggatacaaatcaaa
cacaacctgctacgcaaccagcaaacactgcgaaaaactatcctgcagcg
gatgaatcacttaaagatgcaattaaagatcctgcattagaaaataaaga
acatgatataggtccaagagaacaagtcaatttccagttattagataaaa
acaatgaaacgcagtactatcacttttcagcatcaaagatccagcagat
gtgtattacactaaaaagaaagcagaagttgaattagacatcaatactgc
ttcaacatggaagaagtttgaagtctatgaaaacaatcaaaaattgccag
tgagacttgtatcatatagtcctgtaccagaagaccatgcctatattcga
ttcccagtttcagatggcacacaagaattgaaaattgtttcttcgactca
aattgatgatggagaagaaacaaattatgattatactaaattagtatttg
ctaaacctatttataacgatccttcacttgtaaaatcagatacaaatgat
gcagtagtaacgaatgatcaatcaagttcagtcgcaagtaatcaaacaaa
cacgaatacatctaatcaaaatatatcaacgatcaacaatgctaataatc
aaccgcaggcaaccgaccaatatgagtcaacctgcacaaccaaaatcgtca
acgaatgcagatcaagcgtcaagccaaccagctcatgaaacaaattctaa
tggtaatactaacgataaaacgaatgagtcaagtaatcagtcggatgtta
atcaacagtatccaccagcagatgaatcactacaagatgcaattaaaaac
ccggctatcatcgataaagaacatacagctgataattggcgaccaattga
ttttcaaatgaaaaatgataaaggtgaaagacagttctatcattatgcta
gtactgttgaaccagcaactgtcattttttacaaaaacaggaccaataatt
gaattaggtttaaagacagcttcaacatggaagaaatttgaagtttatga
aggtgacaaaaagttaccagtcgaattagtatcatatgattctgataaag
attatgcctatattcgtttcccagtatctaatggtacgagagaagttaaa
attgtgtcatctattgaatatggtgagaacatccatgaagactatgatta
tacgctaatggtctttgcacagcctattactaataacccagacgactatg
tggatgaagaaacatacaatttacaaaaattattagctccgtatcacaaa gctaaaacgttagaaagacaagtttatgaattagaaaaattacaagagaa
attgccagaaaatataaggcggaatataaaaagaaattagatcaaacta
gagtagagttagctgatcaagttaaatcagcagtgacggaatttgaaaat
gttacacctacaaatgatcaattaacagatttacaagaagcgcatttttgt
tgtttttgaaagtgaagaaaatagtgagtcagttatggacggctttgttg
aacatccattctatacagcaactttaaatggtcaaaaatatgtagtgatg
aaaacaaaggatgacagttactggaaagatttaattgtagaaggtaaacg
tgtcactactgtttctaaagatcctaaaaataattctagaacgctgattt
tcccatatatacctgacaaagcagtttacaatgcgattgttaaagtcgtt
gtggcaaacattggttatgaaggtcaatatcatgtcagaattataaatca
ggatatcaatacaaaagatgatgatacatcacaaaataacacgagtgaac
cgctaaatgtacaaacaggacaagaaggtaaggttgctgatacagatgta
gctgaaaatagcagcactgcaacaaatcctaaagatgcgtctgataaagc
agatgtgatagaaccagagtctgacgtggttaaagatgctgataataata
ttgataaagatgtgcaacatgatgttgatcatttatccgatatgtcggat
aataatcacttcgataaatatgatttaaaagaaatggatactcaaattgc
caaagatactgatagaaatgtggataaagatgccgataatagcgttggta
tgtcatctaatgtcgatactgataaagactctaataaaaataaagacaaa
gtcatacagctgaatcatattgccgataaaataatcatactggaaaagc
agcaaagcttgacgtagtgaaacaaaattataataatacagacaaagtta
ctgacaaaaaaacaactgaacatctgccgagtgatattcataaaactgta
gataaaacagtgaaaacaaaagaaaagccggcacaccatcgaaagaaaa
caaacttagtcaatctaaaatgctaccaaaaactggagaaacaacttcaa
gccaatcatggtggggcttatatgcgttattaggtatgttagctttattc
attcctaaattcagaaaagaatctaaataa KesK1 (8325)
(SEQ ID NO: 6)
LLSIKYNLIGVVNNMNKHHPKLRSFYSIRKSTLGVASVIVSTLFLITSQH
QAQAAENTNTSDKISENQNNNATTTQPPKDTNQTQPATQPANTAKNYPAA
DESLKDAIKDPALENKEHDIGPREQVNFQLLDKNNETQYYHFFSIKDPAD
VYYTKKKAEVELDINTASTWKKFEVYENNQKLPVRLVSYSPVPEDHAYIR
FPVSDGTQELKIVSSTQIDDGEETNYDYTKLVFAKPIYNDPSLVKSDTND
AVVTNDQSSSVASNQTNTNTSNQNISTINNANNQPQATTNMSQPAQPKSS
TNADQASSQPAHETNSNGNTNDKTNESSNQSDVNQQYPPADESLQDAIKN
PAIIDKEHTADNWRPIDFQMKNDKGERQFYHYASTVEPATVIFTKTGPII
ELGLKTASTWKKFEVYEGDKKLPVELVSYDSDKDYAYIRFPVSNGTREVK
IVSSIEYGENIHEDYDYTLMVFAQPITNNPDDYVDEETYNLQKLLAPYHK
AKTLERQVYELEKLQEKLPEKYKAEYKKKLDQTRVELADQVKSAVTEFEN
VTPTNDQLTDLQEAHFVVFESEENSESVMDGFVEHPFYTATLNGQKYVVM
KTKDDSYWKDLIVEGKRVTTVSKDPKNNSRTLIFPYIPDKAVYNAIVKVV
VANIGYEGQYHVRIINQDINTKDDDTSQNNTSEPLNVQTGQEGKVADTDV
AENSSTATNPKDASDKADVIEPESDVVKDADNNIDKDVQHDVDHLSDMSD -continued NNHFDKYDLKEMDTQIAKDTDRNVDKDADNSVGMSSNVDTDKDSNKNKDK
VIQLNHIADKNNHTGKAAKLDVVKQNYNNTDKVTDKKTTEHLPSDIHKTV
DKTVKTKEKAGTPSKENKLSQSKMLPKTGETTSSQSWWGLYALLGMLALF
IPKFRKESK KrkN2 (8325)
(SEQ ID NO: 7)
gaggaaaacaacatgacaaaacattatttaaacagtaagtatcaatcaga
acaacgttcatcagctatgaaaaagattacaatgggtacagcatctatca
ttttaggttccttgtatacataggcgcagacagccaacaagtcaatgcg
gcaacagaagctacgaacgcaactaataatcaaagcacacaagtttctca
agcaacatcacaaccaattaatttccaagtgcaaaaagatggctcttcag
agaagtcacacatggatgactatatgcaacaccctggtaaagtaattaaa
caaaataataaatattatttccaaaccgtgttaaacaatgcatcattctg
gaaagaatacaaattttacaatgcaaacaatcaagaattagcaacaactg
ttgttaacgataataaaaaagcggatactagaacaatcaatgttgcagtt
gaacctggatataagagcttaactactaaagtacatattgtcgtgccaca
aattaattacaatcatagatatactacgcatttggaatttgaaaaagcaa
ttcctacattagctgacgcagcaaaaccaaacaatgttaaaccggttcaa
ccaaaaccagctcaacctaaaacacctactgagcaaactaaaccagttca
acctaaagttgaaaaagttaaacctactgtaactacaacaagcaaagttg
aagacaatcactctactaaagttgtaagtactgacacaacaaaagatcaa
actaaaacacaaactgctcatacagttaaaacagcacaaactgctcaaga
acaaaataaagttcaaacacctgttaaagatgttgcaacagcgaaatctg
aaagcaacaatcaagctgtaagtgataataaatcacaacaaactaacaaa
gttacaaaacataacgaaacgcctaaacaagcatctaaagctaaagaatt
accaaaaactggtttaacttcagttgataactttattagcacagttgcct
tcgcaacacttgccctttaggttcattatctttattacttttcaaagaa
aaagaatctaaataa KrkN2 (8325)
(SEQ ID NO: 8)
EENNMTKHYLNSKYQSEQRSSAMKKITMGTASIILGSLVYIGADSQQVNA
ATEATNATNNQSTQVSQATSQPINFQVQKDGSSEKSHMDDYMQHPGKVIK
QNNKYYFQTVLNNASFWKEYKFYNANNQELATTVVNDNKKADTRTINVAV
EPGYKSLTTKVHIVVPQINYNHRYTTHLEFEKAIPTLADAAKPNNVKPVQ
PKPAQPKTPTEQTKPVQPKVEKVKPTVTTTSKVEDNHSTKVVSTDTTKDQ
TKTQTAHTVKTAQTAQEQNKVQTPVKDVATAKSESNNQAVSDNKSQQTNK
VTKHNETPKQASKAKELPKTGLTSVDNFISTVAFATLALLGSLSLLLFKR
KESK KrkN (8325)
(SEQ ID NO: 9)
tatacaattaggagttgtttctacaacatgaacaaacagcaaaaagaatt
taaatcattttattcaattagaaagtcatcactaggcgttgcatctgtag
caattagtcactttattattaatgtcaatggcgaagcacaagcagca
gctgaagaaacaggtggtacaaatacagaagcacaaccaaaaactgaagc
agttgcaagtccaacaacaacatctgaaaaagctccagaaactaaaccag
tagctaatgctgtctcagtatctaataaagaagttgaggcccctacttct
gaaacaaaagaagctaaagaagttaaagaagttaaagcccctaaggaaac
aaaagaagttaaaccagcagcaaaagccactaacaatacatatcctattt
tgaatcaggaacttagagaagcgattaaaaaccctgcaataaaagacaaa
gatcatagcgcaccaaactctcgtccaattgattttgaaatgaaaaagaa
agatggaactcaacagttttatcattatgcaagttctgttaaacctgcta
gagttattttcactgattcaaaaccagaaattgaattaggattacaatca
ggtcaatttggagaaaatttgaagtttatgaaggtgacaaaaagttgcc
aattaaattagtatcatacgactgttaaagattatgcttacattcgct
tctctgtatcaaacggaacaaaagctgttaaaattgttagttcaacacac
ttcaataacaaagaagaaaaatacgattacacattaatggaattcgcaca
accaatttataacagtgcagataaattcaaaactgaagaagattataaag
ctgaaaaattattagcgccatataaaaagcgaaaacactagaaagacaa
gtttatgaattaaataaaattcaagataaacttcctgaaaaattaaaggc
tgagtacaagaagaaattagaggatacaaagaaagctttagatgagcaag
tgaaatcagctattactgaattccaaaatgtacaaccaacaaatgaaaaa
atgactgatttacaagatacaaaatatgttgtttatgaaagtgttgagaa
taacgaatctatgatggatacttttgttaaacaccctattaaaacaggta
tgcttaacggcaaaaaatatatggtcatggaaactactaatgacgattac
tggaaagatttcatggttgaaggtcaacgtgttagaactataagcaaaga
tgctaaaaataatactagaacaattattttcccatatgttgaaggtaaaa
ctctatatgatgctatcgttaaagttcacgtaaaaacgattgattatgat
ggacaataccatgtcagaatcgttgataaagaagcatttacaaaagccaa
taccgataaatctaacaaaaagaacaacaagataactcagctaagaagg
aagctactccagctacgcctagcaaaccaacaccatcacctgttgaaaaa
gaatcacaaaaacaagacagccaaaaagatgacaataaacaattaccaag
tgttgaaaaagaaaatgacgcatctagtgagtcaggtaaagacaaaacgc
ctgctacaaaaccaactaaaggtgaagtagaatcaagtagtacaactcca
actaaggtagtatctacgactcaaatgttgcaaaaccaacaactgcttc
atcaaaacaacaaaagatgttgttcaaacttcagcaggttctagcgaag
caaaagatagtgctccattacaaaaagcaaacattaaaaacacaaatgat
ggacacactcaaagccaaaacaataaaaatacacaagaaataaagcaaaa
atcattaccacaaactggtgaagaatcaaataaagatatgacattaccat
taatggcattattagctttaagtagcatcgttgcattcgtattacctaga
aaacgtaaaaactaa KrkN (8325)
(SEQ ID NO: 10)
YTIRSGFYNMNKQQKEFKSFYSIRKSSLGVASVAISTLLLLMSNGEAQAA
AEETGGTNTEAQPKTEAVASPTTTSEKAPETKPVANAVSVSNKEVEAPTS
ETKEAKEVKEVKAPKETKEVKPAAKATNNTYPILNQELREAIKNPAIKDK DHSAPNSRPIDFEMKKKDGTQQFYHYASSVKPARVIFTDSKPEIELGLQS
GQFWRKFEVYEGDKKLPIKLVSYDTVKDYAYIRFSVSNGTKAVKIVSSTH
FNNKEEKYDYTLMEFAQPIYNSADKFKTEEDYKAEKLLAPYKKAKTLERQ
VYELNKIQDKLPEKLKAEYKKKLEDTKKALDEQVKSAITEFQNVQPTNEK
MTDLQDTKYVVYESVENNESMMDTFVKHPIKTGMLNGKKYMVMETTNDDY
WKDFMVEGQRVRTISKDAKNNTRTIIFPYVEGKTLYDAIVKVHVKTIDYD
GQYHVRIVDKEAFTKANTDKSNKKEQQDNSAKKEATPATPSKPTPSPVEK
ESQKQDSQKDDNKQLPSVEKENDASSESGKDKTPATKPTKGEVESSSTTP
TKVVSTTQNVAKPTTASSKTTKDVVQTSAGSSEAKDSAPLQKANIKNTND
GHTQSQNNKNTQENKAKSLPQTGEESNKDMTLPLMALLALSSIVAFVLPR
KRKN RkaS (COL)
(SEQ ID NO: 11)
tttataaataatttacataaaatcaatcatttaatataaggattatgat
aatatattggtgtatgacagttaatggagggaacgaaatgaaagctttat
tacttaaaacaagtgtatggctcgttttgcttttagtgtaatgggatta
tggcaagtctcgaacgcggctgagcagcatacaccaatgaaagcacatgc
agtaacaacgatagacaaagcaacaacagataagcaacaagtaccgccaa
caaaggaagcggctcatcattctggcaaagaagcggcaaccaacgtatca
gcatcagcgcagggaacagctgatgatacaaacagcaaagtaacatccaa
cgcaccatctaacaaaccatctacagtagttcaacaaaagtaaacgaaa
cacgcgacgtagatacaacaagcctcaacacaaaaccaactcacaca
gcaacgttcaaattatcaaatgctaaaacagcatcactttcaccacgaat
gtttgctgctaatgcaccacaaacaacaacacataaaatattacatacaa
atgatatccatggccgactagccgaagaaaagggcgtgtcatcggtatg
gctaaattaaaaacagtaaaagaacaagaaaagcctgatttaatgttaga
cgcaggagacgccttccaaggtttaccactttcaaaccagtctaaaggtg
aagaaatggctaaagcaatgaatgcagtaggttatgatgctatggcagtc
ggtaaccatgaatttgactttggatacgatcagttgaaaaagttagaggg
tatgttagacttcccgatgctaagtactaacgtttataaagatggaaaac
gcgcgtttaagccttcaacgattgtaacaaaaaatggtattcgttatgga
attattggtgtaacgacaccagaaacaaagacgaaaacaagacctgaagg
cattaaaggcgttgaatttagagatccattacaaagtgtgacagcggaaa
tgatgcgtatttataaagacgtagatacatttgttgttatatcacattta
ggaattgatccttcaacacaagaaacatggcgtggtgattacttagtgaa
acaattaagtcaaaatccacaattgaagaaacgtattacagttattgatg
gtcattcacatacagtacttcaaaatggtcaaatttataacaatgatgca
ttggcacaaacaggtacagcacttgcgaatatcggtaagattacatttaa
ttatcgcaatggagaggtatcgaatattaaaccgtcattgattaatgtta
aagacgttgaaaatgtaacaccgaacaaagcattagctgaacaaattaat
caagctgatcaaacatttagagcacaaactgcagaggtaattattccaaa caataccattgattttcaaaggagaaagagatgacgttagaacgcgtgaaa
caaatttaggaaacgcgattgcagatgctatggaagcgtatggcgttaag
aatttctctaaaaagactgactttgccgtgacaaatggtggaggtattcg
tgcctctatcgcaaaaggtaaggtgacacgctatgatttaatctcagtat
taccatttggaaatacgattgcgcaaattgatgtaaaaggttcagacgtc
tggacggctttcgaacatagtttaggcgcaccaacaacacaaaaggacgg
taagacagtgttaacagcgaatggcggtttactacatatctctgattcaa
tccgtgtttactatgatataaataaaccgtctggcaaacgaattaatgct
attcaaattttaaataaagagacaggtaagtttgaaaatattgatttaaa
acgtgtatatcacgtaacgatgaatgacttcacagcatcaggtggcgacg
gatatagtatgttcggtggtcctagagaagaaggtatttcattagatcaa
gtactagcaagttatttaaaaaacagctaacttagctaagtatgatacgac
agaaccacaacgtatgttattaggtaaaccagcagtaagtgaacaaccag
ctaaaggacaacaaggtagcaaaggtagtaagtctggtaaagatacacaa
ccaattggtgacgacaaagtgatggatccagcgaaaaaaccagctccagg
taaagttgtattgttgctagcgcatagaggaactgttagtagcggtacag
aaggttctggtcgcacaatagaaggagctactgtatcaagcaagagtggg
aaacaattggctagaatgtcagtgcctaaaggtagcgcgcatgagaaaca
gttaccaaaaactggaactaatcaaagttcaagcccagaagcgatgtttg
tattattagcaggtataggtttaatcgcgactgtacgacgtagaaaagct
agctaa RkaS (COL)
(SEQ ID NO: 12)
FINNLHKINHFNIRIMIIYWCMTVNGGNEMKALLLKTSVWLVLLFSVMGL
WQVSNAAEQHTPMKAHAVTTIDKATTDKQQVPPTKEAAHHSGKEAATNVS
ASAQGTADDTNSKVTSNAPSNKPSTVVSTKVNETRDVDTQQASTQKPTHT
ATFKLSNAKTASLSPRMFAANAPQTTTHKILHTNDIHGRLAEEKGRVIGM
AKLKTVKEQEKPDLMLDAGDAFQGLPLSNQSKGEEMAKAMNAVGYDAMAV
GNHEFDFGYDQLKKLEGMLDFPMLSTNVYKDGKRAFKPSTIVTKNGIRYG
IIGVTTPETKTKTRPEGIKGVEFRDPLQSVTAEMMRIYKDVDTFVVISHL
GIDPSTQETWRGDYLVKQLSQNPQLKKRITVIDGHSHTVLQNGQIYNNDA
LAQTGTALANIGKITFNYRNGEVSNIKPSLINVKDVENVTPNKALAEQIN
QADQTFRAQTAEVIIPNNTIDFKGERDDVRTRETNLGNAIADAMEAYGVK
NFSKKTDFAVTNGGGIRASIAKGKVTRYDLISVLPFGNTIAQIDVKGSDV
WTAFEHSLGAPTTQKDGKTVLTANGGLLHISDSIRVYYDINKPSGKRINA
IQILNKETGKFENDLKRVYHVTMNDFTASGGDGYSMFGGPREEGISLDQV
LASYLKTANLAKYDTTEPQRMLLGKPAVSEQPAKGQQGSKGSKSGKDTQP
IGDDKVMDPAKKPAPGKVVLLLAHRGTVSSGTEGSGRTIEGATVSSKSGK
QLARMSVPKGSAHEKQLPKTGTNQSSSPEAMFVLLAGIGLIATVRRRKAS RrkN (8325)
(SEQ ID NO: 13)
agtggaaaatatgaaaaaggagtatgcaaatgagagataagaaaggacc
ggtaaataaagagtagattttctatcaaataaattgaataaatattcaa -continued taagaaaatttacagttggaacagcatctattttaattggctcactaatg
tatttgggaactcaacaagaggcagaagcagctgaaaacaatattgagaa
tccaactacattaaaagataatgtccaatcaaaagaagtgaagattgaag
aagtaacaaacaaagacactgcaccacagggtgtagaagctaaatctgaa
gtaacttcaaacaaagacacaatcgaacatgaaccatcagtaaaagctga
agatatatcaaaaaggaggatacaccaaaagaagtagctgatgttgctg
aagttcagccgaaatcgtcagtcactcataacgcagagacacctaaggtt
agaaaagctcgttctgttgatgaaggctcttttgatattacaagagattc
taaaaatgtagttgaatctaccccaattacaattcaaggtaaagaacatt
ttgaaggttacggaagtgttgatatacaaaaaaaaccaacagatttaggg
gtatcagaggtaaccaggtttaatgttggtaatgaaagtaatggtttgat
aggagctttacaattaaaaaataaaatagattttagtaaggatttcaatt
ttaaagttagagtggcaaataaccatcaatcaaataccacaggtgctgat
ggttgggggttcttatttagtaaaggaaatgcagaagaatatttaactaa
tggtggaatccttggggataaaggtctggtaaattcaggcggatttaaaa
ttgatactggatacattatacaagttccatggacaaaactgaaaagcaa
gctggacaaggttatagaggatacggagcttttgtgaaaaatgacagttc
tggtaattcacaaatggttggagaaaatattgataaatcaaaaactaatt
ttttaaactatgcggacaattcaactaatacatcagatggaaagtttcat
gggcaacgtttaaatgatgtcatcttaacttatgttgcttcaactggtaa
aatgagagcagaatatgctggtaaaacttgggagacttcaataacagatt
taggtttatctaaaaatcaggcatataattcttaattacatctagtcaa
agatggggccttaatcaaggatatcgatcgtaaaaaaactaacttggaaacctgaaggtctttaccttttaccagagcgccaaaaacaataacagaattagaaaaaagttgaagagattccattcaagaaagaacgtaaa
tttaatccggatttagcaccagggacagaaaagtaacaagagaaggaca
aaaggtgagaagacaataacgacaccaacactaaaaaatccattaactg
gagtaattattagtaaaggtgaaccaaaagaagagattacaaagatccg
attaatgaattaacagaatacggacctgaaacaatagcgccaggtcatcg
agacgaatttgatccgaagttaccaacaggagagaaagaggaagttccag
gtaaaccaggaattaagaatccagaaacaggagacgtagttagaccgccg
gtcgatagcgtaacaaaatatggacctgtaaaaggagactcgattgtaga
aaaagaagagattccattcgagaaagaacgtaaatttaatcctgatttag
caccagggacagaaaaagtaacaagagaaggacaaaaggtgagaagaca
ataacgacgccaacactaaaaaatccattaactggagaaattattagtaa
aggtgaatcgaaagaagaaatcacaaaagatccgattaatgaattaacag
aatacggaccagaaacgataacaccaggtcatcgagacgaatttgatccg
aagttaccaacaggagagaaagaggaagttccaggtaaaccaggaattaa
gaatccagaaacaggagatgtagttagaccaccggtcgatagcgtaacaa
aatatggacctgtaaaaggagactcgattgtagaaaaagaagagattcca -continued ttcgagaaagaacgtaaatttaatcctgatttagcaccagggacagaaaa
agtaacaagagaaggacaaaaaggtgagaagacaataacgacaccaacac
taaaaaatccattaactggagtaattattagtaaaggtgaaccaaaagaa
gaaatcacaaaagatccgattaatgaattaacagaatacggaccagaaac
gataacaccaggtcatcgagacgaatttgatccgaagttaccaacaggag
agaaagaagaagttccaggtaaaccaggaattaagaatccagaaacagga
gacgtagttagaccaccggtcgatagcgtaacaaaatatggacctgtaaa
aggagactcgattgtagaaaaagaagagattccattcaagaaagaacgta
aatttaatccggatttagcaccagggacagaaaaagtaacaagagaagga
caaaaaggtgagaagacaataacgacgccaacactaaaaaatccattaac
tggagaaattattagtaaaggtgaatcgaaagaagaaatcacaaaagatc
cgattaatgaattaacagaatacggaccagaaacgataacaccaggtcat
cgagacgaatttgatccgaagttaccaacaggagagaaagaggaagttcc
aggtaaaccaggaattaagaatccagaaacaggagatgtagttagaccac
cggtcgatagcgtaacaaaatatggacctgtaaaaggagactcgattgta
gaaaaagaagagattccattcgagaaagaacgtaaatttaatcctgattt
agcaccagggacagaaaaagtaacaagagaaggacaaaaaggtgagaaga
caataacgacgccaacactaaaaaatccattaactggagaaattattagt
aaaggtgaatcgaaagaagaaatcacaaaagatccgattaatgaattaac
agaatacggaccagaaacgataacaccaggtcatcgagacgaatttgatc
cgaagttaccaacaggagagaaagaggaagttccaggtaaaccaggaatt
aagaatccagaaacaggagacgtagttagaccaccggtcgatagcgtaac
aaaatatggacctgtaaaaggagactcgattgtagaaaaagaagaaattc
cattcaagaaagaacgtaaatttaatcctgatttagcaccagggacagaa
aaagtaacaagagaaggacaaaaaggtgagaagacaataacgacgccaac
actaaaaaatccattaactggagaaattattagtaaaggtgaatcgaaag
aagaaatcacaaaagatccgattaatgaattaacagaatacggaccagaa
acgataacaccaggtcatcgagacgaatttgatccgaagttaccaacagg
agagaaagaggaagttccaggtaaaccaggaattaagaatccagaaacag
gagatgtagttagaccaccggtcgatagcgtaacaaaatatggacctgta
aaaggagactcgattgtagaaaaagaagaaattccattcgagaaagaacg
taaatttaatcctgatttagcaccagggacagaaaaagtaacaagagaag
gacaaaaggtgagaagacaataacgacgccaacactaaaaaatccatta
actggagaaattattagtaaaggtgaatcgaaagaagaaatcacaaaaga
tccgattaatgaattaacagaatacggaccagaaacgataacaccaggtc
atcgagacgaatttgatccgaagttaccaacaggagagaaagaggaagtt
ccaggtaaaccaggaattaagaatccagaaacaggagatgtagttagacc
accggtcgatagcgtaacaaaatatggacctgtaaaaggagactcgattg
tagaaaaagaagaaattccattcgagaaagaacgtaaatttaatcctgat
ttagcaccagggacagaaaaagtaacaagagaaggacaaaaaggtgagaa
gacaataacgacgccaacactaaaaaatccattaactggagaaattatta -continued

```
gtaaaggtgaatcgaaagaagaaatcacaaaagatccagttaatgaatta
acagaattcggtggcgagaaaataccgcaaggtcataaagatatctttga
tccaaacttaccaacagatcaaacggaaaaagtaccaggtaaaccaggaa
tcaagaatccagacacaggaaaagtgatcgaagagccagtggatgatgtg
attaaacacggaccaaaaacgggtacaccagaaacaaaaacagtagagat
accgtttgaaacaaaacgtgagtttaatccaaaattacaacctggtgaag
agcgagtgaaacaagaaggacaaccaggaagtaagacaatcacaacacca
atcacagtgaacccattaacaggtgaaaaagttggcgagggtcaaccaac
agaagagatcacaaaacaaccagtagataagattgtagagttcggtggag
agaaaccaaaagatccaaaaggacctgaaaacccagagaagccgagcaga
ccaactcatccaagtggcccagtaaatcctaacaatccaggattatcgaa
agacagagcaaaaccaaatgggcccagttcattcaatggataaaaatgata
aagttaaaaaatctaaaattgctaaagaatcagtagctaatcaagagaaa
aaacgagcagaattaccaaaaacaggtttagaaagcacgcaaaaaggttt
gatctttagtagtataattggaattgctggattaatgttattggctcgta
gaagaaagaattaa
```

RrkN (8325)
(SEQ ID NO: 14)

```
SGKYGKRSMQMRDKKGPVNKRVDFLSNKLNKYSIRKFTVGTASILIGSLM
YLGTQQEAEAAENNIENPTTLKDNVQSKEVKIEEVTNKDTAPQGVEAKSE
VTSNKDTIEHEPSVKAEDISKKEDTPKEVADVAEVQPKSSVTHNAETPKV
RKARSVDEGSFDITRDSKNVVESTPITIQGKEHFEGYGSVDIQKKPTDLG
VSEVTRFNVGNESNGLIGALQLKNKIDFSKDFNFKVRVANNHQSNTTGAD
GWGFLFSKGNAEEYLTNGGILGDKGLVNSGGFKIDTGYIYTSSMDKTEKQ
AGQGYRGYGAFVKNDSSGNSQMVGENIDKSKTNFLNYADNSTNTSDGKFH
GQRLNDVILTYVASTGKMRAEYAGKTWETSITDLGLSKNQAYNFLITSSQ
RWGLNQGINANGWMRTDLKGSEFTFTPEAPKTITELEKKVEEIPFKKERK
FNPDLAPGTEKVTREGQKGEKTITTPTLKNPLTGVIISKGEPKEEITKDP
INELTEYGPETIAPGHRDEFDPKLPTGEKEEVPGKPGIKNPETGDVVRPP
VDSVTKYGPVKGDSIVEKEEIPFEKERKFNPDLAPGTEKVTREGQKGEKT
ITTPTLKNPLTGEIISKGESKEEITKDPINELTEYGPETITPGHRDEFDP
KLPTGEKEEVPGKPGIKNPETGDVVRPPVDSVTKYGPVKGDSIVEKEEIP
FEKERKFNPDLAPGTEKVTREGQKGEKTITTPTLKNPLTGVIISKGEPKE
EITKDPINELTEYGPETITPGHRDEFDPKLPTGEKEEVPGKPGIKNPETG
DVVRPPVDSVTKYGPVKGDSIVEKEEIPFKKERKFNPDLAPGTEKVTREG
QKGEKTITTPTLKNPLTGEIISKGESKEEITKDPINELTEYGPETITPGH
RDEFDPKLPTGEKEEVPGKPGIKNPETGDVVRPPVDSVTKYGPVKGDSIV
EKEEIPFEKERKFNPDLAPGTEKVTREGQKGEKTITTPTLKNPLTGEIIS
KGESKEEITKDPINELTEYGPETITPGHRDEFDPKLPTGEKEEVPGKPGI
KNPETGDVVRPPVDSVTKYGPVKGDSIVEKEEIPFKKERKFNPDLAPGTE
KVTREGQKGEKTITTPTLKNPLTGEIISKGESKEEITKDPINELTEYGPE
TITPGHRDEFDPKLPTGEKEEVPGKPGIKNPETGDVVRPPVDSVTKYGPV
KGDSIVEKEEIPFEKERKFNPDLAPGTEKVTREGQKGEKTITTPTLKNPL
TGEIISKGESKEEITKDPINELTEYGPETITPGHRDEFDPKLPTGEKEEV
PGKPGIKNPETGDVVRPPVDSVTKYGPVKGDSIVEKEEIPFEKERKFNPD
LAPGTEKVTREGQKGEKTITTPTLKNPLTGEIISKGESKEEITKDPVNEL
TEFGGEKIPQGHKDIFDPNLPTDQTEKVPGKPGIKNPDTGKVIEEPVDDV
IKHGPKTGTPETKTVEIPFETKREFNPKLQPGEERVKQEGQPGSKTITTP
ITVNPLTGEKVGEGQPTEEITKQPVDKIVEFGGEKPKDPKGPENPEKPSR
PTHPSGPVNPNNPGLSKDRAKPNGPVHSMDKNDKVKKSKIAKESVANQEK
KRAELPKTGLESTQKGLIFSSIIGIAGLMLLARRRKN
```

KnkA (8325)
(SEQ ID NO: 15)

```
ggaaggagtatgttgatggctaaatatcgagggaaaccgtttcaattata
tgtaaagttatcgtgttcgacaatgatgcgacaagtatcattttaacga
atatcttgccgtacgatgcccaagctgcatctgaaaaggatactgaaatt
acaaaagagatattatctaagcaagatttattagacaaagttgacaaggc
aattcgtcaaattgagcaattaaaaacagttatcggcttcatctaaagaac
attataaagcacaactaaatgaagcgaaaacagcatcgcaaatagatgaa
atcataaaacgagctaatgagttggatagcaaagacaataaaagttctca
cactgaaatgaacggtcaaagtgatatagacagtaaattagatcaattgc
ttaaagatttaaatgaggtttcttcaaatgttgatagggggtcaacaaagt
ggcgaggacgatcttaatgcaatgaaaaatgatatgtcacaaacggctac
aacaaaacatggagaaaaagatgataaaaatgatgaagcaatggtaaata
aggcgttagaagacctagaccatttgaatcagcaaatacacaaatcgaaa
gatgcatcgaaagatacatcggaagatccagcagtgtctacaacagataa
taatcatgaagtagctaaaacgccaaataatgatggttctggacatgttg
tgttaaataaattcctttcaaatgaagagaatcaaagccatagtaatcga
ctcactgataaaattacaaggaagcgataaaattaatcatgctatgattga
aaaattagctaaaagtaatgcctcaacgcaacattacacatatcataaac
tgaatacgttacaatctttagatcaacgtattgcaaatacgcaacttcct
aaaaaatcaaaaatcagacttaatgagcgaagtaaataagacgaaagagcg
tataaaaagtcaacgaaatattttttggaagaacttgcacgtactgatg
ataaaaagtatgctacacaaagcattttagaaagtatatttaataaagac
gaggcagttaaaattctaaaagatatacgtgttgatggtaaaacagatca
acaaaattgcagatcaaattactcgtcatattgatcaattatctctgacaa
cgagtgatgatttattaacgtcattgattgatcaatcacaagataagtcg
ctattgatttctcaaatttacaaacgaaattaggaaaagctgaagcaga
taaattggctaaagattggacgaataaaggattatcaaatcgcccaaatcg
ttgaccaattgaagaaacattttgcatcaactggcgacacgtcttcagat
gatatattaaaagcaattttgaataatgccaaagataaaaaacaagcaat
tgaaacgattttagcaacacgtatagaaagacaaaaggcaaaattactgg
cagatttaattactaaaatagaaacagatcaaaataaaattttaattta
```

-continued

```
gttaaatcggcattgaatggtaaagcggatgatttattgaatttacaaaa gagactcaatcaaacgaaaaagatatagattatattttatcaccaatag taaatcgtccaagtttactagatcgattgaataaaaatgggaaaacgaca gatttaaataagttagcaaatttaatgaatcaaggatcagatttattaga cagtattccagatatacccacaccaaagccagaaaagacgttaacacttg gtaaaggtaatggattgttaagtggattattaaatgctgatggtaatgta tctttgcctaaagcgggggaaacgataaaagaacattggttgccgatatc tgtaattgttggtgcaatgggtgtactaatgatttggttatcacgacgca ataagttgaaaaataaagcataa
```

KnkA (8325)

(SEQ ID NO: 16)

GRSMLMAKYRGKPFQLYVKLSGSTMMATSIILTNILPYDAQAASEKDTEI

TKEILSKQDLLDKVDKAIRQIEQLKQLSASSKEHYKAQLNEAKTASQIDE

IIKRANELDSKDNKSSHTEMNGQSDIDSKLDQLLKDLNEVSSNVDRGQQS

GEDDLNAMKNDMSQTATTKHGEKDDKNDEAMVNKALEDLDHLNQQIHKSK

DASKDTSEDPAVSTTDNNHEVAKTPNNDGSGHVVLNKFLSNEENQSHSNR

LTDKLQGSDKINHAMIEKLAKSNASTQHYTYHKLNTLQSLDQRIANTQLP

KNQKSDLMSEVNKTKERIKSQRNIILEELARTDDKKYATQSILESIFNKD

EAVKILKDIRVDGKTDQQIADQITRHIDQLSLTTSDDLLTSLIDQSQDKS

LLISQILQTKLGKAEADKLAKDWTNKGLSNRQIVDQLKKHFASTGDTSSD

DILKAILNNAKDKKQAIETILATRIERQKAKLLADLITKIETDQNKIFNL

VKSALNGKADDLLNLQKRLNQTKKDIDYILSPIVNRPSLLDRLNKNGKTT

DLNKLANLMNQGSDLLDSIPDIPTPKPEKTLTLGKGNGLLSGLLNADGNV

SLPKAGETIKEHWLPISVIVGAMGVLMIWLSRRNKLKNKA

Figure 1:
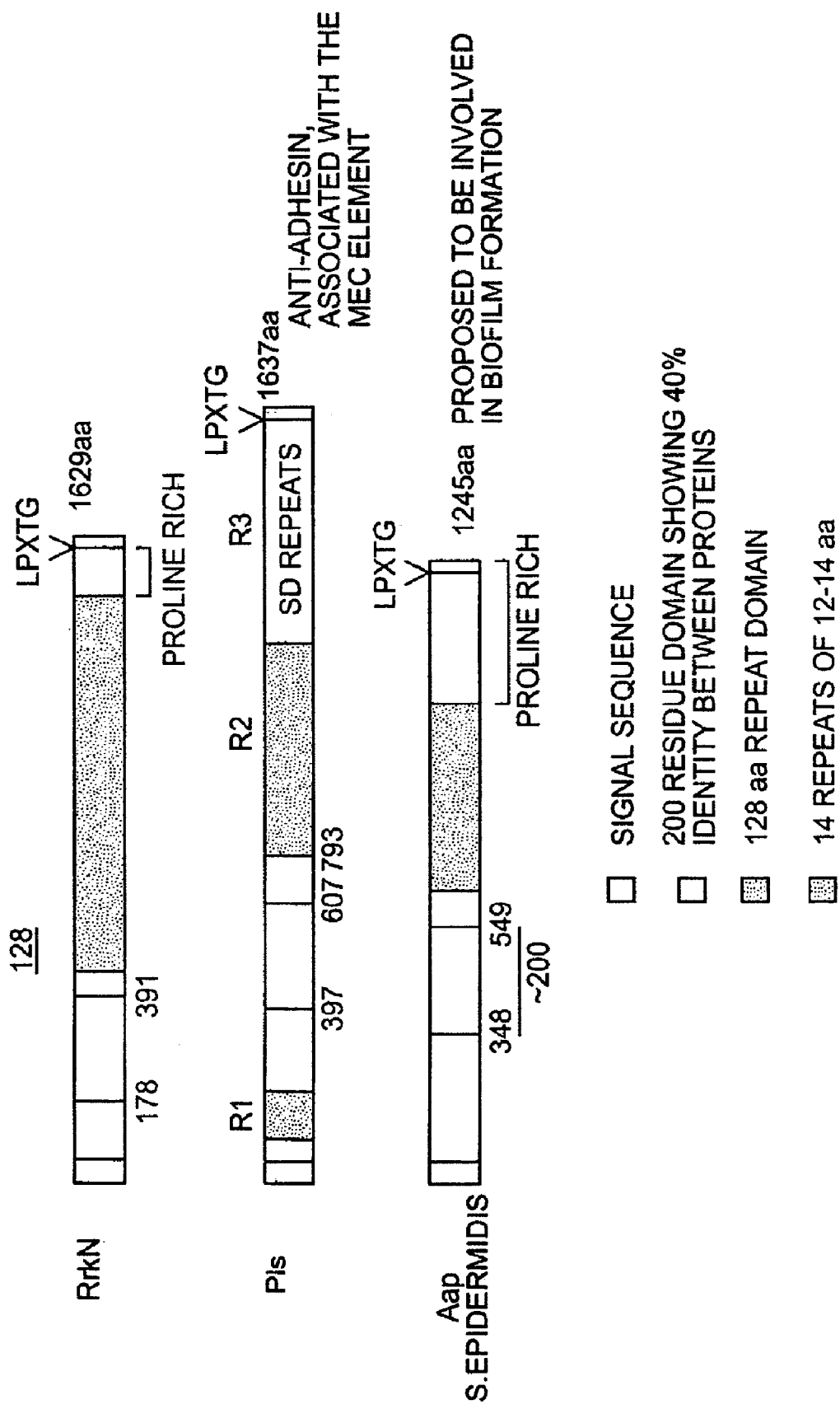
FIG. 1 is a depiction of the primary structure of the in silico-predicted proteins in accordance with the present invention.
Figure 1:
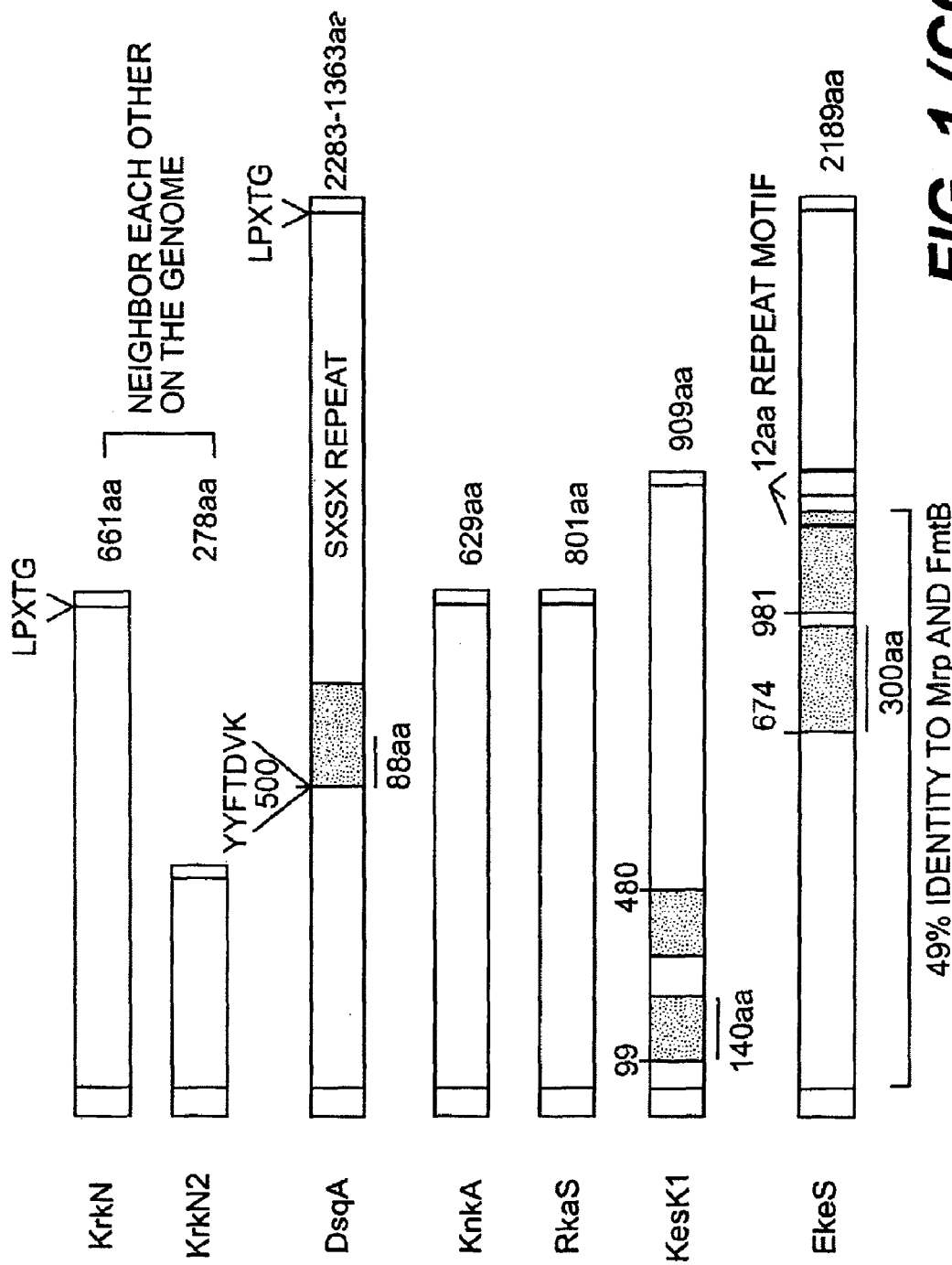

Primary Structure Analysis:

A bioinformatic approach was used for primary structure and function prediction (FIG. 1). Proteins RrkN and DsqA possessed a similar structural organization to previously described MSCRAMMs. RrkN is similar in structure to the Pls/Aap proteins of *S. aureus* and *S. epidermidis*, respectively. It contains a 200-residue domain at its N-terminus showing 40% identity to Pls and Aap. The C-terminus of the protein is predominantly composed of a 128 residue repeat domain, which varies in the numbers of repeats from strain to strain. These repeats are also present in Pls and Aap. A putative sar homolog and fnbpA and fnbpB lie directly upstream from RrkN on the genome.

DsqA is similar in structural organization to the Sdr family of proteins. It contains a typical A domain followed by a TYYFTDVK (SEQ ID NO: 30) motif which is similar to a conserved TYTFTVYVD (SEQ ID NO: 31) motif found in all of the Sdr proteins. The function of this motif has yet to be determined. Two 88 residue repeat domains reside in the centre of the protein followed by a C-terminal SX-repeat motif similar to the SD-repeat motif found in the Sdr proteins. The size of this repeat varies from strain to strain. DsqA neighbors secY and secA on the genome. A DsqA homolog (>90% identical) is also found in *S. epidermidis*.

KnkA contains no repeat domains in its sequence. Secondary structure prediction analysis indicate that this protein is predominantly composed of alpha-helices.

RkaS contains no repeat domains in its sequence. BLAST analysis indicates that it is similar to a 5' nucleotidase UDP-sugar hydrolase. The gene encoding RkaS lies directly upstream from orfX, the insertion site of the mec element.

KesK contains two 140 residue repeat domains at the N-terminus of the protein which are 38% identical. Hydropathy plot analysis (Kyte and Doolittle, 1982) indicates that there is a large hydrophilic domain in the center of the protein (residue 500-560).

EkeS contains two 300 residue repeat domains in the center of the protein which are 38% identical. Blast analysis indicates that the N-terminus of the protein (residues 1-1268, bearing both repeats) is 49% identical to FmtB, an LPXTG protein with 17 tandem repeats. FmtB is proposed to be involved indirectly in methicillin resistance as inactivation of fmtB abolishes methicillin resistance. This appears to be due to affecting cell wall composition as methicillin sensitivity can be relieved by increasing the production of the cell wall precursor glucosamine-1-phosphate (Komatsuzawa et al., 2000).

KrkN and KrkN2 neighbor each other on the genome.

Figure 2:
FIG. 2 shows a Coomassie gel of the purified N-terminal recombinant His-tagged proteins expressing the orfs of the present invention.
Figure 3A:
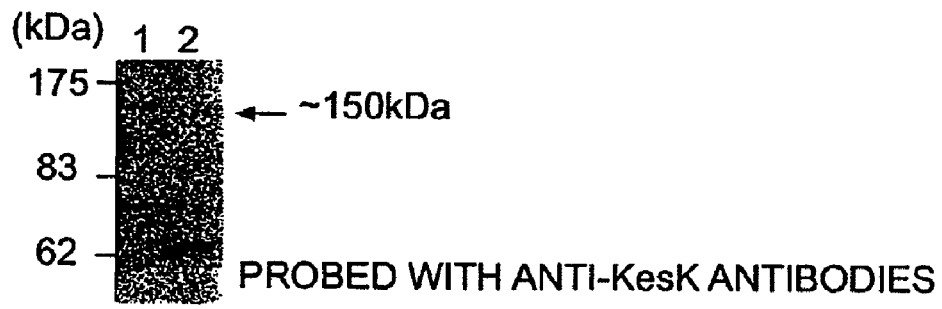
FIGS. 3A-3C show Western blotting of *S. aureus* cell wall extracts showing probing with anti-KesK antibodies (FIG. 3A), anti-KnkA antibodies (FIG. 3B) and anti-DsqA antibodies (FIG. 3C), respectively.
Figure 3B:
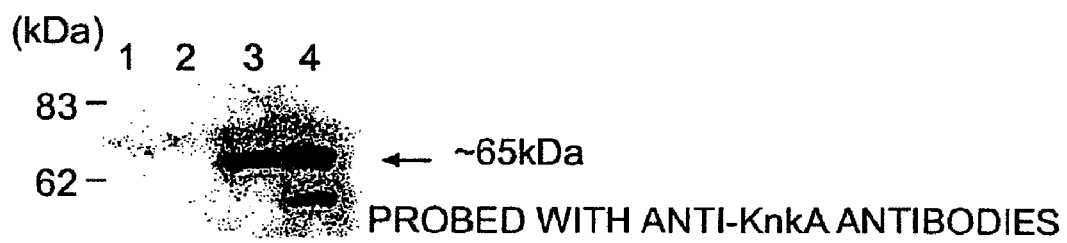
Figure 3C:

Expression Analysis:

Due to lack of sequence homology with protein databases, a putative function for each of these proteins could not be predicted and hence a molecular approach was taken. Unique regions of four of the orfs were expressed in *E. coli* as recombinant his-tagged fusion proteins using the Qiagen pQE-30 expression system. FIG. 2. represents a Coomassie stained SDS-PAGE gel of the purified N-terminal his-tag fusion proteins. The recombinant proteins RrkN1, DsqA2, KesK1 and KnkA were used to generate antibodies in rabbits. Western blotting analysis of *S. aureus* cell wall extracts revealed that KesK, KnkA and DsqA are expressed and cell wall-associated (FIG. 3). Strain eMRSA-16 represents a knkA-negative strain since it lacks the knkA gene. An immunoreactive band of 65 kDa reacts with the cell wall fraction from both exponential and stationary phase cells of strain 8325-4 (FIG. 3, B). The absence of this band in strain eMRSA-16 suggests that it represents the gene product of knkA.

Western immunoblotting of the cell wall fraction of strain 8325-4 using anti-KesK antibodies identified a 150 kDa immunoreactive band in both exponential and stationary phase cultures. A similar sized immunoreactive protein released from the cell wall fraction of *Lactococcus* lactis expressing full length KesK on an expression plasmid (pKS80) suggests that the 150 kDa band represents the keskgene product (data not shown). A kesk knockout mutant in *S. aureus* would be required to confirm the size of the cell wall-released KesK protein.

Western immunoblotting of the cell wall fraction of *S. aureus* strain MSSA and eMRSA-16 using anti-DsqA antibodies identified a 130 kDa immunoreactive band. Expression levels are higher in stationary phase cells.

Figure 4A:
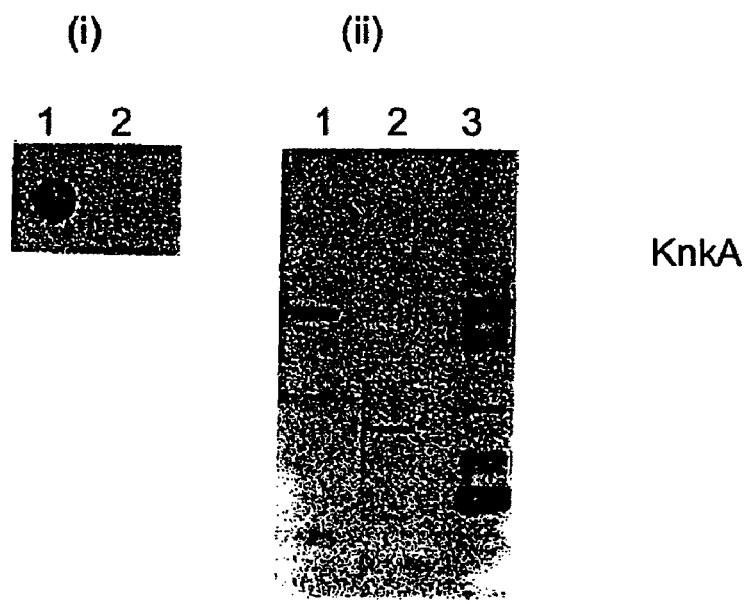
FIGS. 4A-4B show Dot-blotting and Western immunoblotting of *Lactococcus* lactis expressing *S. aureus* MSCRAMM®s, namely KnkA (FIG. 4A) and KesK (FIG. 4B).
Figure 4B:
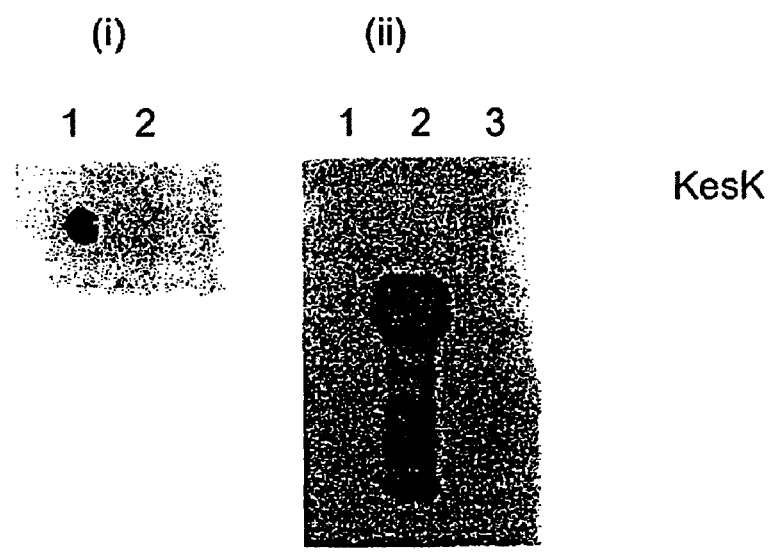

Heterologous Expression in *Lactococcus lactis*:

Heterologous expression of *S. aureus* surface proteins in *Lactococcus lactis* (*L. lactis*) has previously been used as a tool to study protein function (Sinha et al., 2000). In this study this surrogate system will be used to express each of the in silico-predicted MSCRAMMs on the surface of *L. lactis* to fish for a function. KesK and KnkA have been cloned into *L. lactis* and shown by dot blotting to be surface expressed (FIG. 4). No cross reaction was observed with the negative control (pKS80 plasmid without an insert) indicating that this is a specific reaction. Cell wall and protoplast fractions of *Lactococcus lactis* bearing pKS-KnkA and pKS-KesK were generated by digestion of cells with lysozyme and mutanolysin and used in Western blotting studies using anti-KnkA and anti-KesK antibodies, respectively. Unlike what was observed in *S. aureus*, KnkA was not detected in the cell wall fraction of L. lactis but found to be associated with the protoplast fraction. The anchoring motif of KnkA differs from the consensus LPXTG (SEQ ID NO: 32) sequence in that it contains an Alanine residue instead of a Threonine (i.e. LPKAG, SEQ ID NO: 33) (Table 1). It has been recently been published that S. aureus contains two sortase genes, srtA and srtB (Pallen, 2001). It is possible that this variant form of the LPXTG (SEQ ID NO: 32) motif is processed by the second sortase gene, which is absent in L. lactis. This would also explain the slight increase in size of the KnkA protein observed in the protoplast fraction, as the cell wall sorting signal has not been cleaved.

KesK was detected in the cell wall fraction of L. lactis but migrated at a smaller molecular weight than the KesK protein released from the cell wall of S. aureus. The majority of MSCRAMMs expressed on the surface of L. lactis are prone to proteolysis during the cell wall extraction procedure (Louise O'Brien, personal communication). Therefore, it is possible that the KesK protein released from the surface of L. lactis represents a truncated form of KesK. Shorter digestion times with lysozyme and mutanolysin has been shown to limit the extent of proteolysis.

Expression of in Silico-Predicted MSCRAMMs in vivo:

Convalescent-phase sera from 33 patients recovering from S. aureus infections were tested in their ability to recognize the purified N-terminal his-tag fusion proteins in an ELISA assay. Pooled sera from children and healthy blood donors were used as negative controls. A positive reaction was taken as a value equal to or greater than twice the value of the negative control. FIGS. 5A-5D illustrate that all of the proteins were recognized by 27-42% of the patients suggesting that these proteins are expressed in vivo and are immunogenic during infection of the host.

REFERENCES

Komatsuzawa, H., Ohta, K., Sugai, M., Fujiwara, T., Glanzmann, P., Berger-Bachi, B., Suginaka, H. (2000) Tn551-mediated insertional inactivation of the fmtB gene encoding a cell wall-associated protein abolishes methicillin resistance in Staphylococcus aureus. J. Antimicrob. Chemother. 45: 421-31.

Sinha, B., Francois, P., Que, Y. A., Hussain, M., Heilmann, C., Moreillon, P., Lew, D., Krause, K. H., Peters, G., Herrmann, M. (2000) Heterologously expressed Staphylococcus aureus fibronectin-binding proteins are sufficient for invasion of host cells. Infect. Immun. 68: 6871-6878.

Pallen, M. J., Lam, A. C., Antonio, M., Dunbar, K. (2000) An embarrassment of sortases—a richness of substrates? Trends. Microbiol. 9: 97-101

Example 2

Isolation and Sequencing of Cross-Reactive Proteins from S. Aureus and from Coagulase-Negative Staphylococci It has been recently shown that S. epidermidis contains surface proteins structurally related to S. aureus MSCRAMM® proteins (U.S. Ser. No. 09/386,962). One protein from S. aureus is of particular interest since it has a close homologue in S. epidermidis. The protein is called DsqA or SasA (S. aureus) and DgsK (S. epidermidis). They are characterized by a typical "A" domain of approximately 500 amino acid residues, followed by two B repeats of 88 residues that are 40% identical, and a unique SXSX dipeptide repeat that can vary in length depending on the strain. Contained within the A domain of the S. aureus DsqA/SasA is a 180 residue region that has ~40% identity to a similar sized domain within region A of S. aureus proteins RrkN, Pls and S. epidermidis protein Aap The A regions of the DsqA/SasA and DgsK proteins are 46% identical at the amino acid level, the BB repeats are 50% identical. Active and passive immunization strategies that include; vaccines, polyclonal and monoclonal antibodies recognizing both S. aureus and coagulase-negative staphylococcal proteins are the subject of this invention.

Specific Examples of Antibodies that Cross-React with Coagulase-Negative Staphylococci and S. aureus.

```
Coagulase-negative staphylococcal DgsK A-Domain:
Amino Acid Sequence
                                        (SEQ ID NO: 17)
ASETPITSEISSNSETVANQNSTTIKNSQKETVNSTSLESNHSNSTNKQM

SSEVTNTAQSSEKAGISQQSSETSNQSSKLNTYASTDHVESTTINNDNTA

QQDQNKSSNVTSKSTQSNTSSSEKNISSNLTQSIETKATDSLATSEARTS

TNQISNLTSTSTSNQSSPTSFANLRTFSRFTVLNTMAAPTTTSTTTTSSL

TSNSVVVNKDNFNEHMNLSGSATYDPKTGIATLTPDAYSQKGAISLNTRL

DSNRSFRFIGKVNLGNRYEGYSPDGVAGGDGIGFAFSPGPLGQIGKEGAA

VGIGGLNNAFGFKLDTYHNTSTPRSDAKAKADPRNVGGGAFGAFVSTDR

NGMATTEESTAAKLNVQPTDNSFQDFVIDYNGDTKVMTVTYAGQTFTRNL

TDWIKNSGGTTFSLSMTASTGGAKNLQQVQFGTFEYTESAVAKVRYVDAN

TGKDIIPPKTIAGEVDGTVNIDKQLNNFKNLGYSYVGTDALKAPNYTETS

GTPTLKLTNSSQTVIYKFKDVQ

S. aureus SasA A-domain:
Amino Acid Sequence
                                        (SEQ ID NO: 18)
ASDAPLTSELNTQSETVGNQNSTTIEASTSTADSTSVTKNSSSVQTSNSD

TVSSEKSEKVTSTTNSTSNQQEKLTSTSESTSSKNTTSSSDTKSVASTSS

TEQPINTSTNQSTASNNTSQSTTPSSVNLNKTSTTSTSTAPVKLRTFSRL

AMSTFASAATTTAVTANTITVNKDNLKQYMTTSGNATYDQSTGIVTLTQD

AYSQKGAITLGTRIDSNKSFHFSGKVNLGNKYEGHGNGGDGIGFAFSPGV

LGETGLNGAAVGIGGLSNAFGFKLDTYHNTSKPNSAAKANADPSNVAGGG

AFGAFVTTDSYGVATTYTSSSTADNAAKLNVQPTNNTFQDFDINYNGDTK

VMTVKYAGQTWTRNISDWIAKSGTTNFSLSMTASTGGATNLQQVQFGTFE

YTESAVTQVRYVDVTTGKDIIPPKTYSGNVDQVVTIDNQQSALTAKGYNY

TSVDSSYASTYNDTNKTVKMTNAGQSVTYYFTDVV
```

The entire sequence of the Aap protein and the DNA coding therefor (with an indication of the presence of the A domain) is shown below:

```
S.epidermidis Aap Protein (A-domain underlined)
                                        (SEQ ID NO: 19)
MGKRRQGPINKKVDFLPNKLNKYSIRKFTVGTASILLGSTLIFGSSSHEA

KAAEEKQVDPITQANQNDSSERSLENTNQPTVNNEAPQMSSTLQAEEGSN
```

-continued

AEAPQSEPTKAEEGGNAEAAQSEPTKAEEGGNAEAPQSEPTKAEEGGNAE

AAQSEPTKTEEGSNVKAAQSEPTKAEEGSNAEAPQSEPTKTEEGSNAKAA

QSEPTKAEEGGNAEAAQSEPTKTEEGSNAEAPQSEPTKAEEGGNAEAPQS

EPTKTEEGGNAEAPNVPTIKANSDNDTQTQFSEAPTRNDLARKEDIPAVS

KNEELQSSQPNTDSKIEPTTSEPVNLNYSSPFMSLLSMPADSSSNNTKNT

IDPPTTVKGRDNYDFYGRVDIESNPTDLNATNLTRYNYGQPPGTTTAGAV

QFKNQVSFDKDFDFNIRVANNRQSNTTGADGWGFMFSKKDGDDFLKNGGI

LREKGTPSAAGFRIDTGYYNNDPLDKIQKQAGQGYRGYGTFVKNDSQGNT

SKVGSGTPSTDFLNYADNTTNDLDGKFHGQKLNNVNLKYNASNQTFTATY

AGKTWTATLSELGLSPTDSYNFLVTSSQYGNGNSGTYASGVMRADLDGAT

LTYTPKAVDGDPIISTKEIPFNKKREFDPNLAPGTEKVVQKGEPGIETTT

TPTYVNPNTGEKVGEGEPTEKITKQPVDEIVHYGEEIKPGHKDEFDPNA

PKGSQTTQPGKPGVKNPDTGEVVTPPVDDVTKYGPVDGDPITSTEEIPED

KKREFNPDLKPGEERVKQKGEPGTKTITTPTTKNPLTGEKVGEGEPTEKI

TKQPVDEITEYGGEEIKPGHKDEEDPNAPKGSQEDVPGKPGVKNPGTGEV

VTPPVDDVTKYGPVDGDPITSTEEIPEDKKREFNPDLKPGEERVKQKGEP

GTKTITTPTTKNPLTGEKVGEGEPTEKITKQPVDEIVHYGGEQIPQGHKD

EFDPNAPVDSKTEVPGKPGVKNPDTGEVVTPPVDDVTKYGPVDGDSITST

EEIPFDKKREFDPNLAPGTEKVVQKGEPGTKTITTPTTKNPLTGEKVGEG

KSTEKVTKQPVDEIVEYGPTKAEPGKPAEPGKPAEPGKPAEPGTPAEPGK

PAEPGTPAEPGKPAEPGKPAEPGKPAEPGKPAEPGTPAEPGTPAEPGKPA

EPGTPAEPGKPAEPGTPAEPGKPAESGKPVEPGTPAQSGAPEQPNRSMHS

TDNKNQLPDTGENRQANEGTLVGSLLAIVGSLFIFGRRKKGNEK

S. epidermidis aap DNA (SEQ ID NO: 20)
atgggcaaac gtagacaagg tcctattaat aaaaaagtgg attttttacc taacaaatta aacaagtatt ctataagaaa attcactgtt ggtacggcct caatattact tggttcgaca cttattttg gaagtagtag ccatgaagcg aaagctgcag aagaaaaaca agttgatcca attacacaag ctaatcaaaa tgatagtagt gaaagatcac ttgaaaacac aaatcaacct actgtaaaca atgaagcacc acagatgtct tctacattgc aagcagaaga aggaagcaat gcagaagcac tcaatctga gccaacgaag gcagaagaag gaggcaatgc agaagcagct caatctgagc caacgaaggc agaagaagga ggcaatgcag aagcacctca atctgagcca acgaaggcag aagaaggagg caatgcagaa gcagctcaat ctgagccaac gaagacagaa gaaggaagca acgtaaaagc agctcaatct gagccaacga aggcagaaga aggaagcaat gcagaagcac tcaatctga gccaacgaag acagaagaag gaagcaacgc aaaagcagct caatctgagc caacgaaggc agaagaagga ggcaatgcag aagcagctca atctgagcca acgaagacag aagaaggaag caatgcagaa gcacctcaat ctgagccaac gaaggcagaa gaaggaggca atgcagaagc acctcaatct gagccaacga agacagaaga aggaggcaat gcagaagcac cgaatgttcc aactatcaaa gctaattcag ataatgatac acaaacacaa tttttcagaag cccctacaag aaatgaccta gctagaaaag aagatatccc tgctgtttct aaaaacgagg aattacaatc atcacaacca aacactgaca gtaaaataga acctacaact tcagaacctg tgaatttaaa ttatagttct ccgtttatgt ccttattaag catgcctgct gatagttcat ccaataacac taaaaataca atagatatac cgccaactac ggttaaaggt agagataatt acgattttta cggtagagta gatatcgaaa gtaatcctac agatttaaat gcgacaaatt taacgagata taattatgga cagccacctg gtacaacaac agctggtgca gttcaattta aaaatcaagt tagttttgat aaagatttcg actttaacat tagagtagca aacaatcgtc aaagtaatac aactggtgca gatggttggg gctttatgtt cagcaagaaa gatggggatg atttcctaaa aaacggtggt atcttacgtg aaaaaggtac acctagtgca gctggtttca gaattgatac aggatattat aataacgatc cattagataa aatacagaaa caagctggtc aaggctatag agggtatggg acatttgtta aaaatgactc ccaaggtaat acttctaaag taggatcagg tactccatca acagattttc ttaactacgc agataatact actaatgatt tagatggtaa attccatggt caaaaattaa ataatgttaa tttgaaatat aatgcttcaa atcaaacttt tacagctact tatgctggta aaacttggac ggctacgtta tctgaattag gattgagtcc aactgatagt tacaattttt tagttacatc aagtcaatat ggaaatggta atagtggtac atacgcaagt ggcgttatga gagctgattt agatggtgca acattgacat acactcctaa agcagtcgat ggagatccaa ttatatcaac taaggaaata ccatttaata gaaaacgtga atttgatcca aacttagccc caggtacaga aaaagtagtc caaaaaggtg aaccaggaat tgaaacaaca acaacaccaa cttatgtcaa tcctaataca ggagaaaag ttggcgaagg tgaaccaaca gaaaaaataa caaaacaacc agtggatgaa atcgttcatt atggtggcga agaaatcaag ccaggccata aggatgaatt tgatccaaat gcaccgaaag gtagtcaaac aacgcaacca ggtaagccgg gggttaaaaa tcctgataca ggcgaagtag ttactccacc tgtggatgat gtgacaaaat atggtccagt tgatggagat ccgatcacgt caacgaaga aattccattc gacaagaaac gtgaattcaa tcctgattta -continued

```
aaaccaggtg aagagcgtgt taaacaaaaa ggtgaaccag gaacaaaaac aattacaaca ccaacaacta agaacccatt aacagggaaa aaagttggcg aaggtgaacc aacagaaaaa ataacaaaac aaccagtaga tgaaatcaca gaatatggtg gcgaagaaat caagccaggc cataaggatg aatttgatcc aaatgcaccg aaaggtagcc aagaggacgt tccaggtaaa ccaggagtta aaaaccctgg aacaggcgaa gtagtcacac caccagtgga tgatgtgaca aaatatggtc cagttgatgg agatccgatc acgtcaacgg aagaaattcc attcgacaag aaacgtgaat tcaatcctga tttaaaacca ggtgaagagc gcgttaaaca gaaaggtgaa ccaggaacaa aaacaattac aacgccaaca actaagaacc cattaacagg agaaaaagtt ggcgaaggtg aaccaacaga aaaaataaca aacaaccag tggatgagat tgttcattat ggtggtgaac aaataccaca aggtcataaa gatgaatttg atccaaatgc acctgtagat agtaaaactg aagttccagg taaaccagga gttaaaaatc ctgatacagg tgaagttgtt accccaccag tggatgatgt gacaaaatat ggtccagttg atggagattc gattacgtca acggaagaaa ttccgtttga taaaaaacgc gaatttgatc caaacttagc gccaggtaca gagaaagtcg ttcaaaaagg tgaaccagga acaaaaacaa ttacaacgcc aacaactaag aacccattaa caggagaaaa agttggcgaa ggtaaatcaa cagaaaaagt cactaaacaa cctgttgacg aaattgttga gtatggtcca acaaaagcag aaccaggtaa accagcggaa ccaggtaaac cagcggaacc aggtaaacca gcggaaccag gtacgccagc agaaccaggt aaaccagcgg aaccaggtac gccagcagaa ccaggtaaac cagcggaacc aggtaaacca gcggaaccag gtaaaccagc ggaaccaggt aaaccagcgg aaccaggtac gccagcagaa ccaggtacgc cagcagaacc aggtaaacca gcggaaccag gtacgccagc agaaccaggt aaaccagcgg aaccaggtac gccagcagaa ccaggtaaac cagcggaatc aggtaaacca gtggaaccag gtacgccagc acaatcaggt gcaccagaac aaccaaatag atcaatgcat tcaacgagata taaaaatca attacctgat acaggtgaaa atcgtcaagc taatgaggga actttagtcg gatctctatt agcaattgtc ggatcattgt tcatatttgg tcgtcgtaaa aaaggtaatg aaaaataatt tcatataaaa actttctgcc attaa
```

-continued

A-Domain from *S. epidermidis* Aap (amino acids 55-600)

(SEQ ID NO: 21)

$^{55}$EKQVDPITQANQNDSSERSLENTNQPTVNNEAPQMSSTLQAEEGSNAE

APQSEPTKAEEGGNAEAAQSEPTKAEEGGNAEAPQSEPTKAEEGGNAEAA

QSEPTKTEEGSNVKAAQSEPTKAEEGSNAEAPQSEPTKTEEGSNAKAAQS

EPTKAEEGGNAEAAQSEPTKTEEGSNAEAPQSEPTKAEEGGNAEAPQSEP

TKTEEGGNAEAPNVPTIKANSDNDTQTQFSEAPTRNDLARKEDIPAVSKN

EELQSSQPNTDSKIEPTTSEPVNLNYSSPFMSLLSMPADSSSNNTKNTID

IPPTTVKGRDNYDFYGRVDIESNPTDLNATNLTRYNYGQPPGTTTAGAVQ

FKNQVSFDKDFDFNIRVANNRQSNTTGADGWGFMFSKKDGDDFLKNGGIL

REKGTPSAAGFRIDTGYYNNDPLDKIQKQAGQGYRGYGTFVKNDSQGNTS

KVGSGTPSTDFLNYADNTTNDLDGKFHGQKLNNVNLKYNASNQTFTATYA

GKTWTATLSELGLSPTDSYNFLVTSSQYGNGNSGTYASGVMRADLD

GA$^{600}$

Protein Production and Purification

Using PCR, the A domain of DgsK or SasA was amplified from the sequences described above and subcloned into the *E. Coli* expression vector PQE-30 (Qiagen), which allows for the expression of a recombinant fusion protein containing six histidine residues. This vector was subsequently transformed into the *E. Coli* strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size of 0.45 □m) and the cell paste frozen at −80° C. Cells were lysed in 1×PBS (10 mL of buffer/1 g of cell paste) using 2 passes through the French Press@ 1100 psi.

Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 200 mM imidazole (Buffer B) over 30 column volumes. SdrGN1N2N3 or SdrGN2N3 eluted at ~13% Buffer B (~26 mM imidazole). Absorbance at 280 nm was monitored. Fractions containing SdrGN1N2N3 or SdrGN2N3 were dialyzed in 1×PBS.

Each protein was then put through an endotoxin removal protocol. Buffers used during this protocol were made endotoxin free by passing over a 5-mL Mono-Q sepharose (Pharmacia) column. Protein was divided evenly between 4×15 mL tubes. The volume of each tube was brought to 9 mL with Buffer A. 1 mL of 10% Triton X-114 was added to each tube and incubated with rotation for 1 hour at 4° C. Tubes were placed in a 37° C. water bath to separate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with 0.1M $NiCl_2$ to remove remaining detergent. The column was washed with 9 column volumes of Buffer A before the protein was eluted with 3 column volumes of Buffer B. The eluant was passed over a 5-mL Detoxigel (Sigma) column and the flow-through collected and reapplied to the column. The flow-through from the second pass was collected and dialyzed in 1×PBS. The purified product was analyzed for concentration, purity and endotoxin level before administration into the mice.

Monoclonal Antibody Production

*E. coli* expressed and purified recombinant SasA and DsgK proteins were used to generate a panel of murine monoclonal antibodies while the mouse sera was used as a source of polyclonal antibodies. Briefly, a group of Balb/C or SJL mice received a series of subcutaneous immunizations of 1-10 mg of protein in solution or mixed with adjuvant as described in the Table below.

| Immunization Schemes | | | | |
|---|---|---|---|---|
| | Day | Amount (µg) | Route | Adjuvant |
| RIMMS Injection | | | | |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection | | | | |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against MSCRAMM® proteins or on whole cells (*S. epidermidis* and *S. aureus*). Three days after the final boost, the spleens or lymph nodes were removed, teased into a single cell suspension and the lymphocytes harvested. The lymphocytes were then fused to a P3X63Ag8.653 myeloma cell line (ATCC #CRL-1580). Cell fusion, subsequent plating and feeding were performed according to the Production of Monoclonal Antibodies protocol from *Current Protocols in Immunology* (Chapter 2, Unit 2.).

Any clones that were generated from the fusion were then screened for specific anti-SasA antibody production using a standard ELISA assay. Positive clones were expanded and tested further for activity in a whole bacterial cell binding assay by flow cytometry and SasA binding by Biacore analysis.

Biacore Analysis

Throughout the analysis, the flow rate remained constant at 10 ml/min. Prior to the SasA or DgsK injection, test antibody was adsorbed to the chip via RAM-Fc binding. At time 0, SasA or DgsK at a concentration of 30 mg/ml was injected over the chip for 3 min followed by 2 minutes of dissociation. This phase of the analysis measured the relative association and disassociation kinetics of the Mab/SasA or DgsK interaction.

Binding to Whole Bacteria

Bacterial samples *S. aureus* Newman, *S. aureus* 67-O, *S. aureus* 397 (Sal6), *S. aureus* Wood, *S. aureus* 8325-4, methicillin resistant *S. aureus* MRSA 16, *S. epidermidis* ATCC 35984, *S. epidermidis* HB, *S. epidermidis* CN-899 and *S. haemolyticus* ATCC 43253 were collected, washed and incubated with Mab or PBS alone (control) at a concentration of 2 µg/ml after blocking with rabbit IgG (50 mg/ml). Following incubation with antibody, bacterial cells were incubated with Goat-F$_{(ab')2}$-Anti-Mouse-F$_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured. These data indicate that antibodies against *S. aureus* SasA were able to recognize a homologous protein on the surface of coagulase-negative staphylococci. The data support Western blot analysis demonstrating that rabbit polyclonal antibodies against *S. aureus* SasA cross-react with a protein released from the cell surface of *S. epidermidis* HB as well as the recombinant A-region from DsgK cloned from *S. epidermidis* (see Table below and FIG. 6).

Polyclonal Sera Reactivity

| | New man | 67-O | 397 (SAL 6) | Wood 46 | 8325-4 | MRSA 16 | ATCC 35984 | HB | CN-899 | ATCC 43253 |
|---|---|---|---|---|---|---|---|---|---|---|
| Normal Mouse Sera | − | − | − | − | − | − | − | − | − | − |
| Mouse anti-SasA | + | + | +/− | − | + | + | + | + | + | + |

What is claimed is:

1. A method of inducing an immunological response comprising administering to a human or animal an immunogenic amount of an isolated peptide comprising the amino acid sequence of SEQ ID NO:10.

* * * * *

SEQUENCE LISTING

<160> NUMBER OF SEQ ID NOS: 33

<210> SEQ ID NO 1
<211> LENGTH: 6609
<212> TYPE: DNA
<213> ORGANISM: Staphylococcus epidermidis

<400> SEQUENCE: 1
acaacacagc agagaataga caaccaggag gaaaacgaaa tgaatttgtt aaagaaaaat    60
aaatatagta ttagaaaata taaagtaggg atattctcta ctttaatcgg gacagtttta   120

```
ttactttcaa acccaaatgg tgcacaagct ttaactacgg atcataatgt gcaaggtggt      180
tcaaatcaag cattacctgg caactcacaa atacaaatg ccgatactaa tcgagacata       240
gtaaatgatt cgcaaaatac tcctaatgca catgcaacag acaatacatc aacaaatcaa      300
gcattgacta atcatcaaaa cgttgatgtg gcaaatcaag tcgggcctgc tccaatacag     360
cctagcgcgt cgcctgcgca aaataataat aattctaatg ctaattcaac agcaacagag      420
ccagcggcga atacaaataa taatttagca tcaaataaca atacattaaa cgtgcctaat      480
aatacagata acaatgattc agcgcgtcat ctgactttaa aagaaattca agaagatgtt      540
cgtcattcgt ctgataagcc agagttagtt gcgattgctg aagaagcatc taatagaccg      600
aaaaagagaa gcagacgtgc tgcgccaaca gatcctaatg caacaccagc agatccaacg      660
gctacaccag cagatccaac ggcaggaaat ggtagtgcac cagttgcaat tacagcgcca      720
tacacgccaa caactgatcc caatgccaat aatataggac aaaatgcacc taacgaagtg      780
ctttcatttg atgataacaa cattagacca agtacgaacc gttctgtgcc tacagtaact      840
gttgttgata atttaccagg ctacacactg attaatggtg gtaaagtagg ggtgtttagt      900
catgcaatgg taagaacgag catgtttgat tcaggagatg ccaagaacta tcaagcgcaa      960
ggcaatgtaa ttgcattggg tcgtattaga ggaaatgata caaatgatca tggcgatttt     1020
aatggtatcg agaaaacatt aacagtaaat ccgaattctg aattaatctt tgaatttaat      1080
actatgacta ctaaaaacta tcaaggtatg acaaatttaa tcattaaaaa tgctgataac      1140
gatactgtta ttggtgaaaa agtagttgct tatggtccga tttggcgctt attaaaagta      1200
cctgaaaatg ttagtcatct aaaaattcaa tttgtaccta aaaatgacgc aataacagat      1260
gcacgtggta tttatcaatt acgagatgga tataaatact atgactttgt agactcaatc      1320
ggtcttcatt ctgggtcaca tgtctatgtt gaaagacgta caatggagcc aacagcaaca      1380
aataataaag aatttacagt tacaacgtca ttaaagaata atggtaactt tggcgcttca      1440
ttcaatacag atgattttgt atataaaatt caattacctg aaggtgttga atatgtaaat      1500
aattcattga ctaaagattt tcctagcggt aattcaggtg ttgatattaa tgatatgaat      1560
gtgacgtatg acgcagcaaa tcgaattatt acaattaaaa gtactggtgg aggtacaggg      1620
aattcgccgg cacgactaat gcctgataaa atattggatt tgaagtataa gctacgtgtg      1680
aacaatgtgc caacaccaag aacagtaaca tttaacgata cattaacgta taaaacatat      1740
tcacaagatt ttattaattc acctgctgaa agtcatactg taagtacaaa tccatataca      1800
attgatatca tcatgaataa agacgcattg caagccgaag tcgatagacg aattcaacaa      1860
gcggattata catttgcatc attagatatt tttaatgatc ttaaaagacg cgcacaaaca      1920 atttttagatg aaaaccgtaa caatgtacct ttaaacaaaa gagtttctca agcagatatc     1980
gattcattag caaatcagat gcaacatacg ttaattcgca gtgttgacgc tgaaaatgcc      2040
gttaatagaa aagttgatga catggaagat ttagttaacc aaaatgatga actgacagat      2100
gaagaaaaac aagcagcgat tcaagtcatc gaggaacata aaatgaaat tattgggaat       2160 attggtgacc aaacgactga tgatggcgtt actagaatta aagatcaagg tatacagact      2220
ttaagtggag acactgcaac accagttgtt aaaccaaatg ctaaacaagc tatacgtgat      2280
aaagcagcga acaaagaga aattatcaat cacacgccag atgctactca agatgaaatt       2340
caagatgcat taaatcaatt aacaacggat gaaacagatg ctattgataa tgttacgaat      2400
gctactacca atgctgatgt tgaaacagct aaaaataatg gtattaatac aattggtgca      2460
gttgcgccac aagtgacaca caaacaagct gcaagagatg caattaatca agcgacagca      2520
```

```
acgaaacgac aacaaataaa tagcaataga gaagcaacac aagaagagaa aaatgcagca    2580
ttgaatgaat taacgcaagc cacgaaccac gcattagaac aaatcaatca agcgacaacc    2640
aatgatgatg tagatactgc caaaggtgat ggtctgaatg ccattaatcc tattgcgcct    2700
gtaactgttg tcaagcaagc agcaagagat gccgtatcac atgatgcaca acagcatatc    2760
gcagagatca atgcaaatcc tgatgcgact caagaagaaa gacaagcagc aatagagaaa    2820
gtaaatgctg ctgtagctgt tgcgaatact aatatattaa atgctaatac caatgctgat    2880
gttgagcaag taaagacaaa tgcaattcaa ggtatacaag ccattgaacc agctacaaag    2940
gttaaaacag atgctaaaaa cgctattgat caaagtgcgg aaacgcaaca taatgcgata    3000
tttaataata atgatgcgac cttagaagag caacaagcag cacaacaatt gcttgatcaa    3060
gctgtagcca cagcgaagca aaatattaat gcagcagata cgaatcaaga agttcacaa     3120 gcaaagatc agggcacaca aaatatagtt gtgattcaac cggcaacaca agttaaaacg     3180
gatgcacgca atgctgtaaa tgaaaaagcg cgagaggcga taacaaatat caatgctaca    3240
cctggcgcga ctcgagaaga gaaacaagaa gcgataaatc gtgtcaatac acttaaaaat    3300
agagcattaa atgatattgg tgtgacgtct actactgcga tggtcaatag tattagagac    3360
gatgcagtca atcaaatcgg tgcagttcaa ccgcatgtaa cgaagaaaca aactgctaca    3420
ggtgtattaa cggacttagc aactgcaaaa aaacaagaaa ttaatcaaaa tacaaatgca    3480
accactgaag aaaagcaagt agcattaaat caagtagacc aagatttagc aacggcaatt    3540
aataatataa atcaagctga tactaatgca gaagtagatc aagcacaaca attaggtaca    3600
aaagcaatta atgcgattca gccaaatatt gtaaaaaaac ctgcagcatt agcacaaacc    3660
aatcagcatt atagtgctaa attagttgaa atcaatgcta caccagatgc aacagatgat    3720
gagaaaaatg ctgcgatcaa tactttaaat caagacagac aacaagctat tgaaagtatt    3780
aaacaagcaa atacaaatgc ggaagtagac caagctgcga cagtggcaga gaataatatc    3840
gatgctgttc aagttgacgt tgtaaaaaaa caagcagcgc gagataaaat cactgctgaa    3900
gtagcgaagc gtattgaagc ggttaaacaa acacctaatg caactgacga agaaaagcag    3960
gctgcagtta atcaaatcaa tcaacttaaa gatcaagcgt ttaatcaaat taatcaaaac    4020
caaacaaatg atcaggtaga cgcaactaca aatcaagcga ttaatgctat agataatgtt    4080
gaagctgaag tagtaattaa accaaaggca attgcagata ttgaaaaagc tgttaaagaa    4140
aagcaacagc aaattgataa tagtcttgat tcaacagata tgagaaaga agttgcttta    4200 caagcattag ctaaagaaaa agaaaaagca cttgcagcta ttgaccaagc tcaaacgaat    4260
agtcaggtga atcaagcggc aacaaatggt gtatcagcga ttaaaattat tcaacctgaa    4320
acaaaaatta aaccagcagc acgtgaaaaa atcaatcaaa aagcgaatga attacgtgcg    4380
caaattaatc aagataaaga agcgacagca gaagaaagac aagcggcgtt agataaaatc    4440
aatgatttag ttgctaaagc tatgacaaat atcacgaatg atagaacaaa tcagcaagtt    4500
aatgactcaa caaatcaagc gcttgacgac attgcattag tgacgcctga ccatattgtt    4560
agagcagctg ctagagatgc agttaagcaa caatatgaag ctaaaaagca cgaaattgag    4620
caagcggaac atgcgactga tgaagaaaaa caagttgctt taaatcaatt agcgaataat    4680
gaaaaacgtg cattacaaaa cattaatcaa gcaatagcga ataatgatgt gaaacgtgtt    4740
gaatcaaatg gtattgctac gttaaaaggc gtagaaccgc acattgtggt taaacctgaa    4800
gctcaagaag cccataaagc gagcgcgat aaccaagtag aatctataaa agatacacca    4860
catgctacga cagatgaatt agatgaagca aaccaacaaa taaacgacac acttaaacaa    4920
```

```
ggtcaacaag atatagacaa tacgacacaa gatgcagctg tcaatgatgt tagaaaccaa    4980
acgattaagg caatcgaaca aattaaaccg aaagttagac gcaaacgtgc agcgttggat    5040
aacattgatg aaagtaataa taatcaactc gatgcaatac gaaatacgct agatacaacg    5100
caagatgaac gaaatgttgc tattgctgcg ttaaataaaa ttgttaatgc aattaaaaat    5160
gatattgcac aaaacaaaac gaatgcagaa gtggatcaaa ctgaggctga tggtaacaac    5220
aacatcaaag tgatttttacc taaagttcaa gttaaaccag cagcgcgtca atctgtcagc    5280
gcaaaagctg aagctcaaaa tgcacttatt gatcaaagtg atttatctac gaagaagaa    5340 agattagctg ctaaacattt agtagaacaa gcacttaatc aagctattga tcagatcaat    5400
cacgcagata agactgcgca agttaatcaa aatagtatcg atgctcaaaa tattatttca    5460
aaaattaaac cagcgacaac agttaaagca acagcattac aacaaattca aaatatcgct    5520
acaaataaaa ttaatttaat taaagcaaat aacgaagcga cagatgaaga caaaaatgct    5580
gcaatagtac aagttgaaaa agagttaatt aaagctaaac aacaaattgc tggtgcagtg    5640
actaatgctg atgtggcata tttattgcat gatgggaaaa acgaaattcg tgaaatcgaa    5700
cctgttatta ataaaaaagc aactgcgcga gaacaattaa caacattatt caacgataag    5760
aaacaagcaa ttgaagcgaa tgttcaagca acagtagaag aaagaaatag tattttagca    5820
cagttacaaa acatttatga cactgctatt ggacaaattg atcaagatcg tagcaatgca    5880
caagttgata aaacagcaac attaaatcta caaacaatac atgatttaga cgtacatcct    5940
attaaaaagc cagatgctga aaaaacgatt aatgatgatc ttgcacgtgt tacacattta    6000
gtgcaaaatt atcgaaaagt aagtgatcgt aataaggctg atgcattaaa agctataact    6060
gcattaaaat tacaaatgga tgaagaatta aaaacagcac gcactaatgc tgatgttgat    6120
gcagttttaa aacgatttaa tgttgcatta ggcgatatag aagcagtaat tactgaaaaa    6180
gaaaatagct tactgcgcat tgataacatt gctcaacaaa catatgcgaa attcaaagcg    6240
atcgcaacac cagaacaatt agctaaagta aaagcattaa ttgatcaata tgttgcagat    6300
ggcaatagaa tggttgatga agatgcgaca ttaaatgaca tcaaaaaaga tacgcaactc    6360
attattgatg aaatttttagc aattaaatta cctgctgaag tgataaaagc gtcaccaaaa    6420
gtggggcaac ctgctccaaa agtttgtacg cctattaaaa aagaagataa acaagaagtg    6480
cgaaaagttg taaagaact tccaaatact ggttctgaag aaatggattt accattaaaa    6540
gaattagcac taattacagg cgcagcatta ttagctagaa gacgttctaa aaaagaaaaa    6600
gaatcataa                                                            6609
```

<210> SEQ ID NO 2
<211> LENGTH: 2189
<212> TYPE: PRT
<213> ORGANISM: Staphylococcus epidermidis

<400> SEQUENCE: 2

```
Met Asn Leu Leu Lys Lys Asn Lys Tyr Ser Ile Arg Lys Tyr Lys Val
1               5                   10                  15

Gly Ile Phe Ser Thr Leu Ile Gly Thr Val Leu Leu Ser Asn Pro
                20                  25                  30

Asn Gly Ala Gln Ala Leu Thr Thr Asp His Asn Val Gln Gly Gly Ser
            35                  40                  45

Asn Gln Ala Leu Pro Gly Asn Ser Gln Asn Thr Asn Ala Asp Thr Asn
        50                  55                  60

Arg Asp Ile Val Asn Asp Ser Gln Asn Thr Pro Asn Ala His Ala Thr
```

```
             65                  70                  75                  80
Asp Asn Thr Ser Thr Asn Gln Ala Leu Thr Asn His Gln Asn Val Asp
                     85                  90                  95
Val Ala Asn Gln Val Gly Pro Ala Pro Ile Gln Pro Ser Ala Ser Pro
                100                 105                 110
Ala Gln Asn Asn Asn Asn Ser Asn Ala Asn Ser Thr Ala Thr Glu Pro
            115                 120                 125
Ala Ala Asn Thr Asn Asn Asn Leu Ala Ser Asn Asn Thr Leu Asn
        130                 135                 140
Val Pro Asn Asn Thr Asp Asn Asn Asp Ser Ala Arg His Leu Thr Leu
145                 150                 155                 160
Lys Glu Ile Gln Glu Asp Val Arg His Ser Ser Asp Lys Pro Glu Leu
                165                 170                 175
Val Ala Ile Ala Glu Glu Ala Ser Asn Arg Pro Lys Lys Arg Ser Arg
                180                 185                 190
Arg Ala Ala Pro Thr Asp Pro Asn Ala Thr Pro Ala Asp Pro Thr Ala
            195                 200                 205
Thr Pro Ala Asp Pro Thr Ala Gly Asn Gly Ser Ala Pro Val Ala Ile
        210                 215                 220
Thr Ala Pro Tyr Thr Pro Thr Thr Asp Pro Asn Ala Asn Asn Ile Gly
225                 230                 235                 240
Gln Asn Ala Pro Asn Glu Val Leu Ser Phe Asp Asn Asn Ile Arg
                245                 250                 255
Pro Ser Thr Asn Arg Ser Val Pro Thr Val Thr Val Asp Asn Leu
            260                 265                 270
Pro Gly Tyr Thr Leu Ile Asn Gly Gly Lys Val Gly Val Phe Ser His
        275                 280                 285
Ala Met Val Arg Thr Ser Met Phe Asp Ser Gly Asp Ala Lys Asn Tyr
        290                 295                 300
Gln Ala Gln Gly Asn Val Ile Ala Leu Gly Arg Ile Arg Gly Asn Asp
305                 310                 315                 320
Thr Asn Asp His Gly Asp Phe Asn Gly Ile Glu Lys Thr Leu Thr Val
                325                 330                 335
Asn Pro Asn Ser Glu Leu Ile Phe Glu Phe Asn Thr Met Thr Thr Lys
            340                 345                 350
Asn Tyr Gln Gly Met Thr Asn Leu Ile Ile Lys Asn Ala Asp Asn Asp
        355                 360                 365
Thr Val Ile Gly Glu Lys Val Val Ala Tyr Gly Pro Ile Trp Arg Leu
    370                 375                 380
Leu Lys Val Pro Glu Asn Val Ser His Leu Lys Ile Gln Phe Val Pro
385                 390                 395                 400
Lys Asn Asp Ala Ile Thr Asp Ala Arg Gly Ile Tyr Gln Leu Arg Asp
                405                 410                 415
Gly Tyr Lys Tyr Tyr Asp Phe Val Asp Ser Ile Gly Leu His Ser Gly
            420                 425                 430
Ser His Val Tyr Val Glu Arg Arg Thr Met Glu Pro Thr Ala Thr Asn
        435                 440                 445
Asn Lys Glu Phe Thr Val Thr Thr Ser Leu Lys Asn Asn Gly Asn Phe
    450                 455                 460
Gly Ala Ser Phe Asn Thr Asp Asp Phe Val Tyr Lys Ile Gln Leu Pro
465                 470                 475                 480
Glu Gly Val Glu Tyr Val Asn Asn Ser Leu Thr Lys Asp Phe Pro Ser
                485                 490                 495
```

```
Gly Asn Ser Gly Val Asp Ile Asn Asp Met Asn Val Thr Tyr Asp Ala
            500                 505                 510

Ala Asn Arg Ile Ile Thr Ile Lys Ser Thr Gly Gly Thr Gly Asn
        515                 520                 525

Ser Pro Ala Arg Leu Met Pro Asp Lys Ile Leu Asp Leu Lys Tyr Lys
        530                 535                 540

Leu Arg Val Asn Asn Val Pro Thr Pro Arg Thr Val Thr Phe Asn Asp
545                 550                 555                 560

Thr Leu Thr Tyr Lys Thr Tyr Ser Gln Asp Phe Ile Asn Ser Pro Ala
                565                 570                 575

Glu Ser His Thr Val Ser Thr Asn Pro Tyr Thr Ile Asp Ile Ile Met
            580                 585                 590

Asn Lys Asp Ala Leu Gln Ala Glu Val Asp Arg Arg Ile Gln Gln Ala
        595                 600                 605

Asp Tyr Thr Phe Ala Ser Leu Asp Ile Phe Asn Asp Leu Lys Arg Arg
        610                 615                 620

Ala Gln Thr Ile Leu Asp Glu Asn Arg Asn Asn Val Pro Leu Asn Lys
625                 630                 635                 640

Arg Val Ser Gln Ala Asp Ile Asp Ser Leu Ala Asn Gln Met Gln His
                645                 650                 655

Thr Leu Ile Arg Ser Val Asp Ala Glu Asn Ala Val Asn Arg Lys Val
            660                 665                 670

Asp Asp Met Glu Asp Leu Val Asn Gln Asn Asp Glu Leu Thr Asp Glu
        675                 680                 685

Glu Lys Gln Ala Ala Ile Gln Val Ile Glu Glu His Lys Asn Glu Ile
        690                 695                 700

Ile Gly Asn Ile Gly Asp Gln Thr Thr Asp Asp Gly Val Thr Arg Ile
705                 710                 715                 720

Lys Asp Gln Gly Ile Gln Thr Leu Ser Gly Asp Thr Ala Thr Pro Val
                725                 730                 735

Val Lys Pro Asn Ala Lys Gln Ala Ile Arg Asp Lys Ala Ala Lys Gln
            740                 745                 750

Arg Glu Ile Ile Asn His Thr Pro Asp Ala Thr Gln Asp Glu Ile Gln
        755                 760                 765

Asp Ala Leu Asn Gln Leu Thr Thr Asp Glu Thr Asp Ala Ile Asp Asn
        770                 775                 780

Val Thr Asn Ala Thr Thr Asn Ala Asp Val Glu Thr Ala Lys Asn Asn
785                 790                 795                 800

Gly Ile Asn Thr Ile Gly Ala Val Ala Pro Gln Val Thr His Lys Gln
                805                 810                 815

Ala Ala Arg Asp Ala Ile Asn Gln Ala Thr Ala Thr Lys Arg Gln Gln
            820                 825                 830

Ile Asn Ser Asn Arg Glu Ala Thr Gln Glu Glu Lys Asn Ala Ala Leu
        835                 840                 845

Asn Glu Leu Thr Gln Ala Thr Asn His Ala Leu Glu Gln Ile Asn Gln
        850                 855                 860

Ala Thr Thr Asn Asp Asp Val Asp Thr Ala Lys Gly Asp Gly Leu Asn
865                 870                 875                 880

Ala Ile Asn Pro Ile Ala Pro Val Thr Val Lys Gln Ala Ala Arg
                885                 890                 895

Asp Ala Val Ser His Asp Ala Gln Gln His Ile Ala Glu Ile Asn Ala
            900                 905                 910

Asn Pro Asp Ala Thr Gln Glu Glu Arg Gln Ala Ala Ile Glu Lys Val
        915                 920                 925
```

```
Tyr Ala Ala Val Ala Val Ala Asn Thr Asn Ile Leu Asn Ala Asn Thr
    930             935                 940

Asn Ala Asp Val Glu Gln Val Lys Thr Asn Ala Ile Gln Gly Ile Gln
945             950                 955                 960

Ala Ile Glu Pro Ala Thr Lys Val Lys Thr Asp Ala Lys Asn Ala Ile
                965                 970                 975

Asp Gln Ser Ala Glu Thr Gln His Asn Ala Ile Phe Asn Asn Asn Asp
            980                 985                 990

Ala Thr Leu Glu Glu Gln Gln Ala Ala Gln Gln Leu Leu Asp Gln Ala
        995                 1000                1005

Val Ala Thr Ala Lys Gln Asn Ile Asn Ala Ala Asp Thr Asn Gln
    1010                1015                1020

Glu Val Ala Gln Ala Lys Asp Gln Gly Thr Gln Asn Ile Val Val
    1025                1030                1035

Ile Gln Pro Ala Thr Gln Val Lys Thr Asp Ala Arg Asn Ala Val
    1040                1045                1050

Asn Glu Lys Ala Arg Glu Ala Ile Thr Asn Ile Asn Ala Thr Pro
    1055                1060                1065

Gly Ala Thr Arg Glu Glu Lys Gln Glu Ala Ile Asn Arg Val Asn
    1070                1075                1080

Thr Leu Lys Asn Arg Ala Leu Asn Asp Ile Gly Val Thr Ser Thr
    1085                1090                1095

Thr Ala Met Val Asn Ser Ile Arg Asp Asp Ala Val Asn Gln Ile
    1100                1105                1110

Gly Ala Val Gln Pro His Val Thr Lys Lys Gln Thr Ala Thr Gly
    1115                1120                1125

Val Leu Thr Asp Leu Ala Thr Ala Lys Lys Gln Glu Ile Asn Gln
    1130                1135                1140

Asn Thr Asn Ala Thr Thr Glu Glu Lys Gln Val Ala Leu Asn Gln
    1145                1150                1155

Val Asp Gln Asp Leu Ala Thr Ala Ile Asn Asn Ile Asn Gln Ala
    1160                1165                1170

Asp Thr Asn Ala Glu Val Asp Gln Ala Gln Gln Leu Gly Thr Lys
    1175                1180                1185

Ala Ile Asn Ala Ile Gln Pro Asn Ile Val Lys Lys Pro Ala Ala
    1190                1195                1200

Leu Ala Gln Thr Asn Gln His Tyr Ser Ala Lys Leu Val Glu Ile
    1205                1210                1215

Asn Ala Thr Pro Asp Ala Thr Asp Asp Glu Lys Asn Ala Ala Ile
    1220                1225                1230

Asn Thr Leu Asn Gln Asp Arg Gln Gln Ala Ile Glu Ser Ile Lys
    1235                1240                1245

Gln Ala Asn Thr Asn Ala Glu Val Asp Gln Ala Ala Thr Val Ala
    1250                1255                1260

Glu Asn Asn Ile Asp Ala Val Gln Val Asp Val Val Lys Lys Gln
    1265                1270                1275

Ala Ala Arg Asp Lys Ile Thr Ala Glu Val Ala Lys Arg Ile Glu
    1280                1285                1290

Ala Val Lys Gln Thr Pro Asn Ala Thr Asp Glu Glu Lys Gln Ala
    1295                1300                1305

Ala Val Asn Gln Ile Asn Gln Leu Lys Asp Gln Ala Phe Asn Gln
    1310                1315                1320

Ile Asn Gln Asn Gln Thr Asn Asp Gln Val Asp Ala Thr Thr Asn
```

-continued

```
            1325                1330                1335

Gln Ala Ile Asn Ala Ile Asp Asn Val Glu Ala Glu Val Val Ile
   1340                1345                1350

Lys Pro Lys Ala Ile Ala Asp Ile Glu Lys Ala Val Lys Glu Lys
   1355                1360                1365

Gln Gln Gln Ile Asp Asn Ser Leu Asp Ser Thr Asp Asn Glu Lys
   1370                1375                1380

Glu Val Ala Leu Gln Ala Leu Ala Lys Glu Lys Glu Lys Ala Leu
   1385                1390                1395

Ala Ala Ile Asp Gln Ala Gln Thr Asn Ser Gln Val Asn Gln Ala
   1400                1405                1410

Ala Thr Asn Gly Val Ser Ala Ile Lys Ile Ile Gln Pro Glu Thr
   1415                1420                1425

Lys Ile Lys Pro Ala Ala Arg Glu Lys Ile Asn Gln Lys Ala Asn
   1430                1435                1440

Glu Leu Arg Ala Gln Ile Asn Gln Asp Lys Glu Ala Thr Ala Glu
   1445                1450                1455

Glu Arg Gln Ala Ala Leu Asp Lys Ile Asn Asp Leu Val Ala Lys
   1460                1465                1470

Ala Met Thr Asn Ile Thr Asn Asp Arg Thr Asn Gln Gln Val Asn
   1475                1480                1485

Asp Ser Thr Asn Gln Ala Leu Asp Asp Ile Ala Leu Val Thr Pro
   1490                1495                1500

Asp His Ile Val Arg Ala Ala Arg Asp Ala Val Lys Gln Gln
   1505                1510                1515

Tyr Glu Ala Lys Lys His Glu Ile Glu Gln Ala Glu His Ala Thr
   1520                1525                1530

Asp Glu Glu Lys Gln Val Ala Leu Asn Gln Leu Ala Asn Asn Glu
   1535                1540                1545

Lys Arg Ala Leu Gln Asn Ile Asn Gln Ala Ile Ala Asn Asn Asp
   1550                1555                1560

Val Lys Arg Val Glu Ser Asn Gly Ile Ala Thr Leu Lys Gly Val
   1565                1570                1575

Glu Pro His Ile Val Val Lys Pro Glu Ala Gln Glu Ala Ile Lys
   1580                1585                1590

Ala Ser Ala Asp Asn Gln Val Glu Ser Ile Lys Asp Thr Pro His
   1595                1600                1605

Ala Thr Thr Asp Glu Leu Asp Glu Ala Asn Gln Gln Ile Asn Asp
   1610                1615                1620

Thr Leu Lys Gln Gly Gln Gln Asp Ile Asp Asn Thr Thr Gln Asp
   1625                1630                1635

Ala Ala Val Asn Asp Val Arg Asn Gln Thr Ile Lys Ala Ile Glu
   1640                1645                1650

Gln Ile Lys Pro Lys Val Arg Arg Lys Arg Ala Ala Leu Asp Asn
   1655                1660                1665

Ile Asp Glu Ser Asn Asn Asn Gln Leu Asp Ala Ile Arg Asn Thr
   1670                1675                1680

Leu Asp Thr Thr Gln Asp Glu Arg Asn Val Ala Ile Ala Ala Leu
   1685                1690                1695

Asn Lys Ile Val Asn Ala Ile Lys Asn Asp Ile Ala Gln Asn Lys
   1700                1705                1710

Thr Asn Ala Glu Val Asp Gln Thr Glu Ala Asp Gly Asn Asn Asn
   1715                1720                1725
```

-continued

| | | | | | | | | | | | |
|---|---|---|---|---|---|---|---|---|---|---|---|
| Ile | Lys | Val | Ile | Leu | Pro | Lys | Val | Gln | Val | Lys | Pro | Ala | Ala | Arg |
| | 1730 | | | | 1735 | | | | 1740 | | |
| Gln | Ser | Val | Ser | Ala | Lys | Ala | Glu | Ala | Gln | Asn | Ala | Leu | Ile | Asp |
| | 1745 | | | | 1750 | | | | 1755 | | |
| Gln | Ser | Asp | Leu | Ser | Thr | Glu | Glu | Arg | Leu | Ala | Ala | Lys | His |
| | 1760 | | | | 1765 | | | | 1770 | | |
| Leu | Val | Glu | Gln | Ala | Leu | Asn | Gln | Ala | Ile | Asp | Gln | Ile | Asn | His |
| | 1775 | | | | 1780 | | | | 1785 | | |
| Ala | Asp | Lys | Thr | Ala | Gln | Val | Asn | Gln | Asn | Ser | Ile | Asp | Ala | Gln |
| | 1790 | | | | 1795 | | | | 1800 | | |
| Asn | Ile | Ile | Ser | Lys | Ile | Lys | Pro | Ala | Thr | Thr | Val | Lys | Ala | Thr |
| | 1805 | | | | 1810 | | | | 1815 | | |
| Ala | Leu | Gln | Gln | Ile | Gln | Asn | Ile | Ala | Thr | Asn | Lys | Ile | Asn | Leu |
| | 1820 | | | | 1825 | | | | 1830 | | |
| Ile | Lys | Ala | Asn | Asn | Glu | Ala | Thr | Asp | Glu | Glu | Gln | Asn | Ala | Ala |
| | 1835 | | | | 1840 | | | | 1845 | | |
| Ile | Val | Gln | Val | Glu | Lys | Glu | Leu | Ile | Lys | Ala | Lys | Gln | Gln | Ile |
| | 1850 | | | | 1855 | | | | 1860 | | |
| Ala | Gly | Ala | Val | Thr | Asn | Ala | Asp | Val | Ala | Tyr | Leu | Leu | His | Asp |
| | 1865 | | | | 1870 | | | | 1875 | | |
| Gly | Lys | Asn | Glu | Ile | Arg | Glu | Ile | Glu | Pro | Val | Ile | Asn | Lys | Lys |
| | 1880 | | | | 1885 | | | | 1890 | | |
| Ala | Thr | Ala | Arg | Glu | Gln | Leu | Thr | Thr | Leu | Phe | Asn | Asp | Lys | Lys |
| | 1895 | | | | 1900 | | | | 1905 | | |
| Gln | Ala | Ile | Glu | Ala | Asn | Val | Gln | Ala | Thr | Val | Glu | Glu | Arg | Asn |
| | 1910 | | | | 1915 | | | | 1920 | | |
| Ser | Ile | Leu | Ala | Gln | Leu | Gln | Asn | Ile | Tyr | Asp | Thr | Ala | Ile | Gly |
| | 1925 | | | | 1930 | | | | 1935 | | |
| Gln | Ile | Asp | Gln | Asp | Arg | Ser | Asn | Ala | Gln | Val | Asp | Lys | Thr | Ala |
| | 1940 | | | | 1945 | | | | 1950 | | |
| Thr | Leu | Asn | Leu | Gln | Thr | Ile | His | Asp | Leu | Asp | Val | His | Pro | Ile |
| | 1955 | | | | 1960 | | | | 1965 | | |
| Lys | Lys | Pro | Asp | Ala | Glu | Lys | Thr | Ile | Asn | Asp | Asp | Leu | Ala | Arg |
| | 1970 | | | | 1975 | | | | 1980 | | |
| Val | Thr | His | Leu | Val | Gln | Asn | Tyr | Arg | Lys | Val | Ser | Asp | Arg | Asn |
| | 1985 | | | | 1990 | | | | 1995 | | |
| Lys | Ala | Asp | Ala | Leu | Lys | Ala | Ile | Thr | Ala | Leu | Lys | Leu | Gln | Met |
| | 2000 | | | | 2005 | | | | 2010 | | |
| Asp | Glu | Glu | Leu | Lys | Thr | Ala | Arg | Thr | Asn | Ala | Asp | Val | Asp | Ala |
| | 2015 | | | | 2020 | | | | 2025 | | |
| Val | Leu | Lys | Arg | Phe | Asn | Val | Ala | Leu | Gly | Asp | Ile | Glu | Ala | Val |
| | 2030 | | | | 2035 | | | | 2040 | | |
| Ile | Thr | Glu | Lys | Glu | Asn | Ser | Leu | Leu | Arg | Ile | Asp | Asn | Ile | Ala |
| | 2045 | | | | 2050 | | | | 2055 | | |
| Gln | Gln | Thr | Tyr | Ala | Lys | Phe | Lys | Ala | Ile | Ala | Thr | Pro | Glu | Gln |
| | 2060 | | | | 2065 | | | | 2070 | | |
| Leu | Ala | Lys | Val | Lys | Ala | Leu | Ile | Asp | Gln | Tyr | Val | Ala | Asp | Gly |
| | 2075 | | | | 2080 | | | | 2085 | | |
| Asn | Arg | Met | Val | Asp | Glu | Asp | Ala | Thr | Leu | Asn | Asp | Ile | Lys | Lys |
| | 2090 | | | | 2095 | | | | 2100 | | |
| Asp | Thr | Gln | Leu | Ile | Ile | Asp | Glu | Ile | Leu | Ala | Ile | Lys | Leu | Pro |
| | 2105 | | | | 2110 | | | | 2115 | | |
| Ala | Glu | Val | Ile | Lys | Ala | Ser | Pro | Lys | Val | Gly | Gln | Pro | Ala | Pro |
| | 2120 | | | | 2125 | | | | 2130 | | |

```
Lys Val Cys Thr Pro Ile Lys Glu Asp Lys Gln Glu Val Arg
    2135                2140                2145

Lys Val Val Lys Glu Leu Pro Asn Thr Gly Ser Glu Glu Met Asp
2150                2155                2160

Leu Pro Leu Lys Glu Leu Ala Leu Ile Thr Gly Ala Ala Leu Leu
    2165                2170                2175

Ala Arg Arg Arg Ser Lys Lys Glu Lys Glu Ser
    2180                2185

<210> SEQ ID NO 3
<211> LENGTH: 6852
<212> TYPE: DNA
<213> ORGANISM: Staphylococcus epidermidis

<400> SEQUENCE: 3
```

| | | | | | |
|---|---|---|---|---|---|
| tctaatgaat | gtaaagataa | tacaaggagt | tattacatga | gtaaaagaca | gaaagcattt | 60 |
| catgacagct | tagcaaacga | aaaaacaaga | gtaagacttt | ataaatctgg | aaaaaattgg | 120 |
| gtaaaatccg | gaattaaaga | aatagaaatg | ttcaaaatta | tggggctacc | atttattagt | 180 |
| catagtttag | tgagtcaaga | taatcaaagc | attagtaaaa | aatgacggg | atacggactg | 240 |
| aaaactacgg | cggttattgg | tggtgcattc | acggtaaata | tgttgcatga | ccagcaagct | 300 |
| tttgcggctt | ctgatgcacc | attaacttct | gaattaaaca | cacaaagtga | aacagtaggt | 360 |
| aatcaaaact | caacgacaat | cgaagcatca | acatcaacag | ccgattccac | aagtgtaacg | 420 |
| aaaaatagta | gttcggtaca | aacatcaaat | agtgacacag | tctcaagtga | aaagtctgaa | 480 |
| aaggtcactt | cgacaactaa | tagtacaagc | aatcaacaag | agaaattgac | atctacatca | 540 |
| gaatcaacat | cctcaaagaa | tactacatca | agttctgata | ctaaatctgt | agcttcaact | 600 |
| tcaagtacag | aacaaccaat | taatacatca | acaaatcaaa | gtactgcatc | aaataacact | 660 |
| tcacaaagca | caacgccatc | ttcggtcaac | ttaaacaaaa | ctagcacaac | gtcaactagc | 720 |
| accgcaccag | taaaacttcg | aactttcagt | cgcttagcta | tgtcaacatt | tgcgtcagca | 780 |
| gcgacgacaa | ccgcagtaac | tgctaataca | attacagtta | ataaagataa | cttaaaacaa | 840 |
| tatatgacaa | cgtcaggtaa | tgctacctat | gatcaaagta | ccggtattgt | gacgttaaca | 900 |
| caggatgcat | acagccaaaa | aggtgctatt | acattaggaa | cacgtattga | ctctaataag | 960 |
| agttttcatt | tttctggaaa | agtaaattta | ggtaacaaat | atgaagggca | tggaaatggt | 1020 |
| ggagatggta | tcggttttgc | cttttcacca | ggtgtattag | gtgaaacagg | gttaaacggt | 1080 |
| gccgcagtag | gtattggtgg | cttaagtaac | gcatttggct | tcaaattgga | tacgtatcac | 1140 |
| aatacatcta | aaccaaattc | agctgcaaag | gcgaatgctg | acccatctaa | tgtagctggt | 1200 |
| ggaggtgcgt | ttggtgcatt | tgtaacaaca | gatagttatg | gtgttgcgac | aacgtataca | 1260 |
| tcaagttcaa | cagctgataa | tgctgcgaag | ttaaatgttc | aacctacaaa | taacacgttc | 1320 |
| caagattttg | atattaacta | taatggtgat | acaaaggtta | tgactgtcaa | atatgcaggt | 1380 |
| caaacatgga | cacgtaatat | ttcagattgg | attgcgaaaa | gtggtacgac | caacttttca | 1440 |
| ttatcaatga | cagcctcaac | aggtggcgcg | acaaatttac | aacaagtaca | atttggaaca | 1500 |
| ttcgaatata | cagagtctgc | tgttacacaa | gtgagatacg | ttgatgtaac | aacaggtaaa | 1560 |
| gatattattc | caccaaaaac | atattcagga | aatgttgatc | aagtcgtgac | aatcgataat | 1620 |
| cagcaatctg | cattgactgc | taaaggatat | aactacacgt | ccgtcgatag | ttcatatgcg | 1680 |
| tcaacttata | atgatacaaa | taaaactgta | aaaatgacga | atgctggaca | atcagtgaca | 1740 |
| tattatttta | ctgatgtaaa | agcaccaact | gtaactgtag | gcaatcaaac | catagaagtg | 1800 |

```
ggtaaaacaa tgaatcctat tgtattgact acaacggata atggtactgg gactgtgaca    1860
aatacagtta caggattacc aagcggatta agttacgata gtgcaacgaa ttcaatcatt    1920
gggacaccaa caaaaattgg tcaatcaaca gtgacagttg tgtctactga ccaagcaaat    1980
aacaaatcga cgacaacttt tacaataaat gttgtggata cgacagcacc aacagtgaca    2040
ccaataggag atcaatcatc agaagtgtat tcaccaatat ccccgattaa aattgctacg    2100
caagataaca gtggaaatgc ggtgacgaat acagtgactg gattgccatc cggactaaca    2160
tttgatagta caaataatac tattagtggt acaccaacaa acattggtac aagtactata    2220
tcaatcgttt ctacagatgc gagcggtaac aaaacgacga caacttttaa atatgaagta    2280
acaagaaata gcatgagtga ttccgtatca acatcaggaa gtacacaaca atctcaaagt    2340
gtgtcaacaa gtaaagctga ctcacaaagt gcatcaacga gtacatcagg atcgattgtg    2400
gtatctacat cagctagtac ctcgaaatcg acaagtgtaa gcctatctga ttctgtgagt    2460
gcatctaagt cattaagcac atctgaaagt aatagtgtat caagctcaac aagcacaagt    2520
ttagtgaatt cacaaagtgt atcatcaagc atgtcggatt cagctagtaa atcaacatca    2580
ttaagcgatt ctatttcaaa ctctagcagt actgaaaaat ccgaaagtct atcaacaagt    2640
acatctgatt cattgcgtac atcaacatca ctcagtgact cattaagtat gagtacatca    2700
ggaagcttgt ctaagtcaca aagcttatca acgagtatat cagggtcgtc tagtacatca    2760
gcatcattaa gtgacagtac atcgaatgca attagtacat caacatcatt gagcgagtca    2820
gctagcacct cggactctat cagtatttca aatagcatag ccaactctca aagtgcgtca    2880
acaagcaaat cagattcaca aagtacatca atatcattaa gtacaagtga ttcaaaatcg    2940
atgagtacat cagaatcatt gagcgattcg acgagcacaa gtggttctgt ttctggatca    3000
ctaagcatag cagcatcaca aagtgtctca acaagtacat cagactcgat gagtacttca    3060
gagatagtaa gtgactctat cagtacaagt gggtcattat ctgcatcaga cagtaaatca    3120
atgtccgtaa gtagttcaat gagcacgtct cagtcaggta gtacatcaga atcattaagt    3180
gattcacaaa gtacatctga ttctgatagt aagtcattat cacaaagtac tagtcaatca    3240
ggttcaacaa gtacatcaac gtcgacaagt gcttcagtac gtacttcgga atcacaaagt    3300
acgtctggtt caatgagtgc aagtcaatcc gattcaatga gcatatcaac gtcgtttagt    3360
gattcaacga gtgatagcaa atcagcatca actgcatcaa gtgaatcaat atcacaaagt    3420
gcttctacga gcacatctgg ttcggtaagt acttcgacat cgttaagtac aagtaattca    3480
gaacgtacat caacatctat gagtgattcc acaagcttaa gtacatcaga gtctgattca    3540
ataagtgaat caacgtcaac gagcgactct ataagtgaag caatatctgc ttcagagagc    3600
acgtttatat cattaagtga atcaaatagt actagcgatt cagaatcaca aagtgcatct    3660 gccttttaa gtgaatcatt aagtgaaagt acgtctgaat caacatcaga gtcagtgagt    3720
agttcgacaa gtgagagtac gtcattatca gacagtacat cagaatctgg tagcacatca    3780
acatcattaa gtaattcaac aagtggtagt acgtccattt caacatcgac aagtatcagt    3840
gaatcaacgt caacgtttaa gagcgagagt gtttcaacat cactgagtat gtcaacgagt    3900
acaagtttgt ctgactctac aagtttgtca acatcattaa gtgattccac aagtgatagt    3960
aagtctgatt cattaagtac atcaatgtcg acaagtgatt caatcagtac aagtaaatct    4020
gattccatta gtacatccac atcattaagt ggttctacaa gtgaaagtga atccgactca    4080
acatcatcaa gtgaaagtaa atccgattca acatcaatga gcataagtat gtctcaatca    4140
acatcaggaa gtacaagtac gtcaacgagt acaagtttgt ctgactcaac gagtacatca    4200
```

```
ttgtcactaa gtgcctcaat gaatcaaagc ggagtagact caaactcagc aagccaaagt    4260
gcctcaaact caacaagtac aagcacgagc gaatccgatt cacaaagcac atcatcatat    4320
acaagtcagt caacaagcca aagtgaatcc acatcgacat caacgtcact aagcgattca    4380
acaagtatat ctaaaagtac gagtcaatca ggttcggtaa gcacatcagc gtcattaagt    4440
ggttcagaga gtgaatctga ttcacaaagt atctcaacaa gtgcaagtga gtcaacatca    4500
gaaagtgcgt caacatcact cagtgactca acaagtacaa gtaactcagg atcagcaagt    4560
acgtcaacat cgctcagtaa ctcagcaagc gcaagtgaat ccgatttgtc gtcaacatct    4620
ttaagtgatt caacatctgc gtcaatgcaa agcagtgaat ccgattcaca aagcacatca    4680
gcatcattaa gtgattcgct aagtacatca acttcaaacc gcatgtcgac cattgcaagt    4740
ttatctacat cggtaagtac atcagagtct ggctcaacat cagaaagtac aagtgaatcc    4800
gattcaacat caacatcatt aagcgattca caaagcacat caagaagtac aagtgcatca    4860
ggatcagcaa gtacatcaac atcaacaagt gactctcgta gtacatcagc ttcaactagt    4920
acttcgatgc gtacaagtac tagtgattca caaagtatgt cgctttcgac aagtacatca    4980
acaagtatga gtgattcaac gtcattatct gatagtgtta gtgattcaac atcagactca    5040
acaagtgcga gtacatctgg ttcgatgagt gtgtctatat cgttaagtga ttcgacaagt    5100
acatcaacat cggctagtga agtaatgagc gcaagcatat ctgattcaca agtatgtca    5160 gaatctgtaa atgattcaga aagtgtaagt gaatctaatt ctgaaagtga ctctaaatcg    5220
atgagtggct caacaagtgt cagtgattct ggctcattga gcgtctcaac gtcattaaga    5280
aaatcagaaa gtgtaagcga gtcaagttca ttgagttgct cacaatcgat gagcgattca    5340
gtaagcacaa gcgattcgtc atcattaagt gtatcgacgt cactaagaag ttcagaaagc    5400
gtgagtgaat ctgattcatt aagtgattca aaatcaacaa gtggttcgac ttcaacaagt    5460
acatctggtt cattgagtac ctcaacatca ttaagtggtt cagaaagcgt aagcgagtct    5520
acctcgctaa gtgattcaat atcaatgagt gattctacta gtacaagtga ctccgactca    5580
ttaagtggat caatatcttt aagtggttcc acaagtctta gcacttcgga ttcattaagt    5640
gattcaaaat cattgagtag ctcgcaaagt atgagtggat cagaatcaac gtcaacaagt    5700
gtgagcgatt cgcagtcaag ctcaacaagt aatagtcaat ttgactctat gagcatcagt    5760
gcatcagaaa gcgactcaat gtctacaagt gattcgtcta gcatcagtgg atcaaattca    5820
acgagtacat cactttcaac atctgactca atgagcggaa gcgtatcagt ttcaacatcg    5880
acaagtttaa gtgactcaat atcaggttca acaagtgtaa gtgactcgag ctcaacaagc    5940
acatctacat cattaagtga ttcaatgtca caaagccagt caacaagtac aagtgcatct    6000
ggttccttaa gtacatcgat atcaacatca atgtcaatga gtgctagtac atcgtcatca    6060
caaagcacat cggtgtcgac atcattatca acatcagaca gtatcagtga ttctacttca    6120
ataagtatca gtggttcaca aagtacagta gaatcagaat ctacaagtga ttcaacttct    6180
atcagtgact cagaatcatt gagtacatca gattcagact cgacatcgac aagtacatcg    6240
gactcaacaa gtggttcaac ttcaacaagc atatctgaat cattaagtac gtctggttca    6300
ggttcaacga gcgtatctga ctcaacatca atgagtgaat ctaattcatc gagtgtttca    6360
atgtcacaag acaaatccga ctcaacatca attagtgact cagaatcagt gtcaacaagc    6420
acatcaacgt cattgagcac atccgattcg acaagcacat ccgaatcact gagtacatct    6480
atgtctggtt cacaaagcat ttctgactca acatcaacaa gtatgtccgg ctcaacaagt    6540
acatctgaat ctaactcaat gcatccgtca gactcaatga gtatgcatca tactcacagc    6600
```

-continued

```
acgagcacat ctcgcttatc aagtgaagca acaacgagca cgagtgaatc tcagtctaca    6660
ttaagtgcaa catctgaagt gactaaacat aatggcacac cagcacaaag tgaaaaaaga    6720
ttgccagata caggtgactc aataaaacaa aatggattac taggtggcgt tatgacatta    6780
ttagttggtt taggtttaat gaagagaaag aaaaagaaag atgaaaatga tcaagatgat    6840
tctcaagcat aa                                                        6852

<210> SEQ ID NO 4
<211> LENGTH: 2283
<212> TYPE: PRT
<213> ORGANISM: Staphylococcus epidermidis

<400> SEQUENCE: 4

Ser Asn Glu Cys Lys Asp Asn Thr Arg Ser Tyr Tyr Met Ser Lys Arg
1               5                   10                  15

Gln Lys Ala Phe His Asp Ser Leu Ala Asn Glu Lys Thr Arg Val Arg
            20                  25                  30

Leu Tyr Lys Ser Gly Lys Asn Trp Val Lys Ser Gly Ile Lys Glu Ile
        35                  40                  45

Glu Met Phe Lys Ile Met Gly Leu Pro Phe Ile Ser His Ser Leu Val
    50                  55                  60

Ser Gln Asp Asn Gln Ser Ile Ser Lys Lys Met Thr Gly Tyr Gly Leu
65                  70                  75                  80

Lys Thr Thr Ala Val Ile Gly Gly Ala Phe Thr Val Asn Met Leu His
                85                  90                  95

Asp Gln Gln Ala Phe Ala Ala Ser Asp Ala Pro Leu Thr Ser Glu Leu
            100                 105                 110

Asn Thr Gln Ser Glu Thr Val Gly Asn Gln Asn Ser Thr Thr Ile Glu
        115                 120                 125

Ala Ser Thr Ser Thr Ala Asp Ser Thr Ser Val Thr Lys Asn Ser Ser
    130                 135                 140

Ser Val Gln Thr Ser Asn Ser Asp Thr Val Ser Ser Glu Lys Ser Glu
145                 150                 155                 160

Lys Val Thr Ser Thr Thr Asn Ser Thr Ser Asn Gln Gln Glu Lys Leu
                165                 170                 175

Thr Ser Ser Glu Ser Thr Ser Ser Lys Asn Thr Thr Ser Ser Ser
            180                 185                 190

Asp Thr Lys Ser Val Ala Ser Thr Ser Ser Thr Glu Gln Pro Ile Asn
        195                 200                 205

Thr Ser Thr Asn Gln Ser Thr Ala Ser Asn Asn Thr Ser Gln Ser Thr
    210                 215                 220

Thr Pro Ser Ser Val Asn Leu Asn Lys Thr Ser Thr Thr Ser Thr Ser
225                 230                 235                 240

Thr Ala Pro Val Lys Leu Arg Thr Phe Ser Arg Leu Ala Met Ser Thr
                245                 250                 255

Phe Ala Ser Ala Ala Thr Thr Ala Val Thr Ala Asn Thr Ile Thr
            260                 265                 270

Val Asn Lys Asp Asn Leu Lys Gln Tyr Met Thr Thr Ser Gly Asn Ala
        275                 280                 285

Thr Tyr Asp Gln Ser Thr Gly Ile Val Thr Leu Thr Gln Asp Ala Tyr
    290                 295                 300

Ser Gln Lys Gly Ala Ile Thr Leu Gly Thr Arg Ile Asp Ser Asn Lys
305                 310                 315                 320

Ser Phe His Phe Ser Gly Lys Val Asn Leu Gly Asn Lys Tyr Glu Gly
```

```
                    325                 330                 335
His Gly Asn Gly Gly Asp Gly Ile Gly Phe Ala Phe Ser Pro Gly Val
                340                 345                 350

Leu Gly Glu Thr Gly Leu Asn Gly Ala Ala Val Gly Ile Gly Gly Leu
            355                 360                 365

Ser Asn Ala Phe Gly Phe Lys Leu Asp Thr Tyr His Asn Thr Ser Lys
        370                 375                 380

Pro Asn Ser Ala Ala Lys Ala Asn Ala Asp Pro Ser Asn Val Ala Gly
385                 390                 395                 400

Gly Gly Ala Phe Gly Ala Phe Val Thr Thr Asp Ser Tyr Gly Val Ala
                405                 410                 415

Thr Thr Tyr Thr Ser Ser Thr Ala Asp Asn Ala Ala Lys Leu Asn
                420                 425                 430

Val Gln Pro Thr Asn Asn Thr Phe Gln Asp Phe Asp Ile Asn Tyr Asn
            435                 440                 445

Gly Asp Thr Lys Val Met Thr Val Lys Tyr Ala Gly Gln Thr Trp Thr
        450                 455                 460

Arg Asn Ile Ser Asp Trp Ile Ala Lys Ser Gly Thr Thr Asn Phe Ser
465                 470                 475                 480

Leu Ser Met Thr Ala Ser Thr Gly Ala Thr Asn Leu Gln Gln Val
                485                 490                 495

Gln Phe Gly Thr Phe Glu Tyr Thr Glu Ser Ala Val Thr Gln Val Arg
            500                 505                 510

Tyr Val Asp Val Thr Thr Gly Lys Asp Ile Ile Pro Pro Lys Thr Tyr
        515                 520                 525

Ser Gly Asn Val Asp Gln Val Val Thr Ile Asp Asn Gln Gln Ser Ala
530                 535                 540

Leu Thr Ala Lys Gly Tyr Asn Tyr Thr Ser Val Asp Ser Ser Tyr Ala
545                 550                 555                 560

Ser Thr Tyr Asn Asp Thr Asn Lys Thr Val Lys Met Thr Asn Ala Gly
                565                 570                 575

Gln Ser Val Thr Tyr Tyr Phe Thr Asp Val Lys Ala Pro Thr Val Thr
            580                 585                 590

Val Gly Asn Gln Thr Ile Glu Val Gly Lys Thr Met Asn Pro Ile Val
        595                 600                 605

Leu Thr Thr Thr Asp Asn Gly Thr Gly Thr Val Thr Asn Thr Val Thr
610                 615                 620

Gly Leu Pro Ser Gly Leu Ser Tyr Asp Ser Ala Thr Asn Ser Ile Ile
625                 630                 635                 640

Gly Thr Pro Thr Lys Ile Gly Gln Ser Thr Val Thr Val Ser Thr
                645                 650                 655

Asp Gln Ala Asn Asn Lys Ser Thr Thr Thr Phe Thr Ile Asn Val Val
            660                 665                 670

Asp Thr Thr Ala Pro Thr Val Thr Pro Ile Gly Asp Gln Ser Ser Glu
        675                 680                 685

Val Tyr Ser Pro Ile Ser Pro Ile Lys Ile Ala Thr Gln Asp Asn Ser
690                 695                 700

Gly Asn Ala Val Thr Asn Thr Val Thr Gly Leu Pro Ser Gly Leu Thr
705                 710                 715                 720

Phe Asp Ser Thr Asn Asn Thr Ile Ser Gly Thr Pro Thr Asn Ile Gly
                725                 730                 735

Thr Ser Thr Ile Ser Ile Val Ser Thr Asp Ala Ser Gly Asn Lys Thr
            740                 745                 750
```

-continued

Thr Thr Thr Phe Lys Tyr Glu Val Thr Arg Asn Ser Met Ser Asp Ser
    755                 760                 765

Val Ser Thr Ser Gly Ser Thr Gln Gln Ser Gln Ser Val Ser Thr Ser
770                 775                 780

Lys Ala Asp Ser Gln Ser Ala Ser Thr Ser Thr Ser Gly Ser Ile Val
785                 790                 795                 800

Val Ser Thr Ser Ala Ser Thr Ser Lys Ser Thr Ser Val Ser Leu Ser
                805                 810                 815

Asp Ser Val Ser Ala Ser Lys Ser Leu Ser Thr Ser Glu Ser Asn Ser
                820                 825                 830

Val Ser Ser Ser Thr Ser Thr Ser Leu Val Asn Ser Gln Ser Val Ser
                835                 840                 845

Ser Ser Met Ser Asp Ser Ala Ser Lys Ser Thr Ser Leu Ser Asp Ser
    850                 855                 860

Ile Ser Asn Ser Ser Ser Thr Glu Lys Ser Glu Ser Leu Ser Thr Ser
865                 870                 875                 880

Thr Ser Asp Ser Leu Arg Thr Ser Thr Ser Leu Ser Asp Ser Leu Ser
                885                 890                 895

Met Ser Thr Ser Gly Ser Leu Ser Lys Ser Gln Ser Leu Ser Thr Ser
                900                 905                 910

Ile Ser Gly Ser Ser Ser Thr Ser Ala Ser Leu Ser Asp Ser Thr Ser
                915                 920                 925

Asn Ala Ile Ser Thr Ser Thr Ser Leu Ser Glu Ser Ala Ser Thr Ser
930                 935                 940

Asp Ser Ile Ser Ile Ser Asn Ser Ile Ala Asn Ser Gln Ser Ala Ser
945                 950                 955                 960

Thr Ser Lys Ser Asp Ser Gln Ser Thr Ser Ile Ser Leu Ser Thr Ser
                965                 970                 975

Asp Ser Lys Ser Met Ser Thr Ser Glu Ser Leu Ser Asp Ser Thr Ser
                980                 985                 990

Thr Ser Gly Ser Val Ser Gly Ser Leu Ser Ile Ala Ala Ser Gln Ser
                995                 1000                1005

Val Ser Thr Ser Thr Ser Asp Ser Met Ser Thr Ser Glu Ile Val
    1010                1015                1020

Ser Asp Ser Ile Ser Thr Ser Gly Ser Leu Ser Ala Ser Asp Ser
    1025                1030                1035

Lys Ser Met Ser Val Ser Ser Met Ser Thr Ser Gln Ser Gly
    1040                1045                1050

Ser Thr Ser Glu Ser Leu Ser Asp Ser Gln Ser Thr Ser Asp Ser
    1055                1060                1065

Asp Ser Lys Ser Leu Ser Gln Ser Thr Ser Gln Ser Gly Ser Thr
    1070                1075                1080

Ser Thr Ser Thr Ser Thr Ser Ala Ser Val Arg Thr Ser Glu Ser
    1085                1090                1095

Gln Ser Thr Ser Gly Ser Met Ser Ala Ser Gln Ser Asp Ser Met
    1100                1105                1110

Ser Ile Ser Thr Ser Phe Ser Asp Ser Thr Ser Asp Ser Lys Ser
    1115                1120                1125

Ala Ser Thr Ala Ser Ser Glu Ser Ile Ser Gln Ser Ala Ser Thr
    1130                1135                1140

Ser Thr Ser Gly Ser Val Ser Thr Ser Thr Ser Leu Ser Thr Ser
    1145                1150                1155

Asn Ser Glu Arg Thr Ser Thr Ser Met Ser Asp Ser Thr Ser Leu
    1160                1165                1170

Ser Thr Ser Glu Ser Asp Ser Ile Ser Glu Ser Thr Ser Thr Ser
    1175                1180                1185

Asp Ser Ile Ser Glu Ala Ile Ser Ala Ser Glu Ser Thr Phe Ile
    1190                1195                1200

Ser Leu Ser Glu Ser Asn Ser Thr Ser Asp Ser Glu Ser Gln Ser
    1205                1210                1215

Ala Ser Ala Phe Leu Ser Glu Ser Leu Ser Glu Ser Thr Ser Glu
    1220                1225                1230

Ser Thr Ser Glu Ser Val Ser Ser Ser Thr Ser Glu Ser Thr Ser
    1235                1240                1245

Leu Ser Asp Ser Thr Ser Glu Ser Gly Ser Thr Ser Thr Ser Leu
    1250                1255                1260

Ser Asn Ser Thr Ser Gly Ser Thr Ser Ile Ser Thr Ser Thr Ser
    1265                1270                1275

Ile Ser Glu Ser Thr Ser Thr Phe Lys Ser Glu Ser Val Ser Thr
    1280                1285                1290

Ser Leu Ser Met Ser Thr Ser Thr Ser Leu Ser Asp Ser Thr Ser
    1295                1300                1305

Leu Ser Thr Ser Leu Ser Asp Ser Thr Ser Asp Ser Lys Ser Asp
    1310                1315                1320

Ser Leu Ser Thr Ser Met Ser Thr Ser Asp Ser Ile Ser Thr Ser
    1325                1330                1335

Lys Ser Asp Ser Ile Ser Thr Ser Thr Ser Leu Ser Gly Ser Thr
    1340                1345                1350

Ser Glu Ser Glu Ser Asp Ser Thr Ser Ser Ser Glu Ser Lys Ser
    1355                1360                1365

Asp Ser Thr Ser Met Ser Ile Ser Met Ser Gln Ser Thr Ser Gly
    1370                1375                1380

Ser Thr Ser Thr Ser Thr Ser Thr Ser Leu Ser Asp Ser Thr Ser
    1385                1390                1395

Thr Ser Leu Ser Leu Ser Ala Ser Met Asn Gln Ser Gly Val Asp
    1400                1405                1410

Ser Asn Ser Ala Ser Gln Ser Ala Ser Asn Ser Thr Ser Thr Ser
    1415                1420                1425

Thr Ser Glu Ser Asp Ser Gln Ser Thr Ser Ser Tyr Thr Ser Gln
    1430                1435                1440

Ser Thr Ser Gln Ser Glu Ser Thr Ser Thr Ser Thr Ser Leu Ser
    1445                1450                1455

Asp Ser Thr Ser Ile Ser Lys Ser Thr Ser Gln Ser Gly Ser Val
    1460                1465                1470

Ser Thr Ser Ala Ser Leu Ser Gly Ser Glu Ser Glu Ser Asp Ser
    1475                1480                1485

Gln Ser Ile Ser Thr Ser Ala Ser Glu Ser Thr Ser Glu Ser Ala
    1490                1495                1500

Ser Thr Ser Leu Ser Asp Ser Thr Ser Thr Ser Asn Ser Gly Ser
    1505                1510                1515

Ala Ser Thr Ser Thr Ser Leu Ser Asn Ser Ala Ser Ala Ser Glu
    1520                1525                1530

Ser Asp Leu Ser Ser Thr Ser Leu Ser Asp Ser Thr Ser Ala Ser
    1535                1540                1545

Met Gln Ser Ser Glu Ser Asp Ser Gln Ser Thr Ser Ala Ser Leu
    1550                1555                1560

Ser Asp Ser Leu Ser Thr Ser Thr Ser Asn Arg Met Ser Thr Ile

-continued

```
              1565                1570                1575

Ala  Ser  Leu  Ser  Thr  Ser  Val  Ser  Thr  Ser  Glu  Ser  Gly  Ser  Thr
     1580                1585                1590

Ser  Glu  Ser  Thr  Ser  Glu  Ser  Asp  Ser  Thr  Ser  Thr  Ser  Leu  Ser
     1595                1600                1605

Asp  Ser  Gln  Ser  Thr  Ser  Arg  Ser  Thr  Ser  Ala  Ser  Gly  Ser  Ala
     1610                1615                1620

Ser  Thr  Ser  Thr  Ser  Thr  Ser  Asp  Ser  Arg  Ser  Thr  Ser  Ala  Ser
     1625                1630                1635

Thr  Ser  Thr  Ser  Met  Arg  Thr  Ser  Thr  Ser  Asp  Ser  Gln  Ser  Met
     1640                1645                1650

Ser  Leu  Ser  Thr  Ser  Thr  Ser  Thr  Ser  Met  Ser  Asp  Ser  Thr  Ser
     1655                1660                1665

Leu  Ser  Asp  Ser  Val  Ser  Asp  Ser  Thr  Ser  Asp  Ser  Thr  Ser  Ala
     1670                1675                1680

Ser  Thr  Ser  Gly  Ser  Met  Ser  Val  Ser  Ile  Ser  Leu  Ser  Asp  Ser
     1685                1690                1695

Thr  Ser  Thr  Ser  Thr  Ser  Ala  Ser  Glu  Val  Met  Ser  Ala  Ser  Ile
     1700                1705                1710

Ser  Asp  Ser  Gln  Ser  Met  Ser  Glu  Ser  Val  Asn  Asp  Ser  Glu  Ser
     1715                1720                1725

Val  Ser  Glu  Ser  Asn  Ser  Glu  Ser  Asp  Ser  Lys  Ser  Met  Ser  Gly
     1730                1735                1740

Ser  Thr  Ser  Val  Ser  Asp  Ser  Gly  Ser  Leu  Ser  Val  Ser  Thr  Ser
     1745                1750                1755

Leu  Arg  Lys  Ser  Glu  Ser  Val  Ser  Glu  Ser  Ser  Ser  Leu  Ser  Cys
     1760                1765                1770

Ser  Gln  Ser  Met  Ser  Asp  Ser  Val  Ser  Thr  Ser  Asp  Ser  Ser  Ser
     1775                1780                1785

Leu  Ser  Val  Ser  Thr  Ser  Leu  Arg  Ser  Ser  Glu  Ser  Val  Ser  Glu
     1790                1795                1800

Ser  Asp  Ser  Leu  Ser  Asp  Ser  Lys  Ser  Thr  Ser  Gly  Ser  Thr  Ser
     1805                1810                1815

Thr  Ser  Thr  Ser  Gly  Ser  Leu  Ser  Thr  Ser  Thr  Ser  Leu  Ser  Gly
     1820                1825                1830

Ser  Glu  Ser  Val  Ser  Glu  Ser  Thr  Ser  Leu  Ser  Asp  Ser  Ile  Ser
     1835                1840                1845

Met  Ser  Asp  Ser  Thr  Ser  Thr  Ser  Asp  Ser  Asp  Ser  Leu  Ser  Gly
     1850                1855                1860

Ser  Ile  Ser  Leu  Ser  Gly  Ser  Thr  Ser  Leu  Ser  Thr  Ser  Asp  Ser
     1865                1870                1875

Leu  Ser  Asp  Ser  Lys  Ser  Leu  Ser  Ser  Ser  Gln  Ser  Met  Ser  Gly
     1880                1885                1890

Ser  Glu  Ser  Thr  Ser  Thr  Ser  Val  Ser  Asp  Ser  Gln  Ser  Ser  Ser
     1895                1900                1905

Thr  Ser  Asn  Ser  Gln  Phe  Asp  Ser  Met  Ser  Ile  Ser  Ala  Ser  Glu
     1910                1915                1920

Ser  Asp  Ser  Met  Ser  Thr  Ser  Asp  Ser  Ser  Ser  Ile  Ser  Gly  Ser
     1925                1930                1935

Asn  Ser  Thr  Ser  Thr  Ser  Leu  Ser  Thr  Ser  Asp  Ser  Met  Ser  Gly
     1940                1945                1950

Ser  Val  Ser  Val  Ser  Thr  Ser  Thr  Ser  Leu  Ser  Asp  Ser  Ile  Ser
     1955                1960                1965
```

| Gly | Ser | Thr | Ser | Val | Ser | Asp | Ser | Ser | Ser | Thr | Ser | Thr | Ser | Thr |
|---|---|---|---|---|---|---|---|---|---|---|---|---|---|---|
| | 1970 | | | | 1975 | | | | 1980 | | | | | |

| Ser | Leu | Ser | Asp | Ser | Met | Ser | Gln | Ser | Gln | Ser | Thr | Ser | Thr | Ser |
|---|---|---|---|---|---|---|---|---|---|---|---|---|---|---|
| 1985 | | | | | 1990 | | | | | 1995 | | | | |

| Ala | Ser | Gly | Ser | Leu | Ser | Thr | Ser | Ile | Ser | Thr | Ser | Met | Ser | Met |
|---|---|---|---|---|---|---|---|---|---|---|---|---|---|---|
| 2000 | | | | | 2005 | | | | | 2010 | | | | |

| Ser | Ala | Ser | Thr | Ser | Ser | Ser | Gln | Ser | Thr | Ser | Val | Ser | Thr | Ser |
|---|---|---|---|---|---|---|---|---|---|---|---|---|---|---|
| | 2015 | | | | 2020 | | | | | 2025 | | | | |

| Leu | Ser | Thr | Ser | Asp | Ser | Ile | Ser | Asp | Ser | Thr | Ser | Ile | Ser | Ile |
|---|---|---|---|---|---|---|---|---|---|---|---|---|---|---|
| | 2030 | | | | 2035 | | | | | 2040 | | | | |

| Ser | Gly | Ser | Gln | Ser | Thr | Val | Glu | Ser | Glu | Ser | Thr | Ser | Asp | Ser |
|---|---|---|---|---|---|---|---|---|---|---|---|---|---|---|
| | 2045 | | | | 2050 | | | | | 2055 | | | | |

| Thr | Ser | Ile | Ser | Asp | Ser | Glu | Ser | Leu | Ser | Thr | Ser | Asp | Ser | Asp |
|---|---|---|---|---|---|---|---|---|---|---|---|---|---|---|
| | 2060 | | | | 2065 | | | | | 2070 | | | | |

| Ser | Thr | Ser | Thr | Ser | Thr | Ser | Asp | Ser | Thr | Ser | Gly | Ser | Thr | Ser |
|---|---|---|---|---|---|---|---|---|---|---|---|---|---|---|
| | 2075 | | | | 2080 | | | | | 2085 | | | | |

| Thr | Ser | Ile | Ser | Glu | Ser | Leu | Ser | Thr | Ser | Gly | Ser | Gly | Ser | Thr |
|---|---|---|---|---|---|---|---|---|---|---|---|---|---|---|
| | 2090 | | | | 2095 | | | | | 2100 | | | | |

| Ser | Val | Ser | Asp | Ser | Thr | Ser | Met | Ser | Glu | Ser | Asn | Ser | Ser | Ser |
|---|---|---|---|---|---|---|---|---|---|---|---|---|---|---|
| | 2105 | | | | 2110 | | | | | 2115 | | | | |

| Val | Ser | Met | Ser | Gln | Asp | Lys | Ser | Asp | Ser | Thr | Ser | Ile | Ser | Asp |
|---|---|---|---|---|---|---|---|---|---|---|---|---|---|---|
| | 2120 | | | | 2125 | | | | | 2130 | | | | |

| Ser | Glu | Ser | Val | Ser | Thr | Ser | Thr | Ser | Thr | Ser | Leu | Ser | Thr | Ser |
|---|---|---|---|---|---|---|---|---|---|---|---|---|---|---|
| | 2135 | | | | 2140 | | | | | 2145 | | | | |

| Asp | Ser | Thr | Ser | Thr | Ser | Glu | Ser | Leu | Ser | Thr | Ser | Met | Ser | Gly |
|---|---|---|---|---|---|---|---|---|---|---|---|---|---|---|
| | 2150 | | | | 2155 | | | | | 2160 | | | | |

| Ser | Gln | Ser | Ile | Ser | Asp | Ser | Thr | Ser | Thr | Ser | Met | Ser | Gly | Ser |
|---|---|---|---|---|---|---|---|---|---|---|---|---|---|---|
| | 2165 | | | | 2170 | | | | | 2175 | | | | |

| Thr | Ser | Thr | Ser | Glu | Ser | Asn | Ser | Met | His | Pro | Ser | Asp | Ser | Met |
|---|---|---|---|---|---|---|---|---|---|---|---|---|---|---|
| | 2180 | | | | 2185 | | | | | 2190 | | | | |

| Ser | Met | His | His | Thr | His | Ser | Thr | Ser | Thr | Ser | Arg | Leu | Ser | Ser |
|---|---|---|---|---|---|---|---|---|---|---|---|---|---|---|
| | 2195 | | | | 2200 | | | | | 2205 | | | | |

| Glu | Ala | Thr | Thr | Ser | Thr | Ser | Glu | Ser | Gln | Ser | Thr | Leu | Ser | Ala |
|---|---|---|---|---|---|---|---|---|---|---|---|---|---|---|
| | 2210 | | | | 2215 | | | | | 2220 | | | | |

| Thr | Ser | Glu | Val | Thr | Lys | His | Asn | Gly | Thr | Pro | Ala | Gln | Ser | Glu |
|---|---|---|---|---|---|---|---|---|---|---|---|---|---|---|
| | 2225 | | | | 2230 | | | | | 2235 | | | | |

| Lys | Arg | Leu | Pro | Asp | Thr | Gly | Asp | Ser | Ile | Lys | Gln | Asn | Gly | Leu |
|---|---|---|---|---|---|---|---|---|---|---|---|---|---|---|
| | 2240 | | | | 2245 | | | | | 2250 | | | | |

| Leu | Gly | Gly | Val | Met | Thr | Leu | Leu | Val | Gly | Leu | Gly | Leu | Met | Lys |
|---|---|---|---|---|---|---|---|---|---|---|---|---|---|---|
| | 2255 | | | | 2260 | | | | | 2265 | | | | |

| Arg | Lys | Lys | Lys | Lys | Asp | Glu | Asn | Asp | Gln | Asp | Asp | Ser | Gln | Ala |
|---|---|---|---|---|---|---|---|---|---|---|---|---|---|---|
| | 2270 | | | | 2275 | | | | | 2280 | | | | |

<210> SEQ ID NO 5
<211> LENGTH: 2730
<212> TYPE: DNA
<213> ORGANISM: Staphylococcus epidermidis

<400> SEQUENCE: 5

| | |
|---|---|
| ttattatcaa ttaaatataa tcttatagga gttgttaaca acatgaacaa acatcaccca | 60 |
| aaattaaggt ctttctattc tattagaaaa tcaactctag gcgttgcatc ggtcattgtc | 120 |
| agtacactat ttttaattac ttctcaacat caagcacaag cagcagaaaa tacaaatact | 180 |
| tcagataaaa tctcggaaaa tcaaaataat aatgcaacta caactcagcc acctaaggat | 240 |
| acaaatcaaa cacaacctgc tacgcaacca gcaaacactg cgaaaaacta tcctgcagcg | 300 |

```
gatgaatcac ttaaagatgc aattaaagat cctgcattag aaaataaaga acatgatata    360
ggtccaagag aacaagtcaa tttccagtta ttagataaaa acaatgaaac gcagtactat    420
cactttttca gcatcaaaga tccagcagat gtgtattaca ctaaaaagaa agcagaagtt    480
gaattagaca tcaatactgc ttcaacatgg aagaagtttg aagtctatga aaacaatcaa    540
aaattgccag tgagacttgt atcatatagt cctgtaccag aagaccatgc ctatattcga    600
ttcccagttt cagatggcac acaagaattg aaaattgttt cttcgactca aattgatgat    660
ggagaagaaa caaattatga ttatactaaa ttagtatttg ctaaacctat ttataacgat    720
ccttcacttg taaaatcaga tacaaatgat gcagtagtaa cgaatgatca atcaagttca    780
gtcgcaagta atcaaacaaa cacgaataca tctaatcaaa atatatcaac gatcaacaat    840
gctaataatc aaccgcaggc aacgaccaat atgagtcaac ctgcacaacc aaaatcgtca    900
acgaatgcag atcaagcgtc aagccaacca gctcatgaaa caattctaa tggtaatact    960 aacgataaaa cgaatgagtc aagtaatcag tcggatgtta atcaacagta tccaccagca   1020
gatgaatcac tacaagatgc aattaaaaac ccggctatca tcgataaaga acatacagct   1080
gataattggc gaccaattga ttttcaaatg aaaaatgata aaggtgaaag acagttctat   1140
cattatgcta gtactgttga accagcaact gtcattttta caaaaacagg accaataatt   1200
gaattaggtt taaagacagc ttcaacatgg aagaaatttg aagtttatga aggtgacaaa   1260
aagttaccag tcgaattagt atcatatgat tctgataaag attatgccta tattcgtttc   1320
ccagtatcta atggtacgag agaagttaaa attgtgtcat ctattgaata tggtgagaac   1380
atccatgaag actatgatta tacgctaatg gtctttgcac agcctattac taataaccca   1440
gacgactatg tggatgaaga acatacaat ttacaaaaat tattagctcc gtatcacaaa   1500
gctaaaacgt tagaaagaca agtttatgaa ttagaaaaat tacaagagaa attgccagaa   1560
aaatataagg cggaatataa aaagaaatta gatcaaacta gagtagagtt agctgatcaa   1620
gttaaatcag cagtgacgga atttgaaaat gttacaccta caaatgatca attaacagat   1680
ttacaagaag cgcatttgt tgtttttgaa agtgaagaaa atagtgagtc agttatggac   1740
ggctttgttg aacatccatt ctatacagca actttaaatg gtcaaaaata tgtagtgatg   1800
aaaacaaagg atgacagtta ctggaaagat ttaattgtag aaggtaaacg tgtcactact   1860
gtttctaaag atcctaaaaa taattctaga acgctgattt tcccatatat acctgacaaa   1920
gcagtttaca atgcgattgt taaagtcgtt gtggcaaaca ttggttatga aggtcaatat   1980
catgtcagaa ttataaatca ggatatcaat acaaaagatg atgatacatc acaaaataac   2040
acgagtgaac cgctaaatgt acaaacagga caagaaggta aggttgctga tacagatgta   2100
gctgaaaata gcagcactgc aacaaatcct aaagatgcgt ctgataaagc agatgtgata   2160
gaaccagagt ctgacgtggt taaagatgct gataataata ttgataaaga tgtgcaacat   2220
gatgttgatc atttatccga tatgtcggat aataatcact cgataaaata tgatttaaaa   2280
gaaatggata ctcaaattgc caaagatact gatagaaatg tggataaaga tgccgataat   2340
agcgttggta tgtcatctaa tgtcgatact gataaagact ctaataaaaa taaagacaaa   2400
gtcatacagc tgaatcatat tgccgataaa aataatcata ctggaaaagc agcaaagctt   2460
gacgtagtga aacaaaatta taataataca gacaaagtta ctgacaaaaa aacaactgaa   2520
catctgccga gtgatattca taaaactgta gataaaacag tgaaaacaaa agaaaaagcc   2580
ggcacaccat cgaagaaaa caaacttagt caatctaaaa tgctaccaaa aactggaaaa   2640
acaacttcaa gccaatcatg gtggggctta tatgcgttat taggtatgtt agctttattc   2700
```
attcctaaat tcagaaaaga atctaaataa                                           2730

<210> SEQ ID NO 6
<211> LENGTH: 909
<212> TYPE: PRT
<213> ORGANISM: Staphylococcus epidermidis

<400> SEQUENCE: 6

Leu Leu Ser Ile Lys Tyr Asn Leu Ile Gly Val Val Asn Asn Met Asn
1               5                   10                  15

Lys His His Pro Lys Leu Arg Ser Phe Tyr Ser Ile Arg Lys Ser Thr
            20                  25                  30

Leu Gly Val Ala Ser Val Ile Val Ser Thr Leu Phe Leu Ile Thr Ser
        35                  40                  45

Gln His Gln Ala Gln Ala Ala Glu Asn Thr Asn Thr Ser Asp Lys Ile
    50                  55                  60

Ser Glu Asn Gln Asn Asn Asn Ala Thr Thr Thr Gln Pro Pro Lys Asp
65                  70                  75                  80

Thr Asn Gln Thr Gln Pro Ala Thr Gln Pro Ala Asn Thr Ala Lys Asn
                85                  90                  95

Tyr Pro Ala Ala Asp Glu Ser Leu Lys Asp Ala Ile Lys Asp Pro Ala
            100                 105                 110

Leu Glu Asn Lys Glu His Asp Ile Gly Pro Arg Glu Gln Val Asn Phe
        115                 120                 125

Gln Leu Leu Asp Lys Asn Asn Glu Thr Gln Tyr Tyr His Phe Phe Ser
    130                 135                 140

Ile Lys Asp Pro Ala Asp Val Tyr Tyr Thr Lys Lys Lys Ala Glu Val
145                 150                 155                 160

Glu Leu Asp Ile Asn Thr Ala Ser Thr Trp Lys Lys Phe Glu Val Tyr
                165                 170                 175

Glu Asn Asn Gln Lys Leu Pro Val Arg Leu Val Ser Tyr Ser Pro Val
            180                 185                 190

Pro Glu Asp His Ala Tyr Ile Arg Phe Pro Val Ser Asp Gly Thr Gln
        195                 200                 205

Glu Leu Lys Ile Val Ser Ser Thr Gln Ile Asp Asp Gly Glu Glu Thr
    210                 215                 220

Asn Tyr Asp Tyr Thr Lys Leu Val Phe Ala Lys Pro Ile Tyr Asn Asp
225                 230                 235                 240

Pro Ser Leu Val Lys Ser Asp Thr Asn Asp Ala Val Val Thr Asn Asp
                245                 250                 255

Gln Ser Ser Ser Val Ala Ser Asn Gln Thr Asn Thr Asn Thr Ser Asn
            260                 265                 270

Gln Asn Ile Ser Thr Ile Asn Asn Ala Asn Asn Gln Pro Gln Ala Thr
        275                 280                 285

Thr Asn Met Ser Gln Pro Ala Gln Pro Lys Ser Thr Asn Ala Asp
    290                 295                 300

Gln Ala Ser Ser Gln Pro Ala His Glu Thr Asn Ser Asn Gly Asn Thr
305                 310                 315                 320

Asn Asp Lys Thr Asn Glu Ser Ser Asn Gln Ser Asp Val Asn Gln Gln
                325                 330                 335

Tyr Pro Pro Ala Asp Glu Ser Leu Gln Asp Ala Ile Lys Asn Pro Ala
            340                 345                 350

Ile Ile Asp Lys Glu His Thr Ala Asp Asn Trp Arg Pro Ile Asp Phe
        355                 360                 365

```
Gln Met Lys Asn Asp Lys Gly Glu Arg Gln Phe Tyr His Tyr Ala Ser
        370                 375                 380

Thr Val Glu Pro Ala Thr Val Ile Phe Thr Lys Thr Gly Pro Ile Ile
385                 390                 395                 400

Glu Leu Gly Leu Lys Thr Ala Ser Thr Trp Lys Lys Phe Glu Val Tyr
                    405                 410                 415

Glu Gly Asp Lys Lys Leu Pro Val Glu Leu Val Ser Tyr Asp Ser Asp
                420                 425                 430

Lys Asp Tyr Ala Tyr Ile Arg Phe Pro Val Ser Asn Gly Thr Arg Glu
            435                 440                 445

Val Lys Ile Val Ser Ser Ile Glu Tyr Gly Asn Ile His Glu Asp
450                 455                 460

Tyr Asp Tyr Thr Leu Met Val Phe Ala Gln Pro Ile Thr Asn Asn Pro
465                 470                 475                 480

Asp Asp Tyr Val Asp Glu Thr Tyr Asn Leu Gln Lys Leu Leu Ala
            485                 490                 495

Pro Tyr His Lys Ala Lys Thr Leu Glu Arg Gln Val Tyr Glu Leu Glu
            500                 505                 510

Lys Leu Gln Glu Lys Leu Pro Glu Lys Tyr Lys Ala Gly Tyr Lys Lys
        515                 520                 525

Lys Leu Asp Gln Thr Arg Val Glu Leu Ala Asp Gln Val Lys Ser Ala
        530                 535                 540

Val Thr Glu Phe Glu Asn Val Thr Pro Thr Asn Asp Gln Leu Thr Asp
545                 550                 555                 560

Leu Gln Glu Ala His Phe Val Val Phe Glu Ser Glu Asn Ser Glu
                565                 570                 575

Ser Val Met Asp Gly Phe Val Glu His Pro Phe Tyr Thr Ala Thr Leu
                580                 585                 590

Asn Gly Gln Lys Tyr Val Val Met Lys Thr Lys Asp Asp Ser Tyr Trp
        595                 600                 605

Lys Asp Leu Ile Val Glu Gly Lys Arg Val Thr Thr Val Ser Lys Asp
        610                 615                 620

Pro Lys Asn Asn Ser Arg Thr Leu Ile Phe Pro Tyr Ile Pro Asp Lys
625                 630                 635                 640

Ala Val Tyr Asn Ala Ile Val Lys Val Val Ala Asn Ile Gly Tyr
                645                 650                 655

Glu Gly Gln Tyr His Val Arg Ile Ile Asn Gln Asp Ile Asn Thr Lys
                660                 665                 670

Asp Asp Asp Thr Ser Gln Asn Asn Thr Ser Glu Pro Leu Asn Val Gln
            675                 680                 685

Thr Gly Gln Glu Gly Lys Val Ala Asp Thr Asp Val Ala Glu Asn Ser
        690                 695                 700

Ser Thr Ala Thr Asn Pro Lys Asp Ala Ser Lys Ala Asp Val Ile
705                 710                 715                 720

Glu Pro Glu Ser Asp Val Val Lys Asp Ala Asp Asn Ile Asp Lys
                725                 730                 735

Asp Val Gln His Asp Val Asp His Leu Ser Asp Met Ser Asp Asn Asn
            740                 745                 750

His Phe Asp Lys Tyr Asp Leu Lys Glu Met Asp Thr Gln Ile Ala Lys
        755                 760                 765

Asp Thr Asp Arg Asn Val Asp Lys Asp Ala Asp Asn Ser Val Gly Met
        770                 775                 780

Ser Ser Asn Val Asp Thr Asp Lys Asp Ser Asn Lys Asn Lys Asp Lys
785                 790                 795                 800
```

```
Val Ile Gln Leu Asn His Ile Ala Asp Lys Asn Asn His Thr Gly Lys
            805                 810                 815

Ala Ala Lys Leu Asp Val Val Lys Gln Asn Tyr Asn Asn Thr Asp Lys
        820                 825                 830

Val Thr Asp Lys Lys Thr Thr Glu His Leu Pro Ser Asp Ile His Lys
    835                 840                 845

Thr Val Asp Lys Thr Val Lys Thr Lys Glu Lys Ala Gly Thr Pro Ser
850                 855                 860

Lys Glu Asn Lys Leu Ser Gln Ser Lys Met Leu Pro Lys Thr Gly Glu
865                 870                 875                 880

Thr Thr Ser Ser Gln Ser Trp Trp Gly Leu Tyr Ala Leu Leu Gly Met
                885                 890                 895

Leu Ala Leu Phe Ile Pro Lys Phe Arg Lys Glu Ser Lys
            900                 905

<210> SEQ ID NO 7
<211> LENGTH: 1065
<212> TYPE: DNA
<213> ORGANISM: Staphylococcus epidermidis

<400> SEQUENCE: 7
gaggaaaaca acatgacaaa acattatttta aacagtaagt atcaatcaga acaacgttca        60
tcagctatga aaagattac aatgggtaca gcatctatca ttttaggttc ccttgtatac        120
ataggcgcag acagccaaca agtcaatgcg gcaacagaag ctacgaacgc aactaataat       180
caaagcacac aagtttctca agcaacatca caaccaatta atttccaagt gcaaaaagat       240
ggctcttcag agaagtcaca catggatgac tatatgcaac ccctggtaa agtaattaaa       300 caaaataata atattatttt ccaaaccgtg ttaaacaatg catcattctg gaaagaatac       360 aaatttaca atgcaaacaa tcaagaatta gcaacaactg ttgttaacga taataaaaaa       420
gcggatacta gaacaatcaa tgttgcagtt gaacctggat ataagagctt aactactaaa       480
gtacatattg tcgtgccaca aattaattac aatcatagat atactacgca tttggaattt       540
gaaaaagcaa ttcctacatt agctgacgca gcaaaaccaa acaatgttaa accggttcaa       600
ccaaaaccag ctcaacctaa acacctact gagcaaacta aaccagttca acctaaagtt       660
gaaaaagtta aacctactgt aactacaaca agcaaagttg aagacaatca ctctactaaa       720
gttgtaagta ctgacacaac aaaagatcaa actaaaacac aaactgctca tacagttaaa       780
acagcacaaa ctgctcaaga acaaaataaa gttcaaacac tgttaaagga tgttgcaaca       840
gcgaaatctg aaagcaacaa tcaagctgta agtgataata atcacaacaa aactaacaaa       900
gttacaaaac ataacgaaac gcctaaacaa gcatctaaag ctaagaatt accaaaaact       960 ggtttaactt cagttgataa ctttattagc acagttgcct tcgcaacact tgcccttta      1020 ggttcattat ctttattact tttcaaaaga aagaatcta aataa                         1065

<210> SEQ ID NO 8
<211> LENGTH: 354
<212> TYPE: PRT
<213> ORGANISM: Staphylococcus epidermidis

<400> SEQUENCE: 8

Glu Glu Asn Asn Met Thr Lys His Tyr Leu Asn Ser Lys Tyr Gln Ser
1               5                   10                  15

Glu Gln Arg Ser Ser Ala Met Lys Lys Ile Thr Met Gly Thr Ala Ser
            20                  25                  30
```

```
Ile Ile Leu Gly Ser Leu Val Tyr Ile Gly Ala Asp Ser Gln Gln Val
        35                  40                  45

Asn Ala Ala Thr Glu Ala Thr Asn Ala Thr Asn Asn Gln Ser Thr Gln
 50                  55                  60

Val Ser Gln Ala Thr Ser Gln Pro Ile Asn Phe Gln Val Gln Lys Asp
 65                  70                  75                  80

Gly Ser Ser Glu Lys Ser His Met Asp Asp Tyr Met Gln His Pro Gly
                 85                  90                  95

Lys Val Ile Lys Gln Asn Asn Lys Tyr Tyr Phe Gln Thr Val Leu Asn
                100                 105                 110

Asn Ala Ser Phe Trp Lys Glu Tyr Lys Phe Tyr Asn Ala Asn Asn Gln
            115                 120                 125

Glu Leu Ala Thr Thr Val Val Asn Asp Asn Lys Ala Asp Thr Arg
130                 135                 140

Thr Ile Asn Val Ala Val Glu Pro Gly Tyr Lys Ser Leu Thr Thr Lys
145                 150                 155                 160

Val His Ile Val Val Pro Gln Ile Asn Tyr Asn His Arg Tyr Thr Thr
                165                 170                 175

His Leu Glu Phe Glu Lys Ala Ile Pro Thr Leu Ala Asp Ala Ala Lys
            180                 185                 190

Pro Asn Asn Val Lys Pro Val Gln Pro Lys Pro Ala Gln Pro Lys Thr
            195                 200                 205

Pro Thr Glu Gln Thr Lys Pro Val Gln Pro Lys Val Glu Lys Val Lys
210                 215                 220

Pro Thr Val Thr Thr Thr Ser Lys Val Glu Asp Asn His Ser Thr Lys
225                 230                 235                 240

Val Val Ser Thr Asp Thr Thr Lys Asp Gln Thr Lys Thr Gln Thr Ala
                245                 250                 255

His Thr Val Lys Thr Ala Gln Thr Ala Gln Glu Gln Asn Lys Val Gln
            260                 265                 270

Thr Pro Val Lys Asp Val Ala Thr Ala Lys Ser Glu Ser Asn Asn Gln
            275                 280                 285

Ala Val Ser Asp Asn Lys Ser Gln Gln Thr Asn Lys Val Thr Lys His
290                 295                 300

Asn Glu Thr Pro Lys Gln Ala Ser Lys Ala Lys Glu Leu Pro Lys Thr
305                 310                 315                 320

Gly Leu Thr Ser Val Asp Asn Phe Ile Ser Thr Val Ala Phe Ala Thr
                325                 330                 335

Leu Ala Leu Leu Gly Ser Leu Ser Leu Leu Phe Lys Arg Lys Glu
            340                 345                 350

Ser Lys

<210> SEQ ID NO 9
<211> LENGTH: 1965
<212> TYPE: DNA
<213> ORGANISM: Staphylococcus epidermidis

<400> SEQUENCE: 9
tatacaatta ggagttgttt ctacaacatg aacaaacagc aaaaagaatt taaatcattt      60
tattcaatta gaaagtcatc actaggcgtt gcatctgtag caattagtac acttttatta    120
ttaatgtcaa atggcgaagc acaagcagca gctgaagaaa caggtggtac aaatacagaa    180
gcacaaccaa aaactgaagc agttgcaagt ccaacaacaa catctgaaaa agctccagaa    240
actaaaccag tagctaatgc tgtctcagta tctaataaag aagttgaggc ccctacttct    300
```

```
gaaacaaaag aagctaaaga agttaaagaa gttaaagccc ctaaggaaac aaaagaagtt      360
aaaccagcag caaaagccac taacaataca tatcctattt tgaatcagga acttagagaa      420
gcgattaaaa accctgcaat aaaagacaaa gatcatagcg caccaaactc tcgtccaatt      480
gattttgaaa tgaaaagaa agatggaact caacagtttt atcattatgc aagttctgtt       540
aaacctgcta gagttatttt cactgattca aaaccagaaa ttgaattagg attacaatca      600
ggtcaatttt ggagaaaatt tgaagtttat gaaggtgaca aaaagttgcc aattaaatta      660
gtatcatacg atactgttaa agattatgct tacattcgct tctctgtatc aaacggaaca      720
aaagctgtta aaattgttag ttcaacacac ttcaataaca aagaagaaaa atacgattac      780
acattaatgg aattcgcaca accaatttat aacagtgcag ataaattcaa aactgaagaa      840
gattataaag ctgaaaaatt attagcgcca tataaaaaag cgaaaacact agaaagacaa      900
gtttatgaat taaataaaat tcaagataaa cttcctgaaa aattaaaggc tgagtacaag      960
aagaaattag aggatacaaa gaaagcttta gatgagcaag tgaaatcagc tattactgaa     1020
ttccaaaatg tacaaccaac aaatgaaaaa atgactgatt acaagatac aaaatatgtt      1080 gtttatgaaa gtgttgagaa taacgaatct atgatggata cttttgttaa acaccctatt     1140
aaaacaggta tgcttaacgg caaaaaatat atggtcatgg aaactactaa tgacgattac     1200
tggaaagatt tcatggttga aggtcaacgt gttagaacta taagcaaaga tgctaaaaat     1260
aatactagaa caattatttt cccatatgtt gaaggtaaaa ctctatatga tgctatcgtt     1320
aaagttcacg taaaaacgat tgattatgat ggacaatacc atgtcagaat cgttgataaa     1380
gaagcattta caaaagccaa taccgataaa tctaacaaaa aagaacaaca agataactca     1440
gctaagaagg aagctactcc agctacgcct agcaaaccaa caccatcacc tgttgaaaaa     1500
gaatcacaaa aacaagacag ccaaaaagat gacaataaac aattaccaag tgttgaaaaa     1560
gaaaatgacg catctagtga gtcaggtaaa gacaaaacgc ctgctacaaa accaactaaa     1620
ggtgaagtag aatcaagtag tacaactcca actaaggtag tatctacgac tcaaaatgtt     1680
gcaaaaccaa caactgcttc atcaaaaaca acaaagatg ttgttcaaac ttcagcaggt      1740
tctagcgaag caaaagatag tgctccatta caaaagcaa acattaaaaa cacaaatgat      1800
ggacacactc aaagccaaaa caataaaaat acacaagaaa ataaagcaaa atcattacca     1860
caaactggtg aagaatcaaa taaagatatg acattaccat taatggcatt attagcttta     1920
agtagcatcg ttgcattcgt attacctaga aaacgtaaaa actaa                     1965
```

<210> SEQ ID NO 10
<211> LENGTH: 654
<212> TYPE: PRT
<213> ORGANISM: Staphylococcus epidermidis

<400> SEQUENCE: 10

```
Tyr Thr Ile Arg Ser Cys Phe Tyr Asn Met Asn Lys Gln Gln Lys Glu
  1               5                  10                  15

Phe Lys Ser Phe Tyr Ser Ile Arg Lys Ser Ser Leu Gly Val Ala Ser
             20                  25                  30

Val Ala Ile Ser Thr Leu Leu Leu Met Ser Asn Gly Glu Ala Gln
         35                  40                  45

Ala Ala Ala Glu Glu Thr Gly Gly Thr Asn Thr Glu Ala Gln Pro Lys
     50                  55                  60

Thr Glu Ala Val Ala Ser Pro Thr Thr Ser Glu Lys Ala Pro Glu
 65                  70                  75                  80

Thr Lys Pro Val Ala Asn Ala Val Ser Val Ser Asn Lys Glu Val Glu
```

```
                    85                  90                  95
Ala Pro Thr Ser Glu Thr Lys Glu Ala Lys Glu Val Lys Glu Val Lys
                100                 105                 110

Ala Pro Lys Glu Thr Lys Glu Val Lys Pro Ala Ala Lys Ala Thr Asn
                115                 120                 125

Asn Thr Tyr Pro Ile Leu Asn Gln Glu Leu Arg Glu Ala Ile Lys Asn
                130                 135                 140

Pro Ala Ile Lys Asp Lys Asp His Ser Ala Pro Asn Ser Arg Pro Ile
145                 150                 155                 160

Asp Phe Glu Met Lys Lys Lys Asp Gly Thr Gln Gln Phe Tyr His Tyr
                165                 170                 175

Ala Ser Ser Val Lys Pro Ala Arg Val Ile Phe Thr Asp Ser Lys Pro
                180                 185                 190

Glu Ile Glu Leu Gly Leu Gln Ser Gly Gln Phe Trp Arg Lys Phe Glu
                195                 200                 205

Val Tyr Glu Gly Asp Lys Lys Leu Pro Ile Lys Leu Val Ser Tyr Asp
                210                 215                 220

Thr Val Lys Asp Tyr Ala Tyr Ile Arg Phe Ser Val Ser Asn Gly Thr
225                 230                 235                 240

Lys Ala Val Lys Ile Val Ser Ser Thr His Phe Asn Asn Lys Glu Glu
                245                 250                 255

Lys Tyr Asp Tyr Thr Leu Met Glu Phe Ala Gln Pro Ile Tyr Asn Ser
                260                 265                 270

Ala Asp Lys Phe Lys Thr Glu Glu Asp Tyr Lys Ala Glu Lys Leu Leu
                275                 280                 285

Ala Pro Tyr Lys Lys Ala Lys Thr Leu Glu Arg Gln Val Tyr Glu Leu
                290                 295                 300

Asn Lys Ile Gln Asp Lys Leu Pro Glu Lys Leu Lys Ala Glu Tyr Lys
305                 310                 315                 320

Lys Lys Leu Glu Asp Thr Lys Lys Ala Leu Asp Glu Gln Val Lys Ser
                325                 330                 335

Ala Ile Thr Glu Phe Gln Asn Val Gln Pro Thr Asn Glu Lys Met Thr
                340                 345                 350

Asp Leu Gln Asp Thr Lys Tyr Val Val Tyr Glu Ser Val Glu Asn Asn
                355                 360                 365

Glu Ser Met Met Asp Thr Phe Val Lys His Pro Ile Lys Thr Gly Met
                370                 375                 380

Leu Asn Gly Lys Lys Tyr Met Val Met Glu Thr Thr Asn Asp Asp Tyr
385                 390                 395                 400

Trp Lys Asp Phe Met Val Glu Gly Gln Arg Val Arg Thr Ile Ser Lys
                405                 410                 415

Asp Ala Lys Asn Asn Thr Arg Thr Ile Ile Phe Pro Tyr Val Glu Gly
                420                 425                 430

Lys Thr Leu Tyr Asp Ala Ile Val Lys Val His Val Lys Thr Ile Asp
                435                 440                 445

Tyr Asp Gly Gln Tyr His Val Arg Ile Val Asp Lys Glu Ala Phe Thr
450                 455                 460

Lys Ala Asn Thr Asp Lys Ser Asn Lys Lys Glu Gln Gln Asp Asn Ser
465                 470                 475                 480

Ala Lys Lys Glu Ala Thr Pro Ala Thr Pro Ser Lys Pro Thr Pro Ser
                485                 490                 495

Pro Val Glu Lys Glu Ser Gln Lys Gln Asp Ser Gln Lys Asp Asp Asn
                500                 505                 510
```

```
Lys Gln Leu Pro Ser Val Glu Lys Glu Asn Asp Ala Ser Ser Glu Ser
            515                 520                 525

Gly Lys Asp Lys Thr Pro Ala Thr Lys Pro Thr Lys Gly Glu Val Glu
            530                 535                 540

Ser Ser Ser Thr Thr Pro Thr Lys Val Val Ser Thr Thr Gln Asn Val
545                 550                 555                 560

Ala Lys Pro Thr Thr Ala Ser Ser Lys Thr Thr Lys Asp Val Val Gln
                565                 570                 575

Thr Ser Ala Gly Ser Ser Glu Ala Lys Asp Ser Ala Pro Leu Gln Lys
            580                 585                 590

Ala Asn Ile Lys Asn Thr Asn Asp Gly His Thr Gln Ser Gln Asn Asn
            595                 600                 605

Lys Asn Thr Gln Glu Asn Lys Ala Lys Ser Leu Pro Gln Thr Gly Glu
            610                 615                 620

Glu Ser Asn Lys Asp Met Thr Leu Pro Leu Met Ala Leu Leu Ala Leu
625                 630                 635                 640

Ser Ser Ile Val Ala Phe Val Leu Pro Arg Lys Arg Lys Asn
                645                 650

<210> SEQ ID NO 11
<211> LENGTH: 2406
<212> TYPE: DNA
<213> ORGANISM: Staphylococcus epidermidis

<400> SEQUENCE: 11
tttataaata atttacataa aatcaatcat tttaatataa ggattatgat aatatattgg      60
tgtatgacag ttaatggagg gaacgaaatg aaagctttat acttaaaaac aagtgtatgg     120
ctcgttttgc tttttagtgt aatgggatta tggcaagtct cgaacgcggc tgagcagcat     180
acaccaatga aagcacatgc agtaacaacg atagacaaag caacaacaga taagcaacaa     240
gtaccgccaa caaggaagc ggctcatcat tctggcaaag aagcggcaac caacgtatca     300
gcatcagcgc agggaacagc tgatgataca aacagcaaag taacatccaa cgcaccatct     360
aacaaaccat ctacagtagt ttcaacaaaa gtaaacgaaa cacgcgacgt agatacacaa     420
caagcctcaa cacaaaaacc aactcacaca gcaacgttca aattatcaaa tgctaaaaca     480
gcatcacttt caccacgaat gtttgctgct aatgcaccac aaacaacaac acataaaata     540
ttacatacaa atgatatcca tggccgacta gccgaagaaa aagggcgtgt catcggtatg     600
gctaaattaa aaacagtaaa agaacaagaa aagcctgatt taatgttaga cgcaggagac     660
gccttccaag gtttaccact ttcaaaccag tctaaaggtg aagaaatggc taaagcaatg     720
aatgcagtag ttatgatgc tatggcagtc ggtaaccatg aatttgactt tggatacgat     780
cagttgaaaa agttagaggg tatgttagac ttcccgatgc taagtactaa cgtttataaa     840
gatggaaaac gcgcgtttaa gccttcaacg attgtaacaa aaaatggtat tcgttatgga     900
attattggtg taacgacacc agaaacaaag acgaaaacaa gacctgaagg cattaaaggc     960
gttgaattta gagatccatt acaaagtgtg acagcggaaa tgatgcgtat ttataaagac    1020
gtagatacat tgttgttat atcacattta ggaattgatc cttcaacaca agaaacatgg    1080
cgtggtgatt acttagtgaa acaattaagt caaatccac aattgaagaa acgtattaca    1140
gttattgatg gtcattcaca tacagtactt caaaatggtc aaatttataa caatgatgca    1200
ttggcacaaa caggtacagc acttgcgaat atcggtaaga ttacatttaa ttatcgcaat    1260
ggagaggtat cgaatattaa accgtcattg attaatgtta aagacgttga aaatgtaaca    1320
ccgaacaaag cattagctga acaaattaat caagctgatc aaacatttag agcacaaact    1380
```

```
gcagaggtaa ttattccaaa caataccatt gatttcaaag gagaaagaga tgacgttaga   1440
acgcgtgaaa caaatttagg aaacgcgatt gcagatgcta tggaagcgta tggcgttaag   1500
aatttctcta aaaagactga ctttgccgtg acaaatggtg gaggtattcg tgcctctatc   1560
gcaaaaggta aggtgacacg ctatgattta atctcagtat taccatttgg aaatacgatt   1620
gcgcaaattg atgtaaaagg ttcagacgtc tggacggctt tcgaacatag tttaggcgca   1680
ccaacaacac aaaaggacgg taagacagtg ttaacagcga atggcggttt actacatatc   1740
tctgattcaa tccgtgttta ctatgatata aataaaccgt ctggcaaacg aattaatgct   1800
attcaaattt taaataaaga gacaggtaag tttgaaaata ttgatttaaa acgtgtatat   1860
cacgtaacga tgaatgactt cacagcatca ggtggcgacg gatatagtat gttcggtggt   1920
cctagagaag aaggtatttc attagatcaa gtactagcaa gttatttaaa aacagctaac   1980
ttagctaagt atgatacgac agaaccacaa cgtatgttat taggtaaacc agcagtaagt   2040
gaacaaccag ctaaaggaca acaaggtagc aaaggtagta agtctggtaa agatacacaa   2100
ccaattggtg acgacaaagt gatggatcca gcgaaaaaac cagctccagg taaagttgta   2160
ttgttgctag cgcatagagg aactgttagt agcggtacaa aaggttctgg tcgcacaata   2220
gaaggagcta ctgtatcaag caagagtggg aaacaattgg ctagaatgtc agtgcctaaa   2280
ggtagcgcgc atgagaaaca gttaccaaaa actggaacta atcaaagttc aagcccagaa   2340
gcgatgtttg tattattagc aggtataggt ttaatcgcga ctgtacgacg tagaaaagct   2400
agctaa                                                             2406

<210> SEQ ID NO 12
<211> LENGTH: 801
<212> TYPE: PRT
<213> ORGANISM: Staphylococcus epidermidis

<400> SEQUENCE: 12

Phe Ile Asn Asn Leu His Lys Ile Asn His Phe Asn Ile Arg Ile Met
1               5                   10                  15

Ile Ile Tyr Trp Cys Met Thr Val Asn Gly Gly Asn Glu Met Lys Ala
            20                  25                  30

Leu Leu Leu Lys Thr Ser Val Trp Leu Val Leu Phe Ser Val Met
        35                  40                  45

Gly Leu Trp Gln Val Ser Asn Ala Ala Glu Gln His Thr Pro Met Lys
    50                  55                  60

Ala His Ala Val Thr Thr Ile Asp Lys Ala Thr Thr Asp Lys Gln Gln
65                  70                  75                  80

Val Pro Pro Thr Lys Glu Ala Ala His His Ser Gly Lys Glu Ala Ala
                85                  90                  95

Thr Asn Val Ser Ala Ser Ala Gln Gly Thr Ala Asp Asp Thr Asn Ser
            100                 105                 110

Lys Val Thr Ser Asn Ala Pro Ser Asn Lys Pro Ser Thr Val Val Ser
        115                 120                 125

Thr Lys Val Asn Glu Thr Arg Asp Val Asp Thr Gln Gln Ala Ser Thr
    130                 135                 140

Gln Lys Pro Thr His Thr Ala Thr Phe Lys Leu Ser Asn Ala Lys Thr
145                 150                 155                 160

Ala Ser Leu Ser Pro Arg Met Phe Ala Ala Asn Ala Pro Gln Thr Thr
                165                 170                 175

Thr His Lys Ile Leu His Thr Asn Asp Ile His Gly Arg Leu Ala Glu
            180                 185                 190
```

```
Glu Lys Gly Arg Val Ile Gly Met Ala Lys Leu Lys Thr Val Lys Glu
            195                 200                 205
Gln Glu Lys Pro Asp Leu Met Leu Asp Ala Gly Asp Ala Phe Gln Gly
        210                 215                 220
Leu Pro Leu Ser Asn Gln Ser Lys Gly Glu Met Ala Lys Ala Met
225                 230                 235                 240
Asn Ala Val Gly Tyr Asp Ala Met Ala Val Gly Asn His Glu Phe Asp
                245                 250                 255
Phe Gly Tyr Asp Gln Leu Lys Lys Leu Glu Gly Met Leu Asp Phe Pro
            260                 265                 270
Met Leu Ser Thr Asn Val Tyr Lys Asp Gly Lys Arg Ala Phe Lys Pro
        275                 280                 285
Ser Thr Ile Val Thr Lys Asn Gly Ile Arg Tyr Gly Ile Ile Gly Val
    290                 295                 300
Thr Thr Pro Glu Thr Lys Thr Lys Thr Arg Pro Glu Gly Ile Lys Gly
305                 310                 315                 320
Val Glu Phe Arg Asp Pro Leu Gln Ser Val Thr Ala Glu Met Met Arg
                325                 330                 335
Ile Tyr Lys Asp Val Asp Thr Phe Val Val Ser His Leu Gly Ile
            340                 345                 350
Asp Pro Ser Thr Gln Glu Thr Trp Arg Gly Asp Tyr Leu Val Lys Gln
        355                 360                 365
Leu Ser Gln Asn Pro Gln Leu Lys Lys Arg Ile Thr Val Ile Asp Gly
    370                 375                 380
His Ser His Thr Val Leu Gln Asn Gly Gln Ile Tyr Asn Asn Asp Ala
385                 390                 395                 400
Leu Ala Gln Thr Gly Thr Ala Leu Ala Asn Ile Gly Lys Ile Thr Phe
                405                 410                 415
Asn Tyr Arg Asn Gly Glu Val Ser Asn Ile Lys Pro Ser Leu Ile Asn
            420                 425                 430
Val Lys Asp Val Glu Asn Val Thr Pro Asn Lys Ala Leu Ala Glu Gln
        435                 440                 445
Ile Asn Gln Ala Asp Gln Thr Phe Arg Ala Gln Thr Ala Glu Val Ile
    450                 455                 460
Ile Pro Asn Asn Thr Ile Asp Phe Lys Gly Glu Arg Asp Asp Val Arg
465                 470                 475                 480
Thr Arg Glu Thr Asn Leu Gly Asn Ala Ile Ala Asp Ala Met Glu Ala
                485                 490                 495
Tyr Gly Val Lys Asn Phe Ser Lys Lys Thr Asp Phe Ala Val Thr Asn
            500                 505                 510
Gly Gly Gly Ile Arg Ala Ser Ile Ala Lys Gly Lys Val Thr Arg Tyr
        515                 520                 525
Asp Leu Ile Ser Val Leu Pro Phe Gly Asn Thr Ile Ala Gln Ile Asp
    530                 535                 540
Val Lys Gly Ser Asp Val Trp Thr Ala Phe Glu His Ser Leu Gly Ala
545                 550                 555                 560
Pro Thr Thr Gln Lys Asp Gly Lys Thr Val Leu Thr Ala Asn Gly Gly
                565                 570                 575
Leu Leu His Ile Ser Asp Ser Ile Arg Val Tyr Asp Ile Asn Lys
            580                 585                 590
Pro Ser Gly Lys Arg Ile Asn Ala Ile Gln Ile Leu Asn Lys Glu Thr
        595                 600                 605
Gly Lys Phe Glu Asn Ile Asp Leu Lys Arg Val Tyr His Val Thr Met
```

```
            610                 615                 620
Asn Asp Phe Thr Ala Ser Gly Gly Asp Gly Tyr Ser Met Phe Gly Gly
625                 630                 635                 640

Pro Arg Glu Glu Gly Ile Ser Leu Asp Gln Val Leu Ala Ser Tyr Leu
                645                 650                 655

Lys Thr Ala Asn Leu Ala Lys Tyr Asp Thr Thr Glu Pro Gln Arg Met
                660                 665                 670

Leu Leu Gly Lys Pro Ala Val Ser Glu Gln Pro Ala Lys Gly Gln Gln
                675                 680                 685

Gly Ser Lys Gly Ser Lys Ser Gly Lys Asp Thr Gln Pro Ile Gly Asp
690                 695                 700

Asp Lys Val Met Asp Pro Ala Lys Lys Pro Ala Pro Gly Lys Val Val
705                 710                 715                 720

Leu Leu Leu Ala His Arg Gly Thr Val Ser Gly Thr Glu Gly Ser
                725                 730                 735

Gly Arg Thr Ile Glu Gly Ala Thr Val Ser Ser Lys Ser Gly Lys Gln
                740                 745                 750

Leu Ala Arg Met Ser Val Pro Lys Gly Ser Ala His Glu Lys Gln Leu
                755                 760                 765

Pro Lys Thr Gly Thr Asn Gln Ser Ser Ser Pro Glu Ala Met Phe Val
                770                 775                 780

Leu Leu Ala Gly Ile Gly Leu Ile Ala Thr Val Arg Arg Arg Lys Ala
785                 790                 795                 800

Ser

<210> SEQ ID NO 13
<211> LENGTH: 4914
<212> TYPE: DNA
<213> ORGANISM: Staphylococcus epidermidis

<400> SEQUENCE: 13
agtggaaaat atggaaaaag gagtatgcaa atgagagata agaaaggacc ggtaaataaa     60
agagtagatt ttctatcaaa taaattgaat aaatattcaa taagaaaatt tacagttgga    120
acagcatcta ttttaattgg ctcactaatg tatttgggaa ctcaacaaga ggcagaagca    180
gctgaaaaca atattgagaa tccaactaca ttaaaagata tgtccaatc aaaagaagtg    240 aagattgaag aagtaacaaa caaagacact gcaccacagg gtgtagaagc taaatctgaa    300
gtaacttcaa acaaagacac aatcgaacat gaaccatcag taaaagctga agatatatca    360
aaaaaggagg atacaccaaa agaagtagct gatgttgctg aagttcagcc gaaatcgtca    420
gtcactcata acgcagagac acctaaggtt agaaaagctc gttctgttga tgaaggctct    480
tttgatatta caagagattc taaaaatgta gttgaatcta ccccaattac aattcaaggt    540
aaagaacatt ttgaaggtta cggaagtgtt gatatacaaa aaaaaccaac agatttaggg    600
gtatcagagg taaccaggtt taatgttggt aatgaaagta tggtttgat aggagcttta    660 caattaaaaa ataaaataga ttttagtaag gatttcaatt ttaaagttag agtggcaaat    720
aaccatcaat caaataccac aggtgctgat ggttgggggt tcttatttag taaaggaaat    780
gcagaagaat atttaactaa tggtggaatc cttggggata aggtctggt aaattcaggc    840 ggatttaaaa ttgatactgg atacatttat acaagttcca tggacaaaac tgaaaagcaa    900
gctggacaag ttatagagg atacggagct tttgtgaaaa atgacagttc tggtaattca    960
caaatggttg agaaaatat tgataaatca aaaactaatt ttttaaacta tgcggacaat   1020
tcaactaata catcagatgg aaagtttcat gggcaacgtt taaatgatgt catcttaact   1080
```

```
tatgttgctt caactggtaa aatgagagca gaatatgctg gtaaaacttg ggagacttca    1140
ataacagatt taggtttatc taaaaatcag gcatataatt tcttaattac atctagtcaa    1200
agatggggcc ttaatcaagg gataaatgca aatggctgga tgagaactga cttgaaaggt    1260
tcagagttta cttttacacc agaagcgcca aaaacaataa cagaattaga aaaaaaagtt    1320
gaagagattc cattcaagaa agaacgtaaa tttaatccgg atttagcacc agggacagaa    1380
aaagtaacaa gagaaggaca aaaaggtgag aagacaataa cgacaccaac actaaaaaat    1440
ccattaactg gagtaattat tagtaaaggt gaaccaaaag aagagattac aaaagatccg    1500
attaatgaat taacagaata cggacctgaa acaatagcgc caggtcatcg agacgaattt    1560
gatccgaagt taccaacagg agagaaagag gaagttccag gtaaaccagg aattaagaat    1620
ccagaaacag gagacgtagt tagaccgccg gtcgatagcg taacaaaata tggacctgta    1680
aaaggagact cgattgtaga aaagaagag attccattcg agaaagaacg taaatttaat    1740
cctgatttag caccagggac agaaaaagta acaagagaag gacaaaaagg tgagaagaca    1800
ataacgacgc caacactaaa aaatccatta actggagaaa ttattagtaa aggtgaatcg    1860
aaagaagaaa tcacaaaaga tccgattaat gaattaacag aatacggacc agaaacgata    1920
acaccaggtc atcgagacga atttgatccg aagttaccaa caggagagaa agaggaagtt    1980
ccaggtaaac caggaattaa gaatccgaaa acaggagatg tagttagacc accggtcgat    2040
agcgtaacaa aatatggacc tgtaaaagga gactcgattg tagaaaaaga gagattcca    2100 ttcgagaaag aacgtaaatt taatcctgat ttagcaccag ggacagaaaa agtaacaaga    2160
gaaggacaaa aggtgagaa gacaataacg acaccaacac taaaaaatcc attaactgga    2220
gtaattatta gtaaaggtga accaaaagaa gaaatcacaa aagatccgat taatgaatta    2280
acagaatacg gaccagaaac gataacacca ggtcatcgag acgaatttga tccgaagtta    2340
ccaacaggag agaagaaga gttccaggt aaaccaggaa ttaagaatcc agaaacagga    2400
gacgtagtta gaccaccggt cgatagcgta acaaaatatg gacctgtaaa aggagactcg    2460
attgtagaaa aagaagagat tccattcaag aaagaacgta aatttaatcc ggatttagca    2520
ccagggacag aaaaagtaac aagagaagga caaaaaggtg agaagacaat aacgacgcca    2580
acactaaaaa atccattaac tggagaaatt attagtaaag gtgaatcgaa agaagaaatc    2640
acaaaagatc cgattaatga attaacagaa tacggaccag aaacgataac accaggtcat    2700
cgagacgaat ttgatccgaa gttaccaaca ggagagaaag aggaagttcc aggtaaacca    2760
ggaattaaga atccagaaac aggagatgta gttagaccac cggtcgatag cgtaacaaaa    2820
tatggacctg taaaaggaga ctcgattgta gaaaagaag agattccatt cgagaaagaa    2880
cgtaaattta tcctgattt agcaccaggg acagaaaaag taacaagaga aggacaaaaa    2940
ggtgagaaga caataacgac gccaacacta aaaaatccat taactggaga aattattagt    3000
aaaggtgaat cgaaagaaga aatcacaaaa gatccgatta tgaattaac agaatacgga    3060 ccagaaacga taacaccagg tcatcgagac gaatttgatc cgaagttacc aacaggagag    3120
aaagaggaag ttccaggtaa accaggaatt aagaatccag aaacaggaga cgtagttaga    3180
ccaccggtcg atagcgtaac aaaatatgga cctgtaaaag gagactcgat tgtagaaaaa    3240
gaagaaattc cattcaagaa agaacgtaaa tttaatcctg atttagcacc agggacagaa    3300
aaagtaacaa gagaaggaca aaaaggtgag aagacaataa cgacgccaac actaaaaaat    3360
ccattaactg gagaaattat tagtaaaggt gaatcgaaag aagaaatcac aaaagatccg    3420
attaatgaat taacagaata cggaccagaa acgataacac caggtcatcg agacgaattt    3480
```

-continued

```
gatccgaagt taccaacagg agagaaagag gaagttccag gtaaaccagg aattaagaat    3540
ccagaaacag gagatgtagt tagaccaccg gtcgatagcg taacaaaata tggacctgta    3600
aaaggagact cgattgtaga aaagaagaa attccattcg agaaagaacg taaatttaat    3660
cctgatttag caccagggac agaaaaagta acaagagaag gacaaaaagg tgagaagaca    3720
ataacgacgc caacactaaa aaatccatta actggagaaa ttattagtaa aggtgaatcg    3780
aaagaagaaa tcacaaaaga tccgattaat gaattaacag aatacggacc agaaacgata    3840
acaccaggtc atcgagacga atttgatccg aagttaccaa caggagagaa agaggaagtt    3900
ccaggtaaac caggaattaa gaatccagaa acaggagatg tagttagacc accggtcgat    3960
agcgtaacaa aatatggacc tgtaaaagga gactcgattg tagaaaaaga agaaattcca    4020
ttcgagaaag aacgtaaatt taatcctgat ttagcaccag ggacagaaaa agtaacaaga    4080
gaaggacaaa aaggtgagaa gacaataacg acgccaacac taaaaaatcc attaactgga    4140
gaaattatta gtaaaggtga atcgaaagaa gaaatcacaa aagatccagt taatgaatta    4200
acagaattcg gtggcgagaa ataccgcaa ggtcataaag atatctttga tccaaactta    4260
ccaacagatc aaacgaaaaa agtaccaggt aaaccaggaa tcaagaatcc agacacagga    4320
aaagtgatcg aagagccagt ggatgatgtg attaaacacg gaccaaaaac gggtacacca    4380
gaaacaaaaa cagtagagat accgtttgaa acaaaacgtg agtttaatcc aaaattacaa    4440
cctggtgaag agcgagtgaa acaagaagga caaccaggaa gtaagacaat cacaacacca    4500
atcacagtga acccattaac aggtgaaaaa gttggcgagg gtcaaccaac agaagagatc    4560
acaaaacaac cagtagataa gattgtagag ttcggtggag agaaaccaaa agatccaaaa    4620
ggacctgaaa acccagagaa gccgagcaga ccaactcatc caagtggccc agtaaatcct    4680
aacaatccag gattatcgaa agacagagca aaaccaaatg gcccagttca ttcaatggat    4740
aaaaatgata agttaaaaaa atctaaaatt gctaaagaat cagtagctaa tcaagagaaa    4800
aaacgagcag aattaccaaa aacaggttta gaaagcacgc aaaaaggttt gatctttagt    4860
agtataattg gaattgctgg attaatgtta ttggctcgta gaagaaagaa ttaa          4914
```

<210> SEQ ID NO 14
<211> LENGTH: 1637
<212> TYPE: PRT
<213> ORGANISM: Staphylococcus epidermidis

<400> SEQUENCE: 14

```
Ser Gly Lys Tyr Gly Lys Arg Ser Met Gln Met Arg Asp Lys Lys Gly
1               5                   10                  15

Pro Val Asn Lys Arg Val Asp Phe Leu Ser Asn Lys Leu Asn Lys Tyr
            20                  25                  30

Ser Ile Arg Lys Phe Thr Val Gly Thr Ala Ser Ile Leu Ile Gly Ser
        35                  40                  45

Leu Met Tyr Leu Gly Thr Gln Gln Glu Ala Glu Ala Ala Glu Asn Asn
    50                  55                  60

Ile Glu Asn Pro Thr Thr Leu Lys Asp Asn Val Gln Ser Lys Glu Val
65                  70                  75                  80

Lys Ile Glu Glu Val Thr Asn Lys Asp Thr Ala Pro Gln Gly Val Glu
                85                  90                  95

Ala Lys Ser Glu Val Thr Ser Asn Lys Asp Thr Ile Glu His Glu Pro
            100                 105                 110

Ser Val Lys Ala Glu Asp Ile Ser Lys Lys Glu Asp Thr Pro Lys Glu
        115                 120                 125
```

```
Val Ala Asp Val Ala Glu Val Gln Pro Lys Ser Ser Val Thr His Asn
    130                 135                 140

Ala Glu Thr Pro Lys Val Arg Lys Ala Arg Ser Val Asp Glu Gly Ser
145                 150                 155                 160

Phe Asp Ile Thr Arg Asp Ser Lys Asn Val Val Glu Ser Thr Pro Ile
                165                 170                 175

Thr Ile Gln Gly Lys Glu His Phe Gly Tyr Gly Ser Val Asp Ile
            180                 185                 190

Gln Lys Lys Pro Thr Asp Leu Gly Val Ser Glu Val Thr Arg Phe Asn
        195                 200                 205

Val Gly Asn Glu Ser Asn Gly Leu Ile Gly Ala Leu Gln Leu Lys Asn
    210                 215                 220

Lys Ile Asp Phe Ser Lys Asp Phe Asn Phe Lys Val Arg Val Ala Asn
225                 230                 235                 240

Asn His Gln Ser Asn Thr Thr Gly Ala Asp Gly Trp Gly Phe Leu Phe
                245                 250                 255

Ser Lys Gly Asn Ala Glu Glu Tyr Leu Thr Asn Gly Gly Ile Leu Gly
            260                 265                 270

Asp Lys Gly Leu Val Asn Ser Gly Phe Lys Ile Asp Thr Gly Tyr
        275                 280                 285

Ile Tyr Thr Ser Ser Met Asp Lys Thr Glu Lys Gln Ala Gly Gln Gly
    290                 295                 300

Tyr Arg Gly Tyr Gly Ala Phe Val Lys Asn Asp Ser Ser Gly Asn Ser
305                 310                 315                 320

Gln Met Val Gly Glu Asn Ile Asp Lys Ser Lys Thr Asn Phe Leu Asn
                325                 330                 335

Tyr Ala Asp Asn Ser Thr Asn Thr Ser Asp Gly Lys Phe His Gly Gln
            340                 345                 350

Arg Leu Asn Asp Val Ile Leu Thr Tyr Val Ala Ser Thr Gly Lys Met
        355                 360                 365

Arg Ala Glu Tyr Ala Gly Lys Thr Trp Glu Thr Ser Ile Thr Asp Leu
370                 375                 380

Gly Leu Ser Lys Asn Gln Ala Tyr Asn Phe Leu Ile Thr Ser Ser Gln
385                 390                 395                 400

Arg Trp Gly Leu Asn Gln Gly Ile Asn Ala Asn Gly Trp Met Arg Thr
                405                 410                 415

Asp Leu Lys Gly Ser Glu Phe Thr Phe Thr Pro Glu Ala Pro Lys Thr
            420                 425                 430

Ile Thr Glu Leu Glu Lys Lys Val Glu Glu Ile Pro Phe Lys Lys Glu
        435                 440                 445

Arg Lys Phe Asn Pro Asp Leu Ala Pro Gly Thr Glu Lys Val Thr Arg
    450                 455                 460

Glu Gly Gln Lys Gly Glu Lys Thr Ile Thr Thr Pro Thr Leu Lys Asn
465                 470                 475                 480

Pro Leu Thr Gly Val Ile Ile Ser Lys Gly Glu Pro Lys Glu Glu Ile
                485                 490                 495

Thr Lys Asp Pro Ile Asn Glu Leu Thr Glu Tyr Gly Pro Glu Thr Ile
            500                 505                 510

Ala Pro Gly His Arg Asp Glu Phe Asp Pro Lys Leu Pro Thr Gly Glu
        515                 520                 525

Lys Glu Glu Val Pro Gly Lys Pro Gly Ile Lys Asn Pro Glu Thr Gly
    530                 535                 540

Asp Val Val Arg Pro Pro Val Asp Ser Val Thr Lys Tyr Gly Pro Val
```

```
                545                 550                 555                 560
Lys Gly Asp Ser Ile Val Glu Lys Glu Ile Pro Phe Glu Lys Glu
                565                 570                 575

Arg Lys Phe Asn Pro Asp Leu Ala Pro Gly Thr Glu Lys Val Thr Arg
                580                 585                 590

Glu Gly Gln Lys Gly Glu Lys Thr Ile Thr Thr Pro Thr Leu Lys Asn
                595                 600                 605

Pro Leu Thr Gly Glu Ile Ile Ser Lys Gly Ser Lys Glu Glu Ile
610                 615                 620

Thr Lys Asp Pro Ile Asn Glu Leu Thr Glu Tyr Gly Pro Glu Thr Ile
625                 630                 635                 640

Thr Pro Gly His Arg Asp Glu Phe Asp Pro Lys Leu Pro Thr Gly Glu
                645                 650                 655

Lys Glu Glu Val Pro Gly Lys Pro Gly Ile Lys Asn Pro Glu Thr Gly
                660                 665                 670

Asp Val Val Arg Pro Pro Val Asp Ser Val Thr Lys Tyr Gly Pro Val
                675                 680                 685

Lys Gly Asp Ser Ile Val Glu Lys Glu Ile Pro Phe Glu Lys Glu
                690                 695                 700

Arg Lys Phe Asn Pro Asp Leu Ala Pro Gly Thr Glu Lys Val Thr Arg
705                 710                 715                 720

Glu Gly Gln Lys Gly Glu Lys Thr Ile Thr Thr Pro Thr Leu Lys Asn
                725                 730                 735

Pro Leu Thr Gly Val Ile Ile Ser Lys Gly Glu Pro Lys Glu Glu Ile
                740                 745                 750

Thr Lys Asp Pro Ile Asn Glu Leu Thr Glu Tyr Gly Pro Glu Thr Ile
                755                 760                 765

Thr Pro Gly His Arg Asp Glu Phe Asp Pro Lys Leu Pro Thr Gly Glu
                770                 775                 780

Lys Glu Glu Val Pro Gly Lys Pro Gly Ile Lys Asn Pro Glu Thr Gly
785                 790                 795                 800

Asp Val Val Arg Pro Pro Val Asp Ser Val Thr Lys Tyr Gly Pro Val
                805                 810                 815

Lys Gly Asp Ser Ile Val Glu Lys Glu Ile Pro Phe Lys Lys Glu
                820                 825                 830

Arg Lys Phe Asn Pro Asp Leu Ala Pro Gly Thr Glu Lys Val Thr Arg
                835                 840                 845

Glu Gly Gln Lys Gly Glu Lys Thr Ile Thr Thr Pro Thr Leu Lys Asn
                850                 855                 860

Pro Leu Thr Gly Glu Ile Ile Ser Lys Gly Glu Ser Lys Glu Glu Ile
865                 870                 875                 880

Thr Lys Asp Pro Ile Asn Glu Leu Thr Glu Tyr Gly Pro Glu Thr Ile
                885                 890                 895

Thr Pro Gly His Arg Asp Glu Phe Asp Pro Lys Leu Pro Thr Gly Glu
                900                 905                 910

Lys Glu Glu Val Pro Gly Lys Pro Gly Ile Lys Asn Pro Glu Thr Gly
                915                 920                 925

Asp Val Val Arg Pro Pro Val Asp Ser Val Thr Lys Tyr Gly Pro Val
                930                 935                 940

Lys Gly Asp Ser Ile Val Glu Lys Glu Ile Pro Phe Glu Lys Glu
945                 950                 955                 960

Arg Lys Phe Asn Pro Asp Leu Ala Pro Gly Thr Glu Lys Val Thr Arg
                965                 970                 975
```

-continued

```
Glu Gly Gln Lys Gly Glu Lys Thr Ile Thr Thr Pro Thr Leu Lys Asn
            980                 985                 990

Pro Leu Thr Gly Glu Ile Ile Ser Lys Gly Glu Ser Lys Glu Glu Ile
            995                1000                1005

Thr Lys Asp Pro Ile Asn Glu Leu Thr Glu Tyr Gly Pro Glu Thr
        1010                1015                1020

Ile Thr Pro Gly His Arg Asp Glu Phe Asp Pro Lys Leu Pro Thr
        1025                1030                1035

Gly Glu Lys Glu Glu Val Pro Gly Lys Pro Gly Ile Lys Asn Pro
        1040                1045                1050

Glu Thr Gly Asp Val Val Arg Pro Pro Val Asp Ser Val Thr Lys
        1055                1060                1065

Tyr Gly Pro Val Lys Gly Asp Ser Ile Val Glu Lys Glu Glu Ile
        1070                1075                1080

Pro Phe Lys Lys Glu Arg Lys Phe Asn Pro Asp Leu Ala Pro Gly
        1085                1090                1095

Thr Glu Lys Val Thr Arg Glu Gly Gln Lys Gly Glu Lys Thr Ile
        1100                1105                1110

Thr Thr Pro Thr Leu Lys Asn Pro Leu Thr Gly Glu Ile Ile Ser
        1115                1120                1125

Lys Gly Glu Ser Lys Glu Ile Thr Lys Asp Pro Ile Asn Glu
        1130                1135                1140

Leu Thr Glu Tyr Gly Pro Glu Thr Ile Thr Pro Gly His Arg Asp
        1145                1150                1155

Glu Phe Asp Pro Lys Leu Pro Thr Gly Glu Lys Glu Val Pro
        1160                1165                1170

Gly Lys Pro Gly Ile Lys Asn Pro Glu Thr Gly Asp Val Val Arg
        1175                1180                1185

Pro Pro Val Asp Ser Val Thr Lys Tyr Gly Pro Val Lys Gly Asp
        1190                1195                1200

Ser Ile Val Glu Lys Glu Glu Ile Pro Phe Glu Lys Glu Arg Lys
        1205                1210                1215

Phe Asn Pro Asp Leu Ala Pro Gly Thr Glu Lys Val Thr Arg Glu
        1220                1225                1230

Gly Gln Lys Gly Glu Lys Thr Ile Thr Thr Pro Thr Leu Lys Asn
        1235                1240                1245

Pro Leu Thr Gly Glu Ile Ile Ser Lys Gly Glu Ser Lys Glu Glu
        1250                1255                1260

Ile Thr Lys Asp Pro Ile Asn Glu Leu Thr Glu Tyr Gly Pro Glu
        1265                1270                1275

Thr Ile Thr Pro Gly His Arg Asp Glu Phe Asp Pro Lys Leu Pro
        1280                1285                1290

Thr Gly Glu Lys Glu Glu Val Pro Gly Lys Pro Gly Ile Lys Asn
        1295                1300                1305

Pro Glu Thr Gly Asp Val Val Arg Pro Pro Val Asp Ser Val Thr
        1310                1315                1320

Lys Tyr Gly Pro Val Lys Gly Asp Ser Ile Val Glu Lys Glu Glu
        1325                1330                1335

Ile Pro Phe Glu Lys Glu Arg Lys Phe Asn Pro Asp Leu Ala Pro
        1340                1345                1350

Gly Thr Glu Lys Val Thr Arg Glu Gly Gln Lys Gly Glu Lys Thr
        1355                1360                1365

Ile Thr Thr Pro Thr Leu Lys Asn Pro Leu Thr Gly Glu Ile Ile
        1370                1375                1380
```

```
Ser Lys Gly Glu Ser Lys Glu   Glu Ile Thr Lys Asp   Pro Val Asn
    1385            1390                1395

Glu Leu Thr Glu Phe Gly Gly   Glu Lys Ile Pro Gln   Gly His Lys
    1400            1405                1410

Asp Ile Phe Asp Pro Asn Leu   Pro Thr Asp Gln Thr   Glu Lys Val
    1415            1420                1425

Pro Gly Lys Pro Gly Ile Lys   Asn Pro Asp Thr Gly   Lys Val Ile
    1430            1435                1440

Glu Glu Pro Val Asp Asp Val   Ile Lys His Gly Pro   Lys Thr Gly
    1445            1450                1455

Thr Pro Glu Thr Lys Thr Val   Glu Ile Pro Phe Glu   Thr Lys Arg
    1460            1465                1470

Glu Phe Asn Pro Lys Leu Gln   Pro Gly Glu Glu Arg   Val Lys Gln
    1475            1480                1485

Glu Gly Gln Pro Gly Ser Lys   Thr Ile Thr Thr Pro   Ile Thr Val
    1490            1495                1500

Asn Pro Leu Thr Gly Glu Lys   Val Gly Glu Gly Gln   Pro Thr Glu
    1505            1510                1515

Glu Ile Thr Lys Gln Pro Val   Asp Lys Ile Val Glu   Phe Gly Gly
    1520            1525                1530

Glu Lys Pro Lys Asp Pro Lys   Gly Pro Glu Asn Pro   Glu Lys Pro
    1535            1540                1545

Ser Arg Pro Thr His Pro Ser   Gly Pro Val Asn Pro   Asn Asn Pro
    1550            1555                1560

Gly Leu Ser Lys Asp Arg Ala   Lys Pro Asn Gly Pro   Val His Ser
    1565            1570                1575

Met Asp Lys Asn Asp Lys Val   Lys Lys Ser Lys Ile   Ala Lys Glu
    1580            1585                1590

Ser Val Ala Asn Gln Glu Lys   Lys Arg Ala Glu Leu   Pro Lys Thr
    1595            1600                1605

Gly Leu Glu Ser Thr Gln Lys   Gly Leu Ile Phe Ser   Ser Ile Ile
    1610            1615                1620

Gly Ile Ala Gly Leu Met Leu   Leu Ala Arg Arg Arg   Lys Asn
    1625            1630                1635

<210> SEQ ID NO 15
<211> LENGTH: 1923
<212> TYPE: DNA
<213> ORGANISM: Staphylococcus epidermidis

<400> SEQUENCE: 15
ggaaggagta tgttgatggc taaatatcga gggaaaccgt tcaattata tgtaaagtta      60 tcgtgttcga caatgatggc gacaagtatc attttaacga atatcttgcc gtacgatgcc    120
caagctgcat ctgaaaagga tactgaaatt acaaaagaga tattatctaa gcaagattta    180
ttagacaaag ttgacaaggc aattcgtcaa attgagcaat aaaacagtt atcggcttca     240 tctaaagaac attataaagc acaactaaat gaagcgaaaa cagcatcgca aatagatgaa    300
atcataaaac gagctaatga gttggatagc aaagacaata aaagttctca cactgaaatg    360
aacggtcaaa gtgatataga cagtaaatta gatcaattgc ttaaagattt aaatgaggtt    420
tcttcaaatg ttgatagggg tcaacaaagt ggcgaggacg atcttaatgc aatgaaaaat    480
gatatgtcac aaacggctac aacaaaacat ggagaaaaag atgataaaaa tgatgaagca    540
atggtaaata aggcgttaga agacctagac catttgaatc agcaaataca caatcgaaa     600
```

-continued

```
gatgcatcga aagatacatc ggaagatcca gcagtgtcta caacagataa taatcatgaa    660
gtagctaaaa cgccaaataa tgatggttct ggacatgttg tgttaaataa attcctttca    720
aatgaagaga atcaaagcca tagtaatcga ctcactgata aattacaagg aagcgataaa    780
attaatcatg ctatgattga aaaattagct aaaagtaatg cctcaacgca acattacaca    840
tatcataaac tgaatacgtt acaatcttta gatcaacgta ttgcaaatac gcaacttcct    900
aaaaatcaaa aatcagactt aatgagcgaa gtaaataaga cgaaagagcg tataaaaagt    960
caacgaaata ttattttgga agaacttgca cgtactgatg ataaaaagta tgctacacaa   1020
agcattttag aaagtatatt taataaagac gaggcagtta aaattctaaa agatatacgt   1080
gttgatggta aaacagatca acaaattgca gatcaaatta ctcgtcatat tgatcaatta   1140
tctctgacaa cgagtgatga tttattaacg tcattgattg atcaatcaca agataagtcg   1200
ctattgattt ctcaaatttt acaaacgaaa ttaggaaaag ctgaagcaga taaattggct   1260
aaagattgga cgaataaagg attatcaaat cgccaaatcg ttgaccaatt gaagaaacat   1320
tttgcatcaa ctggcgacac gtcttcagat gatatattaa aagcaatttt gaataatgcc   1380
aaagataaaa acaagcaat tgaaacgatt ttagcaacac gtatagaaag acaaaaggca   1440
aaattactgg cagatttaat tactaaaata gaaacagatc aaaataaaat tttaattta   1500 gttaaatcgg cattgaatgg taaagcggat gatttattga atttacaaaa gagactcaat   1560
caaacgaaaa aagatataga ttatatttta tcaccaatag taaatcgtcc aagtttacta   1620
gatcgattga ataaaaatgg gaaaacgaca gatttaaata agttagcaaa tttaatgaat   1680
caaggatcag atttattaga cagtattcca gatatacca caccaaagcc agaaaagacg   1740
ttaacacttg gtaaaggtaa tggattgtta agtggattat aaatgctga tggtaatgta   1800 tctttgccta aagcggggga aacgataaaa gaacattggt tgccgatatc tgtaattgtt   1860
ggtgcaatgg gtgtactaat gatttggtta tcacgacgca ataagttgaa aaataaagca   1920
taa                                                                 1923
```

<210> SEQ ID NO 16
<211> LENGTH: 640
<212> TYPE: PRT
<213> ORGANISM: Staphylococcus epidermidis

<400> SEQUENCE: 16

```
Gly Arg Ser Met Leu Met Ala Lys Tyr Arg Gly Lys Pro Phe Gln Leu
1               5                   10                  15

Tyr Val Lys Leu Ser Cys Ser Thr Met Met Ala Thr Ser Ile Ile Leu
            20                  25                  30

Thr Asn Ile Leu Pro Tyr Asp Ala Gln Ala Ala Ser Glu Lys Asp Thr
        35                  40                  45

Glu Ile Thr Lys Glu Ile Leu Ser Lys Gln Asp Leu Leu Asp Lys Val
    50                  55                  60

Asp Lys Ala Ile Arg Gln Ile Glu Gln Leu Lys Gln Leu Ser Ala Ser
65                  70                  75                  80

Ser Lys Glu His Tyr Lys Ala Gln Leu Asn Glu Ala Lys Thr Ala Ser
                85                  90                  95

Gln Ile Asp Glu Ile Ile Lys Arg Ala Asn Glu Leu Asp Ser Lys Asp
            100                 105                 110

Asn Lys Ser Ser His Thr Glu Met Asn Gly Gln Ser Asp Ile Asp Ser
        115                 120                 125

Lys Leu Asp Gln Leu Leu Lys Asp Leu Asn Glu Val Ser Ser Asn Val
    130                 135                 140
```

Asp Arg Gly Gln Gln Ser Gly Glu Asp Asp Leu Asn Ala Met Lys Asn
145                 150                 155                 160

Asp Met Ser Gln Thr Ala Thr Thr Lys His Gly Glu Lys Asp Asp Lys
            165                 170                 175

Asn Asp Glu Ala Met Val Asn Lys Ala Leu Glu Asp Leu Asp His Leu
                180                 185                 190

Asn Gln Gln Ile His Lys Ser Lys Asp Ala Ser Lys Asp Thr Ser Glu
            195                 200                 205

Asp Pro Ala Val Ser Thr Thr Asp Asn Asn His Glu Val Ala Lys Thr
210                 215                 220

Pro Asn Asn Asp Gly Ser Gly His Val Val Leu Asn Lys Phe Leu Ser
225                 230                 235                 240

Asn Glu Glu Asn Gln Ser His Ser Asn Arg Leu Thr Asp Lys Leu Gln
            245                 250                 255

Gly Ser Asp Lys Ile Asn His Ala Met Ile Glu Lys Leu Ala Lys Ser
            260                 265                 270

Asn Ala Ser Thr Gln His Tyr Thr Tyr His Lys Leu Asn Thr Leu Gln
            275                 280                 285

Ser Leu Asp Gln Arg Ile Ala Asn Thr Gln Leu Pro Lys Asn Gln Lys
            290                 295                 300

Ser Asp Leu Met Ser Glu Val Asn Lys Thr Lys Glu Arg Ile Lys Ser
305                 310                 315                 320

Gln Arg Asn Ile Ile Leu Glu Glu Leu Ala Arg Thr Asp Asp Lys Lys
            325                 330                 335

Tyr Ala Thr Gln Ser Ile Leu Glu Ser Ile Phe Asn Lys Asp Glu Ala
            340                 345                 350

Val Lys Ile Leu Lys Asp Ile Arg Val Asp Gly Lys Thr Asp Gln Gln
            355                 360                 365

Ile Ala Asp Gln Ile Thr Arg His Ile Asp Gln Leu Ser Leu Thr Thr
            370                 375                 380

Ser Asp Asp Leu Leu Thr Ser Leu Ile Asp Gln Ser Gln Asp Lys Ser
385                 390                 395                 400

Leu Leu Ile Ser Gln Ile Leu Gln Thr Lys Leu Gly Lys Ala Glu Ala
            405                 410                 415

Asp Lys Leu Ala Lys Asp Trp Thr Asn Lys Gly Leu Ser Asn Arg Gln
            420                 425                 430

Ile Val Asp Gln Leu Lys Lys His Phe Ala Ser Thr Gly Asp Thr Ser
            435                 440                 445

Ser Asp Asp Ile Leu Lys Ala Ile Leu Asn Asn Ala Lys Asp Lys Lys
450                 455                 460

Gln Ala Ile Glu Thr Ile Leu Ala Thr Arg Ile Glu Arg Gln Lys Ala
465                 470                 475                 480

Lys Leu Leu Ala Asp Leu Ile Thr Lys Ile Glu Thr Asp Gln Asn Lys
            485                 490                 495

Ile Phe Asn Leu Val Lys Ser Ala Leu Asn Gly Lys Ala Asp Asp Leu
            500                 505                 510

Leu Asn Leu Gln Lys Arg Leu Asn Gln Thr Lys Lys Asp Ile Asp Tyr
            515                 520                 525

Ile Leu Ser Pro Ile Val Asn Arg Pro Ser Leu Leu Asp Arg Leu Asn
            530                 535                 540

Lys Asn Gly Lys Thr Thr Asp Leu Asn Lys Leu Ala Asn Leu Met Asn
545                 550                 555                 560

Gln Gly Ser Asp Leu Leu Asp Ser Ile Pro Asp Ile Pro Thr Pro Lys

```
                    565                 570                 575
Pro Glu Lys Thr Leu Thr Leu Gly Lys Gly Asn Gly Leu Leu Ser Gly
            580                 585                 590

Leu Leu Asn Ala Asp Gly Asn Val Ser Leu Pro Lys Ala Gly Glu Thr
            595                 600                 605

Ile Lys Glu His Trp Leu Pro Ile Ser Val Ile Val Gly Ala Met Gly
            610                 615                 620

Val Leu Met Ile Trp Leu Ser Arg Arg Asn Lys Leu Lys Asn Lys Ala
625                 630                 635                 640

<210> SEQ ID NO 17
<211> LENGTH: 522
<212> TYPE: PRT
<213> ORGANISM: Staphylococcus epidermidis

<400> SEQUENCE: 17

Ala Ser Glu Thr Pro Ile Thr Ser Glu Ile Ser Ser Asn Ser Glu Thr
1               5                   10                  15

Val Ala Asn Gln Asn Ser Thr Thr Ile Lys Asn Ser Gln Lys Glu Thr
            20                  25                  30

Val Asn Ser Thr Ser Leu Glu Ser Asn His Ser Asn Ser Thr Asn Lys
        35                  40                  45

Gln Met Ser Ser Glu Val Thr Asn Thr Ala Gln Ser Ser Glu Lys Ala
    50                  55                  60

Gly Ile Ser Gln Gln Ser Ser Glu Thr Ser Asn Gln Ser Ser Lys Leu
65                  70                  75                  80

Asn Thr Tyr Ala Ser Thr Asp His Val Glu Ser Thr Thr Ile Asn Asn
                85                  90                  95

Asp Asn Thr Ala Gln Gln Asp Gln Asn Lys Ser Ser Asn Val Thr Ser
            100                 105                 110

Lys Ser Thr Gln Ser Asn Thr Ser Ser Ser Glu Lys Asn Ile Ser Ser
        115                 120                 125

Asn Leu Thr Gln Ser Ile Glu Thr Lys Ala Thr Asp Ser Leu Ala Thr
    130                 135                 140

Ser Glu Ala Arg Thr Ser Thr Asn Gln Ile Ser Asn Leu Thr Ser Thr
145                 150                 155                 160

Ser Thr Ser Asn Gln Ser Ser Pro Thr Ser Phe Ala Asn Leu Arg Thr
                165                 170                 175

Phe Ser Arg Phe Thr Val Leu Asn Thr Met Ala Ala Pro Thr Thr Thr
            180                 185                 190

Ser Thr Thr Thr Thr Ser Ser Leu Thr Ser Asn Ser Val Val Val Asn
        195                 200                 205

Lys Asp Asn Phe Asn Glu His Met Asn Leu Ser Gly Ser Ala Thr Tyr
    210                 215                 220

Asp Pro Lys Thr Gly Ile Ala Thr Leu Thr Pro Asp Ala Tyr Ser Gln
225                 230                 235                 240

Lys Gly Ala Ile Ser Leu Asn Thr Arg Leu Asp Ser Asn Arg Ser Phe
                245                 250                 255

Arg Phe Ile Gly Lys Val Asn Leu Gly Asn Arg Tyr Glu Gly Tyr Ser
            260                 265                 270

Pro Asp Gly Val Ala Gly Gly Asp Gly Ile Gly Phe Ala Phe Ser Pro
        275                 280                 285

Gly Pro Leu Gly Gln Ile Gly Lys Glu Gly Ala Ala Val Gly Ile Gly
    290                 295                 300

Gly Leu Asn Asn Ala Phe Gly Phe Lys Leu Asp Thr Tyr His Asn Thr
```

```
                 305                 310                 315                 320
Ser Thr Pro Arg Ser Asp Ala Lys Ala Lys Ala Asp Pro Arg Asn Val
            325                 330                 335

Gly Gly Gly Ala Phe Gly Ala Phe Val Ser Thr Asp Arg Asn Gly
        340                 345                 350

Met Ala Thr Glu Glu Ser Thr Ala Ala Lys Leu Asn Val Gln Pro
        355                 360                 365

Thr Asp Asn Ser Phe Gln Asp Phe Val Ile Asp Tyr Asn Gly Asp Thr
    370                 375                 380

Lys Val Met Thr Val Thr Tyr Ala Gly Gln Thr Phe Thr Arg Asn Leu
385                 390                 395                 400

Thr Asp Trp Ile Lys Asn Ser Gly Gly Thr Thr Phe Ser Leu Ser Met
                405                 410                 415

Thr Ala Ser Thr Gly Gly Ala Lys Asn Leu Gln Gln Val Gln Phe Gly
            420                 425                 430

Thr Phe Glu Tyr Thr Glu Ser Ala Val Ala Lys Val Arg Tyr Val Asp
        435                 440                 445

Ala Asn Thr Gly Lys Asp Ile Ile Pro Pro Lys Thr Ile Ala Gly Glu
    450                 455                 460

Val Asp Gly Thr Val Asn Ile Asp Lys Gln Leu Asn Asn Phe Lys Asn
465                 470                 475                 480

Leu Gly Tyr Ser Tyr Val Gly Thr Asp Ala Leu Lys Ala Pro Asn Tyr
                485                 490                 495

Thr Glu Thr Ser Gly Thr Pro Thr Leu Lys Leu Thr Asn Ser Ser Gln
            500                 505                 510

Thr Val Ile Tyr Lys Phe Lys Asp Val Gln
        515                 520

<210> SEQ ID NO 18
<211> LENGTH: 485
<212> TYPE: PRT
<213> ORGANISM: Staphylococcus epidermidis

<400> SEQUENCE: 18

Ala Ser Asp Ala Pro Leu Thr Ser Glu Leu Asn Thr Gln Ser Glu Thr
1               5                   10                  15

Val Gly Asn Gln Asn Ser Thr Thr Ile Glu Ala Ser Thr Ser Thr Ala
            20                  25                  30

Asp Ser Thr Ser Val Thr Lys Asn Ser Ser Val Gln Thr Ser Asn
        35                  40                  45

Ser Asp Thr Val Ser Ser Glu Lys Ser Glu Lys Val Thr Ser Thr Thr
    50                  55                  60

Asn Ser Thr Ser Asn Gln Gln Glu Lys Leu Thr Ser Thr Ser Glu Ser
65                  70                  75                  80

Thr Ser Ser Lys Asn Thr Thr Ser Ser Ser Asp Thr Lys Ser Val Ala
                85                  90                  95

Ser Thr Ser Ser Thr Glu Gln Pro Ile Asn Thr Ser Thr Asn Gln Ser
            100                 105                 110

Thr Ala Ser Asn Asn Thr Ser Gln Ser Thr Thr Pro Ser Ser Val Asn
        115                 120                 125

Leu Asn Lys Thr Ser Thr Thr Ser Thr Ser Thr Ala Pro Val Lys Leu
    130                 135                 140

Arg Thr Phe Ser Arg Leu Ala Met Ser Thr Phe Ala Ser Ala Ala Thr
145                 150                 155                 160

Thr Thr Ala Val Thr Ala Asn Thr Ile Thr Val Asn Lys Asp Asn Leu
```

```
                        165                 170                 175
Lys Gln Tyr Met Thr Thr Ser Gly Asn Ala Thr Tyr Asp Gln Ser Thr
                180                 185                 190
Gly Ile Val Thr Leu Thr Gln Asp Ala Tyr Ser Gln Lys Gly Ala Ile
                195                 200                 205
Thr Leu Gly Thr Arg Ile Asp Ser Asn Lys Ser Phe His Phe Ser Gly
            210                 215                 220
Lys Val Asn Leu Gly Asn Lys Tyr Glu Gly His Gly Asn Gly Gly Asp
225                 230                 235                 240
Gly Ile Gly Phe Ala Phe Ser Pro Gly Val Leu Gly Glu Thr Gly Leu
                245                 250                 255
Asn Gly Ala Ala Val Gly Ile Gly Gly Leu Ser Asn Ala Phe Gly Phe
            260                 265                 270
Lys Leu Asp Thr Tyr His Asn Thr Ser Lys Pro Asn Ser Ala Ala Lys
        275                 280                 285
Ala Asn Ala Asp Pro Ser Asn Val Ala Gly Gly Ala Phe Gly Ala
    290                 295                 300
Phe Val Thr Thr Asp Ser Tyr Gly Val Ala Thr Thr Tyr Thr Ser Ser
305                 310                 315                 320
Ser Thr Ala Asp Asn Ala Ala Lys Leu Asn Val Gln Pro Thr Asn Asn
                325                 330                 335
Thr Phe Gln Asp Phe Asp Ile Asn Tyr Asn Gly Asp Thr Lys Val Met
            340                 345                 350
Thr Val Lys Tyr Ala Gly Gln Thr Trp Thr Arg Asn Ile Ser Asp Trp
        355                 360                 365
Ile Ala Lys Ser Gly Thr Thr Asn Phe Ser Leu Ser Met Thr Ala Ser
    370                 375                 380
Thr Gly Gly Ala Thr Asn Leu Gln Gln Val Gln Phe Gly Thr Phe Glu
385                 390                 395                 400
Tyr Thr Glu Ser Ala Val Thr Gln Val Arg Tyr Val Asp Val Thr Thr
                405                 410                 415
Gly Lys Asp Ile Ile Pro Pro Lys Thr Tyr Ser Gly Asn Val Asp Gln
            420                 425                 430
Val Val Thr Ile Asp Asn Gln Gln Ser Ala Leu Thr Ala Lys Gly Tyr
        435                 440                 445
Asn Tyr Thr Ser Val Asp Ser Ser Tyr Ala Ser Thr Tyr Asn Asp Thr
    450                 455                 460
Asn Lys Thr Val Lys Met Thr Asn Ala Gly Gln Ser Val Thr Tyr Tyr
465                 470                 475                 480
Phe Thr Asp Val Val
            485

<210> SEQ ID NO 19
<211> LENGTH: 1245
<212> TYPE: PRT
<213> ORGANISM: Staphylococcus epidermidis

<400> SEQUENCE: 19

Met Gly Lys Arg Arg Gln Gly Pro Ile Asn Lys Lys Val Asp Phe Leu
1               5                   10                  15
Pro Asn Lys Leu Asn Lys Tyr Ser Ile Arg Lys Phe Thr Val Gly Thr
                20                  25                  30
Ala Ser Ile Leu Leu Gly Ser Thr Leu Ile Phe Gly Ser Ser Ser His
            35                  40                  45
Glu Ala Lys Ala Ala Glu Glu Lys Gln Val Asp Pro Ile Thr Gln Ala
```

```
                50                   55                    60
Asn Gln Asn Asp Ser Ser Glu Arg Ser Leu Glu Asn Thr Asn Gln Pro
 65                  70                  75                  80

Thr Val Asn Asn Glu Ala Pro Gln Met Ser Ser Thr Leu Gln Ala Glu
                 85                  90                  95

Glu Gly Ser Asn Ala Glu Ala Pro Gln Ser Glu Pro Thr Lys Ala Glu
                100                 105                 110

Glu Gly Gly Asn Ala Glu Ala Gln Ser Glu Pro Thr Lys Ala Glu
                115                 120                 125

Glu Gly Gly Asn Ala Glu Ala Pro Gln Ser Glu Pro Thr Lys Ala Glu
130                 135                 140

Glu Gly Gly Asn Ala Glu Ala Gln Ser Glu Pro Thr Lys Thr Glu
145                 150                 155                 160

Glu Gly Ser Asn Val Lys Ala Ala Gln Ser Glu Pro Thr Lys Ala Glu
                165                 170                 175

Glu Gly Ser Asn Ala Glu Ala Pro Gln Ser Glu Pro Thr Lys Thr Glu
                180                 185                 190

Glu Gly Ser Asn Ala Lys Ala Ala Gln Ser Glu Pro Thr Lys Ala Glu
                195                 200                 205

Glu Gly Gly Asn Ala Glu Ala Ala Gln Ser Glu Pro Thr Lys Thr Glu
                210                 215                 220

Glu Gly Ser Asn Ala Glu Ala Pro Gln Ser Glu Pro Thr Lys Ala Glu
225                 230                 235                 240

Glu Gly Gly Asn Ala Glu Ala Pro Gln Ser Glu Pro Thr Lys Thr Glu
                245                 250                 255

Glu Gly Gly Asn Ala Glu Ala Pro Asn Val Pro Thr Ile Lys Ala Asn
                260                 265                 270

Ser Asp Asn Asp Thr Gln Thr Gln Phe Ser Glu Ala Pro Thr Arg Asn
                275                 280                 285

Asp Leu Ala Arg Lys Glu Asp Ile Pro Ala Val Ser Lys Asn Glu Glu
                290                 295                 300

Leu Gln Ser Ser Gln Pro Asn Thr Asp Ser Lys Ile Glu Pro Thr Thr
305                 310                 315                 320

Ser Glu Pro Val Asn Leu Asn Tyr Ser Ser Pro Phe Met Ser Leu Leu
                325                 330                 335

Ser Met Pro Ala Asp Ser Ser Ser Asn Asn Thr Lys Asn Thr Ile Asp
                340                 345                 350

Ile Pro Pro Thr Thr Val Lys Gly Arg Asp Asn Tyr Asp Phe Tyr Gly
                355                 360                 365

Arg Val Asp Ile Glu Ser Asn Pro Thr Asp Leu Asn Ala Thr Asn Leu
370                 375                 380

Thr Arg Tyr Asn Tyr Gly Gln Pro Pro Gly Thr Thr Thr Ala Gly Ala
385                 390                 395                 400

Val Gln Phe Lys Asn Gln Val Ser Phe Asp Lys Asp Phe Asp Phe Asn
                405                 410                 415

Ile Arg Val Ala Asn Asn Arg Gln Ser Asn Thr Thr Gly Ala Asp Gly
                420                 425                 430

Trp Gly Phe Met Phe Ser Lys Lys Asp Gly Asp Phe Leu Lys Asn
                435                 440                 445

Gly Gly Ile Leu Arg Glu Lys Gly Thr Pro Ser Ala Ala Gly Phe Arg
                450                 455                 460

Ile Asp Thr Gly Tyr Tyr Asn Asn Asp Pro Leu Asp Lys Ile Gln Lys
465                 470                 475                 480
```

-continued

Gln Ala Gly Gln Gly Tyr Arg Gly Tyr Gly Thr Phe Val Lys Asn Asp
            485                 490                 495
Ser Gln Gly Asn Thr Ser Lys Val Gly Ser Gly Thr Pro Ser Thr Asp
            500                 505                 510
Phe Leu Asn Tyr Ala Asp Asn Thr Thr Asn Asp Leu Asp Gly Lys Phe
            515                 520                 525
His Gly Gln Lys Leu Asn Asn Val Asn Leu Lys Tyr Asn Ala Ser Asn
            530                 535                 540
Gln Thr Phe Thr Ala Thr Tyr Ala Gly Lys Thr Trp Thr Ala Thr Leu
545                 550                 555                 560
Ser Glu Leu Gly Leu Ser Pro Thr Asp Ser Tyr Asn Phe Leu Val Thr
            565                 570                 575
Ser Ser Gln Tyr Gly Asn Gly Asn Ser Gly Thr Tyr Ala Ser Gly Val
            580                 585                 590
Met Arg Ala Asp Leu Asp Gly Ala Thr Leu Thr Tyr Thr Pro Lys Ala
            595                 600                 605
Val Asp Gly Asp Pro Ile Ile Ser Thr Lys Glu Ile Pro Phe Asn Lys
            610                 615                 620
Lys Arg Glu Phe Asp Pro Asn Leu Ala Pro Gly Thr Glu Lys Val Val
625                 630                 635                 640
Gln Lys Gly Glu Pro Gly Ile Glu Thr Thr Thr Thr Pro Thr Tyr Val
            645                 650                 655
Asn Pro Asn Thr Gly Glu Lys Val Gly Glu Gly Pro Thr Glu Lys
            660                 665                 670
Ile Thr Lys Gln Pro Val Asp Glu Ile Val His Tyr Gly Gly Glu Glu
            675                 680                 685
Ile Lys Pro Gly His Lys Asp Glu Phe Asp Pro Asn Ala Pro Lys Gly
            690                 695                 700
Ser Gln Thr Thr Gln Pro Gly Lys Pro Gly Val Lys Asn Pro Asp Thr
705                 710                 715                 720
Gly Glu Val Val Thr Pro Pro Val Asp Asp Val Thr Lys Tyr Gly Pro
            725                 730                 735
Val Asp Gly Asp Pro Ile Thr Ser Thr Glu Glu Ile Pro Phe Asp Lys
            740                 745                 750
Lys Arg Glu Phe Asn Pro Asp Leu Lys Pro Gly Glu Glu Arg Val Lys
            755                 760                 765
Gln Lys Gly Glu Pro Gly Thr Lys Thr Ile Thr Thr Pro Thr Thr Lys
            770                 775                 780
Asn Pro Leu Thr Gly Glu Lys Val Gly Glu Gly Glu Pro Thr Glu Lys
785                 790                 795                 800
Ile Thr Lys Gln Pro Val Asp Glu Ile Thr Glu Tyr Gly Gly Glu Glu
            805                 810                 815
Ile Lys Pro Gly His Lys Asp Glu Phe Asp Pro Asn Ala Pro Lys Gly
            820                 825                 830
Ser Gln Glu Asp Val Pro Gly Lys Pro Gly Val Lys Asn Pro Gly Thr
            835                 840                 845
Gly Glu Val Val Thr Pro Pro Val Asp Asp Val Thr Lys Tyr Gly Pro
            850                 855                 860
Val Asp Gly Asp Pro Ile Thr Ser Thr Glu Glu Ile Pro Phe Asp Lys
865                 870                 875                 880
Lys Arg Glu Phe Asn Pro Asp Leu Lys Pro Gly Glu Glu Arg Val Lys
            885                 890                 895
Gln Lys Gly Glu Pro Gly Thr Lys Thr Ile Thr Thr Pro Thr Thr Lys
            900                 905                 910

```
Asn Pro Leu Thr Gly Glu Lys Val Gly Glu Gly Glu Pro Thr Glu Lys
        915                 920                 925
Ile Thr Lys Gln Pro Val Asp Glu Ile Val His Tyr Gly Gly Glu Gln
        930                 935                 940
Ile Pro Gln Gly His Lys Asp Glu Phe Asp Pro Asn Ala Pro Val Asp
945                 950                 955                 960
Ser Lys Thr Glu Val Pro Gly Lys Pro Gly Val Lys Asn Pro Asp Thr
            965                 970                 975
Gly Glu Val Val Thr Pro Pro Val Asp Asp Val Thr Lys Tyr Gly Pro
            980                 985                 990
Val Asp Gly Asp Ser Ile Thr Ser Thr Glu Glu Ile Pro Phe Asp Lys
            995                 1000                1005
Lys Arg Glu Phe Asp Pro Asn Leu Ala Pro Gly Thr Glu Lys Val
        1010                1015                1020
Val Gln Lys Gly Glu Pro Gly Thr Lys Thr Ile Thr Thr Pro Thr
        1025                1030                1035
Thr Lys Asn Pro Leu Thr Gly Glu Lys Val Gly Glu Gly Lys Ser
        1040                1045                1050
Thr Glu Lys Val Thr Lys Gln Pro Val Asp Glu Ile Val Glu Tyr
        1055                1060                1065
Gly Pro Thr Lys Ala Glu Pro Gly Lys Pro Ala Glu Pro Gly Lys
        1070                1075                1080
Pro Ala Glu Pro Gly Lys Pro Ala Glu Pro Gly Thr Pro Ala Glu
        1085                1090                1095
Pro Gly Lys Pro Ala Glu Pro Gly Thr Pro Ala Glu Pro Gly Lys
        1100                1105                1110
Pro Ala Glu Pro Gly Lys Pro Ala Glu Pro Gly Lys Pro Ala Glu
        1115                1120                1125
Pro Gly Lys Pro Ala Glu Pro Gly Thr Pro Ala Glu Pro Gly Thr
        1130                1135                1140
Pro Ala Glu Pro Gly Lys Pro Ala Glu Pro Gly Thr Pro Ala Glu
        1145                1150                1155
Pro Gly Lys Pro Ala Glu Pro Gly Thr Pro Ala Glu Pro Gly Lys
        1160                1165                1170
Pro Ala Glu Ser Gly Lys Pro Val Glu Pro Gly Thr Pro Ala Gln
        1175                1180                1185
Ser Gly Ala Pro Glu Gln Pro Asn Arg Ser Met His Ser Thr Asp
        1190                1195                1200
Asn Lys Asn Gln Leu Pro Asp Thr Gly Glu Asn Arg Gln Ala Asn
        1205                1210                1215
Glu Gly Thr Leu Val Gly Ser Leu Leu Ala Ile Val Gly Ser Leu
        1220                1225                1230
Phe Ile Phe Gly Arg Arg Lys Lys Gly Asn Glu Lys
        1235                1240                1245

<210> SEQ ID NO 20
<211> LENGTH: 3765
<212> TYPE: DNA
<213> ORGANISM: Staphylococcus epidermidis

<400> SEQUENCE: 20
atgggcaaac gtagacaagg tcctattaat aaaaaagtgg attttttacc taacaaatta      60
aacaagtatt ctataagaaa attcactgtt ggtacggcct caatattact tggttcgaca     120 cttattttg gaagtagtag ccatgaagcg aaagctgcag aagaaaaaca agttgatcca     180
```

-continued

```
attacacaag ctaatcaaaa tgatagtagt gaaagatcac ttgaaaacac aaatcaacct    240
actgtaaaca atgaagcacc acagatgtct tctacattgc aagcagaaga aggaagcaat    300
gcagaagcac ctcaatctga gccaacgaag gcagaagaag gaggcaatgc agaagcagct    360
caatctgagc caacgaaggc agaagaagga ggcaatgcag aagcacctca atctgagcca    420
acgaaggcag aagaaggagg caatgcagaa gcagctcaat ctgagccaac gaagacagaa    480
gaaggaagca acgtaaaagc agctcaatct gagccaacga aggcagaaga aggaagcaat    540
gcagaagcac ctcaatctga gccaacgaag acagaagaag gaagcaacgc aaaagcagct    600
caatctgagc caacgaaggc agaagaagga ggcaatgcag aagcagctca atctgagcca    660
acgaagacag aagaaggaag caatgcagaa gcacctcaat ctgagccaac gaaggcagaa    720
gaaggaggca atgcagaagc acctcaatct gagccaacga agacagaaga aggaggcaat    780
gcagaagcac cgaatgttcc aactatcaaa gctaattcag ataatgatac acaaacacaa    840
ttttcagaag cccctacaag aaatgaccta gctagaaaaa aagatatccc tgctgtttct    900
aaaaacgagg aattacaatc atcacaacca aacactgaca gtaaaataga acctacaact    960
tcagaacctg tgaatttaaa ttatagttct ccgtttatgt ccttattaag catgcctgct   1020
gatagttcat ccaataacac taaaaataca atagatatac cgccaactac ggttaaaggt   1080
agagataatt acgatttta cggtagagta gatatcgaaa gtaatcctac agatttaaat   1140
gcgacaaatt taacgagata taattatgga cagccacctg gtacaacaac agctggtgca   1200
gttcaattta aaaatcaagt tagttttgat aaagatttcg actttaacat tagagtagca   1260
aacaatcgtc aaagtaatac aactggtgca gatggttggg gctttatgtt cagcaagaaa   1320 gatgggatg atttcctaaa aaacggtggt atcttacgtg aaaaaggtac acctagtgca   1380
gctggtttca gaattgatac aggatattat aataacgatc cattagataa aatacagaaa   1440
caagctggtc aaggctatag agggtatggg acatttgtta aaaatgactc ccaaggtaat   1500
acttctaaag taggatcagg tactccatca acagattttc ttaactacgc agataatact   1560
actaatgatt tagatggtaa attccatggt caaaaattaa ataatgttaa tttgaaatat   1620
aatgcttcaa atcaaacttt tacagctact tatgctggta aaacttggac ggctacgtta   1680
tctgaattag gattgagtcc aactgatagt tacaattttt tagttacatc aagtcaatat   1740
ggaaatggta atagtggtac atacgcaagt ggcgttatga gagctgattt agatggtgca   1800
acattgacat acactcctaa agcagtcgat ggagatccaa ttatatcaac taaggaaata   1860
ccatttaata agaaacgtga atttgatcca aacttagccc caggtacaga aaaagtagtc   1920
caaaaaggtg aaccaggaat tgaaacaaca acaacaccaa cttatgtcaa tcctaataca   1980
ggagaaaaag ttggcgaagg tgaaccaaca gaaaaaataa caaaacaacc agtggatgaa   2040
atcgttcatt atggtggcga agaaatcaag ccaggccata aggatgaatt tgatccaaat   2100
gcaccgaaag gtagtcaaac aacgcaacca ggtaagccgg gggttaaaaa tcctgataca   2160
ggcgaagtag ttactccacc tgtggatgat gtgacaaaat atggtccagt tgatggagat   2220
ccgatcacgt caacggaaga aattccattc gacaagaaac gtgaattcaa tcctgattta   2280
aaaccaggtg aagagcgtgt taaacaaaaa ggtgaaccag gaacaaaaac aattacaaca   2340
ccaacaacta agaaccccatt aacagggaa aaagttggcg aaggtgaacc aacagaaaaa   2400
ataacaaaac aaccagtaga tgaaatcaca gaatatggtg gcgaagaaat caagccaggc   2460
cataaggatg aatttgatcc aaatgcaccg aaaggtagcc aagaggacgt tccaggtaaa   2520
ccaggagtta aaaaccctgg aacaggcgaa gtagtcacac caccagtgga tgatgtgaca   2580
```

```
aaatatggtc cagttgatgg agatccgatc acgtcaacgg aagaaattcc attcgacaag    2640
aaacgtgaat tcaatcctga tttaaaacca ggtgaagagc gcgttaaaca gaaaggtgaa    2700
ccaggaacaa aaacaattac aacgccaaca actaagaacc cattaacagg agaaaaagtt    2760
ggcgaaggtg aaccaacaga aaaataaca aaacaaccag tggatgagat tgttcattat    2820
ggtggtgaac aaataccaca aggtcataaa gatgaatttg atccaaatgc acctgtagat    2880
agtaaaactg aagttccagg taaaccagga gttaaaaatc ctgatacagg tgaagttgtt    2940
accccaccag tggatgatgt gacaaaatat ggtccagttg atggagattc gattacgtca    3000
acggaagaaa ttccgtttga taaaaaacgc gaatttgatc caaacttagc gccaggtaca    3060
gagaaagtcg ttcaaaaagg tgaaccagga acaaaaacaa ttacaacgcc aacaactaag    3120
aacccattaa caggagaaaa agttggcgaa ggtaaatcaa cagaaaaagt cactaaacaa    3180
cctgttgacg aaattgttga gtatggtcca acaaaagcag aaccaggtaa accagcggaa    3240
ccaggtaaac cagcggaacc aggtaaacca gcggaaccag gtacgccagc agaaccaggt    3300
aaaccagcgg aaccaggtac gccagcagaa ccaggtaaac cagcggaacc aggtaaacca    3360
gcggaaccag gtaaaccagc ggaaccaggt aaaccagcgg aaccaggtac gccagcagaa    3420
ccaggtacgc cagcagaacc aggtaaacca gcggaaccag gtacgccagc agaaccaggt    3480
aaaccagcgg aaccaggtac gccagcagaa ccaggtaaac cagcggaatc aggtaaacca    3540
gtggaaccag gtacgccagc acaatcaggt gcaccagaac aaccaaatag atcaatgcat    3600
tcaacagata taaaaatca attacctgat acaggtgaaa atcgtcaagc taatgaggga    3660
actttagtcg gatctctatt agcaattgtc ggatcattgt tcatatttgg tcgtcgtaaa    3720
aaaggtaatg aaaaataatt tcatataaaa actttctgcc attaa                   3765
```

<210> SEQ ID NO 21
<211> LENGTH: 546
<212> TYPE: PRT
<213> ORGANISM: Staphylococcus epidermidis

<400> SEQUENCE: 21

```
Glu Lys Gln Val Asp Pro Ile Thr Gln Ala Asn Gln Asn Asp Ser Ser
1               5                   10                  15

Glu Arg Ser Leu Glu Asn Thr Asn Gln Pro Thr Val Asn Asn Glu Ala
            20                  25                  30

Pro Gln Met Ser Ser Thr Leu Gln Ala Glu Glu Gly Ser Asn Ala Glu
        35                  40                  45

Ala Pro Gln Ser Glu Pro Thr Lys Ala Glu Glu Gly Gly Asn Ala Glu
    50                  55                  60

Ala Ala Gln Ser Glu Pro Thr Lys Ala Glu Glu Gly Gly Asn Ala Glu
65                  70                  75                  80

Ala Pro Gln Ser Glu Pro Thr Lys Ala Glu Glu Gly Gly Asn Ala Glu
                85                  90                  95

Ala Ala Gln Ser Glu Pro Thr Lys Thr Glu Glu Gly Ser Asn Val Lys
            100                 105                 110

Ala Ala Gln Ser Glu Pro Thr Lys Ala Glu Glu Gly Ser Asn Ala Glu
        115                 120                 125

Ala Pro Gln Ser Glu Pro Thr Lys Thr Glu Glu Gly Ser Asn Ala Lys
    130                 135                 140

Ala Ala Gln Ser Glu Pro Thr Lys Ala Glu Glu Gly Gly Asn Ala Glu
145                 150                 155                 160

Ala Ala Gln Ser Glu Pro Thr Lys Thr Glu Glu Gly Ser Asn Ala Glu
```

```
                    165                 170                 175
Ala Pro Gln Ser Glu Pro Thr Lys Ala Glu Glu Gly Gly Asn Ala Glu
                180                 185                 190

Ala Pro Gln Ser Glu Pro Thr Lys Thr Glu Glu Gly Gly Asn Ala Glu
                195                 200                 205

Ala Pro Asn Val Pro Thr Ile Lys Ala Asn Ser Asp Asn Asp Thr Gln
                210                 215                 220

Thr Gln Phe Ser Glu Ala Pro Thr Arg Asn Asp Leu Ala Arg Lys Glu
225                 230                 235                 240

Asp Ile Pro Ala Val Ser Lys Asn Glu Glu Leu Gln Ser Ser Gln Pro
                245                 250                 255

Asn Thr Asp Ser Lys Ile Glu Pro Thr Thr Ser Glu Pro Val Asn Leu
                260                 265                 270

Asn Tyr Ser Ser Pro Phe Met Ser Leu Leu Ser Met Pro Ala Asp Ser
                275                 280                 285

Ser Ser Asn Asn Thr Lys Asn Thr Ile Asp Ile Pro Pro Thr Thr Val
                290                 295                 300

Lys Gly Arg Asp Asn Tyr Asp Phe Tyr Gly Arg Val Asp Ile Glu Ser
305                 310                 315                 320

Asn Pro Thr Asp Leu Asn Ala Thr Asn Leu Thr Arg Tyr Asn Tyr Gly
                325                 330                 335

Gln Pro Pro Gly Thr Thr Thr Ala Gly Ala Val Gln Phe Lys Asn Gln
                340                 345                 350

Val Ser Phe Asp Lys Asp Phe Asp Phe Asn Ile Arg Val Ala Asn Asn
                355                 360                 365

Arg Gln Ser Asn Thr Thr Gly Ala Asp Gly Trp Gly Phe Met Phe Ser
                370                 375                 380

Lys Lys Asp Gly Asp Asp Phe Leu Lys Asn Gly Gly Ile Leu Arg Glu
385                 390                 395                 400

Lys Gly Thr Pro Ser Ala Ala Gly Phe Arg Ile Asp Thr Gly Tyr Tyr
                405                 410                 415

Asn Asn Asp Pro Leu Asp Lys Ile Gln Lys Gln Ala Gly Gln Gly Tyr
                420                 425                 430

Arg Gly Tyr Gly Thr Phe Val Lys Asn Asp Ser Gln Gly Asn Thr Ser
                435                 440                 445

Lys Val Gly Ser Gly Thr Pro Ser Thr Asp Phe Leu Asn Tyr Ala Asp
                450                 455                 460

Asn Thr Thr Asn Asp Leu Asp Gly Lys Phe His Gly Gln Lys Leu Asn
465                 470                 475                 480

Asn Val Asn Leu Lys Tyr Asn Ala Ser Asn Gln Thr Phe Thr Ala Thr
                485                 490                 495

Tyr Ala Gly Lys Thr Trp Thr Ala Thr Leu Ser Glu Leu Gly Leu Ser
                500                 505                 510

Pro Thr Asp Ser Tyr Asn Phe Leu Val Thr Ser Gln Tyr Gly Asn
                515                 520                 525

Gly Asn Ser Gly Thr Tyr Ala Ser Gly Val Met Arg Ala Asp Leu Asp
                530                 535                 540

Gly Ala
545

<210> SEQ ID NO 22
<211> LENGTH: 36
<212> TYPE: PRT
<213> ORGANISM: Staphylococcus aureus
```

-continued

```
<400> SEQUENCE: 22

Leu Pro Asn Thr Gly Ser Glu Glu Met Asp Leu Pro Leu Lys Glu Leu
1               5                   10                  15

Ala Leu Ile Thr Gly Ala Ala Leu Leu Ala Arg Arg Arg Ser Lys Lys
            20                  25                  30

Glu Lys Glu Ser
        35

<210> SEQ ID NO 23
<211> LENGTH: 43
<212> TYPE: PRT
<213> ORGANISM: Staphylococcus aureus

<400> SEQUENCE: 23

Leu Pro Asp Thr Gly Asp Ser Ile Lys Gln Asn Gly Leu Leu Gly Gly
1               5                   10                  15

Val Met Thr Leu Leu Val Gly Leu Gly Leu Met Lys Arg Lys Lys Lys
            20                  25                  30

Lys Asp Glu Asn Asp Gln Asp Ser Gln Ala
        35                  40

<210> SEQ ID NO 24
<211> LENGTH: 35
<212> TYPE: PRT
<213> ORGANISM: Staphylococcus aureus

<400> SEQUENCE: 24

Leu Pro Lys Thr Gly Glu Thr Thr Ser Ser Gln Ser Trp Trp Gly Leu
1               5                   10                  15

Tyr Ala Leu Leu Gly Met Leu Ala Leu Phe Ile Pro Lys Phe Arg Lys
            20                  25                  30

Glu Ser Lys
        35

<210> SEQ ID NO 25
<211> LENGTH: 38
<212> TYPE: PRT
<213> ORGANISM: Staphylococcus aureus

<400> SEQUENCE: 25

Leu Pro Lys Thr Gly Leu Thr Ser Val Asp Asn Phe Ile Ser Thr Val
1               5                   10                  15

Ala Phe Ala Thr Leu Ala Leu Leu Gly Ser Leu Ser Leu Leu Leu Phe
            20                  25                  30

Lys Arg Lys Glu Ser Lys
        35

<210> SEQ ID NO 26
<211> LENGTH: 36
<212> TYPE: PRT
<213> ORGANISM: Staphylococcus aureus

<400> SEQUENCE: 26

Leu Pro Gln Thr Gly Glu Glu Ser Asn Lys Asp Met Thr Leu Pro Leu
1               5                   10                  15

Met Ala Leu Ile Ala Leu Ser Ser Ile Val Ala Phe Val Leu Pro Arg
            20                  25                  30

Lys Arg Lys Asn
        35
```

```
<210> SEQ ID NO 27
<211> LENGTH: 34
<212> TYPE: PRT
<213> ORGANISM: Staphylococcus aureus

<400> SEQUENCE: 27

Leu Pro Lys Thr Gly Thr Asn Gln Ser Ser Pro Glu Ala Met Phe
1               5                   10                  15
Val Leu Ala Gly Ile Gly Leu Ile Ala Thr Val Arg Arg Lys
            20                  25                  30
Ala Ser

<210> SEQ ID NO 28
<211> LENGTH: 33
<212> TYPE: PRT
<213> ORGANISM: Staphylococcus aureus

<400> SEQUENCE: 28

Leu Pro Lys Thr Gly Leu Glu Ser Thr Gln Lys Gly Leu Ile Phe Ser
1               5                   10                  15
Ser Ile Ile Gly Ile Ala Gly Leu Met Leu Ala Arg Arg Arg Lys
            20                  25                  30
Asn

<210> SEQ ID NO 29
<211> LENGTH: 39
<212> TYPE: PRT
<213> ORGANISM: Staphylococcus aureus

<400> SEQUENCE: 29

Leu Pro Lys Ala Gly Glu Thr Ile Lys Glu His Trp Leu Pro Ile Ser
1               5                   10                  15
Val Ile Val Gly Ala Met Gly Val Leu Met Ile Trp Leu Ser Arg Arg
            20                  25                  30
Asn Lys Leu Lys Asn Lys Ala
        35

<210> SEQ ID NO 30
<211> LENGTH: 8
<212> TYPE: PRT
<213> ORGANISM: Staphylococcus epidermidis

<400> SEQUENCE: 30

Thr Tyr Tyr Phe Thr Asp Val Lys
1               5

<210> SEQ ID NO 31
<211> LENGTH: 9
<212> TYPE: PRT
<213> ORGANISM: Staphylococcus epidermidis

<400> SEQUENCE: 31

Thr Tyr Thr Phe Thr Val Tyr Val Asp
1               5

<210> SEQ ID NO 32
<211> LENGTH: 5
<212> TYPE: PRT
<213> ORGANISM: Staphylococcus epidermidis
<220> FEATURE:
<221> NAME/KEY: misc_feature
<222> LOCATION: (3)..(3)
<223> OTHER INFORMATION: Xaa can be any naturally occurring amino acid
```

```
-continued

<400> SEQUENCE: 32

Leu Pro Xaa Thr Gly
1               5

<210> SEQ ID NO 33
<211> LENGTH: 5
<212> TYPE: PRT
<213> ORGANISM: Staphylococcus epidermidis

<400> SEQUENCE: 33

Leu Pro Lys Ala Gly
1               5
```